US009567373B2

(12) United States Patent
Watt et al.

(10) Patent No.: US 9,567,373 B2
(45) Date of Patent: Feb. 14, 2017

(54) METHODS OF CONSTRUCTING AND SCREENING LIBRARIES OF PEPTIDE STRUCTURES

(71) Applicant: Phylogica Limited, Subiaco, WA (US)

(72) Inventors: Paul Michael Watt, Mount Claremont (AU); Roland Dunbrack, Philadelphia, PA (US)

(73) Assignee: Phylogica Limited, Subiaco (AU)

( * ) Notice: Subject to any disclaimer, the term of this patent is extended or adjusted under 35 U.S.C. 154(b) by 683 days.

(21) Appl. No.: 14/038,660

(22) Filed: Sep. 26, 2013

(65) Prior Publication Data

US 2014/0128268 A1 May 8, 2014

Related U.S. Application Data

(62) Division of application No. 11/672,419, filed on Feb. 7, 2007, now Pat. No. 8,575,070.

(30) Foreign Application Priority Data

Feb. 20, 2006 (AU) ................................ 2006900864

(51) Int. Cl.
| | | |
|---|---|---|
| *C40B 40/10* | (2006.01) | |
| *C07K 14/00* | (2006.01) | |
| *C07K 1/04* | (2006.01) | |
| *C12N 15/10* | (2006.01) | |
| *C40B 30/02* | (2006.01) | |
| *C07K 1/00* | (2006.01) | |
| *C07K 7/08* | (2006.01) | |

(52) U.S. Cl.
CPC ............... *C07K 14/001* (2013.01); *C07K 1/00* (2013.01); *C07K 1/047* (2013.01); *C07K 7/08* (2013.01); *C12N 15/1037* (2013.01); *C12N 15/1072* (2013.01); *C40B 30/02* (2013.01); *C40B 40/10* (2013.01)

(58) Field of Classification Search
None
See application file for complete search history.

(56) References Cited

U.S. PATENT DOCUMENTS

| | | |
|---|---|---|
| 5,516,637 A | 5/1996 | Huang et al. |
| 5,763,239 A | 6/1998 | Short et al. |
| 5,783,431 A | 7/1998 | Peterson et al. |
| 5,821,047 A | 10/1998 | Garrard et al. |
| 5,834,247 A | 11/1998 | Comb et al. |
| 6,083,715 A | 7/2000 | Georgiou et al. |
| 6,174,673 B1 | 1/2001 | Short et al. |
| 6,190,908 B1 | 2/2001 | Kang |
| 6,225,530 B1 | 5/2001 | Weigel et al. |
| 6,238,884 B1 | 5/2001 | Short et al. |
| 6,297,004 B1 | 10/2001 | Russell et al. |
| 6,316,223 B1 | 11/2001 | Payan et al. |
| 6,319,690 B1 | 11/2001 | Little et al. |
| 6,361,969 B1 | 3/2002 | Galeotti et al. |
| 6,436,694 B1 | 8/2002 | Tally et al. |
| 6,475,726 B1 | 11/2002 | Tally et al. |
| 6,521,425 B2 | 2/2003 | Perler et al. |
| 6,560,542 B1 | 5/2003 | Mandell et al. |
| 6,579,675 B2 | 6/2003 | Kamb |
| 6,583,275 B1 | 6/2003 | Doucette-Stamm et al. |
| 6,720,139 B1 | 4/2004 | Zyskind et al. |
| 6,720,413 B1 | 4/2004 | Schweinfest et al. |
| 6,846,625 B1 | 1/2005 | Tally et al. |
| 6,994,982 B1 | 2/2006 | Watt |
| 7,270,969 B2 | 9/2007 | Watt et al. |
| 7,315,786 B2 | 1/2008 | Dahiyat et al. |
| 7,803,765 B2 | 9/2010 | Watt et al. |
| 2002/0150906 A1 | 10/2002 | Debe |
| 2002/0155564 A1 | 10/2002 | Medrano et al. |
| 2002/0164735 A1 | 11/2002 | Olson et al. |
| 2002/0177170 A1 | 11/2002 | Luo et al. |
| 2003/0215846 A1 | 11/2003 | Watt et al. |
| 2005/0027457 A1 | 2/2005 | Mandell et al. |

(Continued)

FOREIGN PATENT DOCUMENTS

| | | |
|---|---|---|
| AU | 756617 | 2/2000 |
| AU | 771534 | 11/2000 |

(Continued)

OTHER PUBLICATIONS

Alekshun, M.N. (Dec. 2001) "Beyond Comparison—Antibodies From Genome Data?" *Nature Biotechnology* 19:1124-1125.
Amann, E. et al. (1985) "ATG Vectors for Regulated High-Level Expression of Cloned Genes in *Escherichia coli*," *Gene* 40:183-190.
Amstutz, P. et al. (2001) "In vitro Display Technologies: Novel Developments and Applications," Current Opinion in Biotechnology 12:400-405.
Andre, S. et al. (Jan. 17, 2005). "Identification of Peptide Ligands for Malignancy- and Growth-Related Galectins Using Random Phage-Display and Designed Combinatorial Peptide Libraries," Bioorganic & Medicinal Chemistry 13(2):563-573.
Angrist, M. (1998) "Less is More: Compact Genomes Pay Dividends," Genome Research 8:683-685.

(Continued)

*Primary Examiner* — Christian Boesen
(74) *Attorney, Agent, or Firm* — Carol L. Francis; Bozicevic, Field & Francis LLP

(57) ABSTRACT

The present invention provides the means for producing libraries of peptide structures for drug screening applications that are capable of folding or assuming their native conformations independently of artificial scaffolds or flanking sequences in the proteins from which they are derived. The libraries can be highly diverse such that they are representative of the repertoire of protein structures existing in nature. The libraries can also be non-redundant or normalized such that the bias towards specific structures existing in source data sets and/or in nature is/are removed. In a particularly preferred embodiment, the present invention provides 30,000 independent fold structures produced by this method. The present invention also provides computer-readable media and systems comprising structural data in relation to the peptide libraries, and methods for displaying and screening the libraries.

3 Claims, No Drawings

(56) References Cited

U.S. PATENT DOCUMENTS

| | | |
|---|---|---|
| 2005/0287580 A1 | 12/2005 | Watt et al. |
| 2007/0031832 A1 | 2/2007 | Watt |
| 2008/0139401 A1 | 6/2008 | Watt |
| 2009/0170722 A1 | 7/2009 | Watt et al. |

FOREIGN PATENT DOCUMENTS

| | | |
|---|---|---|
| EP | 1277835 | 1/2003 |
| WO | WO 9517412 | 6/1995 |
| WO | WO 9623075 | 8/1996 |
| WO | WO 9624684 | 8/1996 |
| WO | WO 9640979 | 12/1996 |
| WO | WO 9815172 | 4/1998 |
| WO | WO 9816835 | 4/1998 |
| WO | WO 9819162 | 5/1998 |
| WO | WO 9935282 | 7/1999 |
| WO | WO 9939210 | 8/1999 |
| WO | WO 0068373 | 11/2000 |
| WO | WO 0076308 | 12/2000 |
| WO | WO 0111086 | 2/2001 |
| WO | WO 03012055 | 2/2003 |
| WO | WO 03014325 | 2/2003 |
| WO | WO 03040168 | 5/2003 |
| WO | WO 03046147 | 6/2003 |
| WO | WO 03076621 | 9/2003 |
| WO | WO 2004074479 | 9/2004 |
| WO | WO 2006017913 | 2/2006 |

OTHER PUBLICATIONS

Arenkov, P, et al (2000). "Protein Microchips: Use for Immunoassay and Enzymatic Reactions," Analytical Biochemistry 278: 123-131.

Bains et al (1997) "Zipping up transcription factors: Rational Design of Anti-Jun and Anti-Fos Peptides" *Letters in Peptide Science* 4:67-77.

Balaban, N. et al. (Apr. 17, 1998). "Autoinducer of Virulence as a Target for Vaccine and Therapy Against *Staphylococcus aureus*," Science 280:438-440.

Basbous, J. et al. (Oct. 31, 2003). "The HBZ Factor of Human T-cell Leukemia Virus Type 1 Dimerizes with Transcription Factors JunB and cJun Modulates Their Transcriptional Activity," The Journal of Biological Chemistry 278 (44): 43620-43627.

Baud, F. et al. (Oct. 26, 1999). "Measures of Residue Density in Protein Structures," Proc. Natl. Acad. Sci. USA 96:12494-12499.

Behrens, A. et al. (Mar. 1999). "Amino-Terminal Phosphorylation of c-Jun Regulates Stress-Induced Apoptosis and Cellular Proliferation," Nature Genetics 21:326-329.

Berzofky, J.A. (Sep. 6, 1985). "Intrinsic and Extrinsic Factors in Protein Antigenic Structure," Science 229(4717):932-940.

Bianco et al (2006) "Solid-phase synthesis of CD40L mimetics" *Org. Biomol. Chem* 4:1461-1463.

Blum, J.H. et al. (Feb. 29, 2000), "Isolation of Peptide Aptamers That Inhibit Intracellular Processes," Proc. Natl. Acad. Sci. USA 97(5):2241-2246.

Bonaldo, M. et al. (1996). "Normalisation and Subtraction: Two Approaches to Facilitate Gene Discovery," Genome Res. 6:791-806.

Bremnes, T. et al. (1998). "Selection of Phage Displayed Peptides From a Random 10-mer Library Recognising a Peptide Target," Immunotechnology 4:21-28.

Britten, R.J. et al. (Aug. 9, 1968). "Repeated Sequences in DNA," Science 161(3841):529-540.

Brodin, N. T. et al. (May 15, 1990). "Rat Monoclonal Antibodies Produced Against Rat Colorectal Adenocarcinomas Define Tumor- and Colon-Associated, Auto-Immunogenic Antigens," Int. J. Cancer 45(5):902-910.

Burioni, R. et al. (1998). "A New Subtraction Technique for Molecular Cloning of Rare Antiviral Antibody Specificities From Phage Display Libraries," Res. Virol. 149:327-330.

Campbell, A.P. et al. (1997). "Solution Secondary Structure of a Bacterially Expressed Peptide from the Receptor Binding Domain of Pseudomonas aeruginosa Pili Strain PAK: A Heteronuclear Multidimensional NMR Study" Biochem. 36(42):12791-12801.

Canchaya et al (2003) "Prophage Genomics" *Microbiology and Molecular Biology Reviews* 67(2):238-276.

Canchaya et al (2003) "Prophage Genomics" *Microbiology and Molecular Biology Reviews* 67(3):473. Erratum.

Caponigro, G. et al. (Jun. 1998). "Transdominant Genetic Analysis of a Growth Control Pathway," Proc. Natl. Acad. Sci USA 95:7508-7513.

Chapman, M.D, et al. (Nov. 1984). "Recognition of two Dermatophagoides pteronyssinus-specific Epitopes on Antigen P1 by using Monoclonal Antibodies: Binding to Each Epitope can be Inhibited by Serum from Dust Mite-Allergic Patients," J. Immunol 133(5):2488-.

Chen et al (2006) "Thermal injury-induced peroxynitrite production and pulmonary inducible nitric oxide synthase expression depend on JNK/AP-1 signalling" *Crit Care Med* 34(1):142-150.

Chevray, P.M. et al. (Jul. 1992). "Protein Interaction Cloning in Yeast: Identification of Mammalian Proteins that React with the Leucine Zipper of Jun," Proc. Natl. Acad. Sci. USA 89: 5789-5793.

Chloupkova et al (2003) "MDL1 is a High Copy Suppressor of ATM1: Evidence for a Role in Resistance to Oxidative Stress" *JMB* 331:155-165.

Choi, Y. et al. (Mar. 2003). "Identification of Bioactive Moleculesby Adipogenesis Profiling of Organic Compounds" FASEB Meeting on Experimental Biology: Translating the Genome, San Diego, CA, Apr. 11-15, 2003, 17(4-5):A605, Abstract No. 377.23, one page.

Colas et al. (Apr. 11, 1996). "Genetic Selection of Peptide Aptamers That Recognize and Inhibit Cyclin-Dependent Kinase 2," Nature 380:548-550.

Colbére-Garapin et al. (1981). "A New Dominant Hybrid Selective Marker for Higher Eukaryotic Cells," J. Mol. Biol. 150:1-14.

Cordwell, S.J. (1999) "Microbial Genomes and 'Missing' Enzymes: Redefining Biochemical Pathways," Arch. Microbial. 172:269-279.

Davies, J.M. et al. (Jun. 2000). "Use of Phage Display Technology to Investigate Allergen-Antibody Interactions," J. Allergy Clin. Immunol. 105(6): 1085-1 092 2000.

Day et al (2003) "A consensus view offold space: Combining SCOP, CATH, and the Dali Domain Dictionary" *Protein Science* 12:2150-2160.

Dayalan, S. et al (2006) "Dihedral Angle and Secondary Structure Database of Short Amino Acid Fragments" *Bioinformation* 1(3):78-80.

De Soultrait et al. (2002). "A Novel Short Peptide is a Specific Inhibitor of the Human Immunodeficiency Virus Type 1 Integrase," J. Mol. Biol. 318:45-58.

Deambrosis et al (2009) "Inhibition of CD40-CD154 Costimulatory Pathway by a Cyclic Peptide Targeting CD 154" *J Mol Med* 87:181-197.

Dent et al. (2000). "The Genetics of Ivermectin Resistance in Caenorhabditis elegans," Proc. Natl. Acad. Sci. USA 97:2674-2679.

Derossi et al. (1994). "The Third Helix of the Antennapedia Homeodomain Translocates Through Biological Membranes," J. Biol. Chem. 269: 10444-10450.

Deveraeux et al. (1984). "A Comprehensive Set of Sequence Analysis Programs for the VAX," Nucl. Acids Res. 12:387-395.

Devito et al. (2002). "An Array of Target-Specific Screening Strains for Antibacterial Discovert," Nature Biotechnology 20:478-483.

Encode Project Consortium (2007) "Identification and analysis of functional elements in 1% of the human genome by the Encode pilot project" *Nature* 447:799-816.

Erdos, G. et al. (2006). "Construction and Characterization of a Highly Redundant Pseudonomas aeruginosa Genomic Library Prepared From 12 Clinical Isolates: Application to Studies of Gene Distribution Among Populations," Intl. Journal of Pediatric Otorhinolaryngology.

Estus, S. et al. (Dec. 1994). "Altered Gene Expression in Neurons During Programmed Cell Death: Identification of c-Jun as Necessary for Neuronal Apoptosis," The Journal of Cell Biology 127(6):1717-1727.

(56) References Cited

OTHER PUBLICATIONS

Faber et al. (1999). "Polyglutamine-Mediated Dysfunction and Apoptotic Death of a Caenorhabditis elegans Sensory Neuron," Proc. Natl. Acad. Sci. 96: 179-184.
Fabret et al. (2000). "Efficient Gene Targeted Random Mutagenesis in Genetically Stable *Escherichia coli* strains," Nucl. Acids Res. 28:e95.
Fahraeus et al. (1996) "Inhibition of prb Phosphorylation and Cell-Cycle Progression by a 20-Residue Peptide Derived From p16 CDKN2/INK4An," Curr. Biol. 6(1):84-91.
Fang, Y. et al. (2002). "G-Protein-Coupled Receptor Microarrays," ChemBioChem., 3: 987-991.
Fehrsen et al. (1999). "Cross-Reactive Epitope Mimics in a Fragmented-Genome Phage Display Library Derived from the Rickettsia, Cowdria ruminantium," Immunotechnology 4: 175-184.
Filipe, S.R. (2001). "The Role of murMN Operon in Penicillin Resistance and Antibiotic Tolerance of *Streptococcus pneumoniae*," Microbial Drug Resistance 7(4):303-316.
Fischer et al (2000) "A Rapid Test for Identification of Autonomous Folding Units in Protein" *J. Mol. Biol.* 302:701-712.
Fitzgerald (2000). "In vitro Display Technologies—New Tools for Drug Discovery," Drug Discovery Today 5:253-258.
Floudas et al (2006) "Advances in protein structure prediction and de novo protein design: A review" *Chemical Engineering Science* 61:966-988.
Franzoni et al. (1997). "Structure of the C-Terminal Fragment 300-320 of the Rat Angiotensin II AT la Receptor and Its Relevance with Respect to G-Protein-Coupling," J. Biol. Chem. 272:9734-9741.
Fromant et al (1995) "Direct random mutagenesis of gene-sized DNA fragments using polymerase chain reaction" *Analytical Biochemistry* 224:347-353.
Furmonaviciene, R. et al. (1999). "The Use of Phage-Peptide Libraries to Define the Epitope Specificity of a Mouse Monoclonal Anti-Der p 1 Response," Clin. Exp. Allergy 29: 1563-1 571.
Futch, W.S. Jr. et al. (Mar. 15, 2003). "Dissection of Macrophage Tumoricidal and Protozoacidal Activities Using TCell Hybridomas and Recombinant Lymphokines," Infection and Immunity 50(3): 709-715.
Gaasterland et al (1998) "Microbial Genescapes: Phyletic and Functional Patterns of ORF Distribution among Prokaryotes" *Microbial and Comparative Genomics* 3(4):199-217.
Garcia, M. et al. (Mar. 15, 2002). "The Mitochondrial Toxin 3-Nitropropionic Acid Induces Striatal Neurodegeneration via a c-Jun N-Terminal Kinase/c-Jun Module," The Journal of Neuroscience 22(6):2174-2184.
Gargala, G. et al. (1999). "Enzyme Immunoassay Detection of Cryptosporidium parvum Inhibition by Sinefungin in Sporozoite Infected HCT-8 Enterocytic Cells," International Journal of Parasitology 29: 703-709.
Gegg et al. (1997). "Probing Minimal Independent Folding Units in Dihydrofolate Reductase by Molecular Dissection," Protein Sci. 6: 1885-1892.
GenBank Accession No. AAH36335 (last updated May 20, 2005), located at <http://www.ncbi.nlm.nih.gov/entrez/viewer.fcgi?dbrotein&id=23273658, last visited Apr. 1, 2008, three pages.
GenBank Accession No. AAN49594 (last updated Feb. 1, 2006), <http://www.ncbi.nlm.nih.gov/entrez/viewer.fcgi?dbrotein&id=24196153>, last visited Apr. 1, 2008, two pages.
GenBank Accession No. AAS70149 (last updated Jan. 4, 2006), <http://www.ncbi.nlm.nih.gov/entrez/viewer.fcgi?dbrotein&id=45600665>, last visited Apr. 1, 2008, two pages.
GenBank Accession No. AAV59791 (last updated Jan. 21, 2005), <http://www.ncbi.nlm.nih.gov/entrez/viewer.fcgi?dbrotein&id=55736149>, last visited Apr. 1, 2008, three pages.
GenBank Accession No. CAD25932 (last updated Apr. 16, 2005), <http://www.ncbi.nlm.nih.gov/entrez/viewer.fcgi?dbrotein&id=19069547>, last visited Apr. 1, 2008, two pages.
GenBank Accession No. CAI310659 (last updated Sep. 22, 2004), <http://www.ncbi.nlm.nih.gov/entrez/viewer.fcgi?dbrote&id=5O949409>, last visited Apr. 1, 2008, two pages.
GenBank Accession No. XP975325, last updated Jul. 21, 2008, <http://www.ncbi.nlm.nih.gov/protein/91084013>.
GenBank Accession No. YP284595, last updated Jun. 10, 2013, <http://www.ncbi.nlm.nih.gov/protein/71907008>.
GenBank Accession No. ZP01044355, last updated Nov. 26, 2012, <http://www.ncbi.nlm.nih.gov/protein/ZP 01044355.1?report=genpept>.
Getzoff et al. (1987). "Mechanisms of Antibody Binding to a Protein," Science 235:1191-1196.
Giesen et al (2002) "The Oncogenic Activity of Cyclin E is Not Confined to Cdk2 Activation Alone but Relies on Several Other, District Functions of the Protein" *J Biol. Chem.* 277(42):39909-39918.
Granger-Schnarr, M. et al. (May 1992). "Transformation and Transactivation Suppressor Activity of the c-Jun Leucine Zipper Fused to a Bacterial Repressor," Proc. Natl. Acad. Sci. USA 89:4236-4239.
Greene et al. (1992). "IgE Binding Structures of the Major House Dust Mite Allergen DER P 1," Mol. Immunology 29:257-262.
Guda et al (2006) "DMAPS: a database of multiple alignments for protein structures" *Nucleic Acids Research* 34:D273-D276.
Haley, K.J. et al. (Aug. 1998). "Tumor Necrosis Factor Induces Neuroendocrine Differentiation in Small Cell Lung Cancer Cell Lines," American Journal of Physiology 275(2 pt 1):L3 11-L321.
Halstead, J.R. et al. (1999). "A Family 26 Mannanase Produced by Clostridium thermocellum as a Component of the Cellulosome Contains a Domain Which is Conserved in Mannanases from Anaerobic Fungi," Microbiology 145:3101-3108.
Harrison A. et al (2003) "Recognizing the Fold of a Protein Structure" *Bioinformatics* 19(14):1748-1759.
Hegde S. S. et al. (Mar. 9, 2001). "FemABX Family Members Are Novel Nonribosomal Peptidyltransferases and Important Pathogen-SpecificDrug Targets," The Journal of Biological Chemistry 276(10):6998-7003.
Hengeveld et al. (2002). "Functional and Structural Characterization of a Synthetic Peptide Representing the N-Terminal Domain of Prokaryotic Pyruvate Dehydrogenase," Biochem. 41:7490-7500.
Heymann et al. (1989). "Antigenic and Structural Analysis of Group I1 Allergens (Der f II and Der p II) From House Dust Mites (*Dermatophagoides* spp.)" J. Allergy Clin. Immunol 83:1055-1067.
Hofmann et al. (1996). "Rapid Retroviral Delivery of Tetracycline-Inducible Genes in a Single Autoregulatory Cassette," Proc. Natl. Acad. Sci. 93:5185-5190.
Hoogenboom et al. (1991). "Multi-Subunit Proteins on the Surface of Filamentous Phage: Methodologies for Displaying Antibody (Fab) Heavy and Light Chaims," Nucleic acids Res. 19:4133-4137.
Horng et al. (2002). "Characterization of Large Peptide Fragments Derived from the N-Terminal Domain of the Ribosomal Protein L9: Definition of the Minimum Folding Motif and Characterization of Local Electrostatic Interactions," Biochem. 41: 13360-13369.
Hosen, N. et al. (2004). "Identification of a Gene Element Essential for Leukemia -Specific Expression of Transgenes," Leukemia 18:415-419.
Houshmand et al. (1999). "Use of Bacteriophage T7 Displayed Peptides for Determination of Monoclonal Antibody Specificity and Biosensor Analysis of the Binding Reaction," Anal. Biochem. 268:363-370.
Humphrey et al. (1997). "Chemical Synthesis of Natural Product Peptides; Coupling Methods for the Incorporation of Noncoded Amino Acids into Peptides," Chem. Rev. 97:2243-2266.
Inouye et al (1997) "Mutational Analysis of STE5 in the Yeast *Saccharomyces cerevisiae*: Application of a Differential Interaction Trap Assay for Examining Protein-Protein Interactions" *Genetics* 147:479-492.
International Preliminary Report on Patentability mailed on Feb. 20, 2007, for PCT Application No. PCT/AU2005/001255, filed Aug. 22, 2005, ten pages.
International Search Report mailed on Aug. 16, 2005, for PCT Application No. PCT/AU2005/000801, filed Jun. 3, 2005, eight pages.

(56) References Cited

OTHER PUBLICATIONS

International Search Report mailed on Nov. 17, 2005, for PCT Application No. PCT/AU2005/001255, filed Aug. 22, 2005, six pages.
Irbäck, et al. (1996). "Evidence for Nonrandom Hydrophobicity Structures in Protein Chains," Proc. Natl. Acad. Sci. 93:9533-9538.
Izawa et al (2004) "A screening system for antioxidants using thioredoxin-deficient yeast: discover of thermostable antioxidant activity from Agaricus blazei Murill" *Applied Microbial and Cell Physiology* 64:537-542.
Kabouridis, P. S. (Nov. 2003). "Biological Applications of Protein Transduction Technology," Trends in Biotechnology 21(11): 498-503.
Kern et al (1992) "Oncogenic Forms of P53 Inhibit P53-Regulated Gene Expression" *Science* 256:5058:827-830.
Kinzler et al. (1989). "Whole Genome PCR: Application to the Identification of Sequences Bound by Gene Regulatory Proteins," Nucleic Acids Res. 17:3645-3653.
Kitagawa et al (2005) "Identification of Three Novel Peptides That Inhibit CD40-CD154 Interaction" *Mod Rheumatol* 15:423-426.
Kolonin et al. (Nov. 1998). "Targeting Cyclin-Dependent Kinases in Drosophilia with Peptide Aptamers," Proc. Natl. Acad. Sci. 95: 14266-14271.
Koncz et al. (1987). "Expression and Assembly of Functional Bacterial Luciferase in Plants," Proc. Natl. Acad. Sci. 84:131-135.
Koo, J.H. et al. (Mar. 8, 2001). "Purification and Characterization of Bex, an OMP Parter," Annual Meeting of the Federation of American Societies for Experimental Biology on Experimental Biology Orlando, FL, Mar. 31-Apr. 4, 2001, 15(5):A894, Abstract No. 695.14.
Kopczynski et al. (1998). "A High Throughput Screen to Identify Secreted and Transmembrane Proteins Involved in Drosophilia embryogenesis," Proc. Natl. Acad. Sci. 95:9973-9978.
Krissinel et al. (2004) "Secondary-structure matching (SSM), a new tool for fast protein structure alignment in three dimensions" *Acta Cryst* D60:2256-2268.
Lambros, C. et al. (Jun. 1979). "Synchronization of Plasmodium Falciparum Erythrocytic Stages in Culture," J. Parasitology 65(3):418-420.
Layne, M.D. et al. (Jun. 18, 1998). "Aortic Carboxypeptidase-Like Protein, Novel Protein with Discoidin and Carboxypeptidase-Like Domains, Is Up-Regulated During Vascular Smooth Muscle Cell Differentiation," The Journal of Biological Chemistry 273(25):15654-15660.
Lee et al. (1994) "Structure-Antigenicity Relationship of Peptides from the Pre-s2 Region of the Hepatitus B Virus Surface Antigen" *Biochem Mol Biol Int* 34(1):159-168.
Lee, et al. (1994). "Structure-Antigenicity Relationship of Peptides from the Pre-s2 Region of the Hepatitus B Virus Surface Antigen," Biochem Mol Biol Int. 34(1):159-168.
Lee, Y. et al. (2003). "ProteoChip: A Highly Sensitive Protein Microarray Prepared by a Novel Method of Protein Immobilization for Application of Protein-Protein Interaction Studies," Proteomics, 3:2289-2304.
Leitner, A. et al. (1998) "A Mimotope Defined by Phage Display Inhibits IgE Binding to the Plant Panallergen Profiling," Eur. J. Immunol 28:2921-2927.
Lesley et al. (1991). "Use of in vitro Protein Syntheses from Polymerase Chain Reaction-Generated Templates to Study Interaction of *Escherichia coli* Transcription Factors with Core RNA Polymerase and for Epitope Mapping of Monoclonal Antibodies," J. Biol. Chem. 266:2632-.
Lessel, et al., Creation and characterization of a new, non-redundant fragment data bank, Protein engineering, vol. 10, No. 6, pp. 659-664, 1997.
Lind, et al. (1988). "The Binding of Mouse Hybridoma and Human IgE Antibodies to the Major Fecal Allergen, Der p 1, of Dermatophagoides pteronyssinus," J. Immunol 40:4256-4262.

Lowman et al (1998) "Molecular Mimics of Insulin-like Growth Faction 1(IGF-1) for Inhibiting IGF-1:IGF-Binding Protein Interactions" Biochemistry 37:8870-8878.
Maggio et al (2001) "Recent developments in computational proteomics" *Trends in Bioechnology* 19(7):266-272.
Maidhof, H. et al. (Jun. 1991). "femA, Which Encodes a Factor Essential for Expression of Methicillin Resistance, Affects Glycine Content of Peptidoglycan in Methicillin-Resistant and Methicillin -Susceptible *Staphylococcus aureus* Strains," Journal of Bacteriology 173(11):3507-.
Marcello et al. (Sep. 1994). "Specific Inhibition of Herpes Virus Replication by Receptor-Mediated Entry of an Antiviral Peptide Linked to *Escherichia coli* Enterotoxin B Subunit," Proc. Natl. Acad. Sci. 91:8994-8998.
Marsh et al. (2000). "Expanded Polyglutamine Peptides Alone are Intrinsically Cytotoxic and Cause Neurodegeneration in Drosophilia," Hum. Mol. Genet. 9: 13-25.
Mazmanian, S. K. et al. (Jul. 30, 1999). "*Staphylococcus aureus* Sortase, an Enzyme that Anchors Surface Proteins to the Cell Wall," Science, 285:760-763.
Mazmanian, S. K. et al. (May 9, 2000) "*Staphylococcus aureus* Sortase Mutants Defective in the Display of Surface Proteins and in the Pathogenesis of Animal Infections," Proc. Natl. Acad. Sci. 97(10):5510-5515.
McCafferty et al. (1990). "Phage Antibodies: Filamentous Phage Displaying Antibody Variable Domains," Nature 348:552-554.
McConnell et al. (1994). "Constrained Peptide Libraries as a Tool for Finding Mimotopes," Gene 15 1:115-118.
McElveen, J.E. (1998). "Primary Sequence and Molecular Model of the Variable Region of a Mouse Monoclonal Anti- Der p 1 Antibody Showing a Similar Epitope Specificity as Human IgE," Clinical and Experimental Allergy 28:1427-1434.
Mennuni et al. (1997). "Identification of a Novel Type 1 Diabetes-Specific Epitope by Screening Phage Libraries with Sera from Pre-Diabetic Patients," J. Mol. Biol. 268:599-606.
Michiels, F. et al. (Nov. 2002). "Arrayed Adenoviral Expression Libraries for Functional Screening," Nature Biotechnology 20: 1154-1157.
Miller, V.L. et al. (Sep. 2001). "Identification of Regions of All Required for the Invasion and Serum Resistance Phenotypes," Molecular Microbiology 41(5):1053-1062.
Morris et al. (2000). "Translocating Peptides and Proteins and Their Use for Genen Delivery," Curr. Opinion Biotech. 11:461-466.
Morris et al. (2001). "A Peptide Carrier for the Delivery of Biologically Active Proteins into Mammalian Cells," Nature Biotech. 19:1173-1176.
Mulligan et al. (1981). "Selection for Animal Cells that Express the *Escherichia coli* Gene Coding for Xanthine- Guanine Phosphoribosyltransferase," Proc. Natl. Acad. Sci. USA 78:2072-2076.
Nedelkov, D. et al. (2001). "Analysis of Native Proteins from Biological Fluids by Biomolecular Interaction Analysis Mass Spectrometry (BIA/MS): Exploring the Limit of Detection, Identification of Non-Specific Binding and Detection of Multi-Protein Complexes."
Needleman et al. (1970). "A General Method Applicable to the Search for Similarities in the Amino Acid Sequence of Two Proteins," J. Mol. Biol. 48:443-453.
Neidigh et al. (2002). "Designing a 20-Residue Protein," Nature Structural Biology 9:425-430.
Nelson R.W. et al. (2000). "Biosensor Chip Mass Spectrometry: A Chip-Based Proteomics Approach," Electrophoresis 21:1155-1163.
Nelson, K.E. et al. (Oct. 2000). "Status of Genome Projects for Nonpathogenic Bacteria and Archaea," Nature Biotechnology 18:1049-1054.
Nelson, R.W. et al. (1999). "BIAMS of Epitope-Tagged Peptides Directly from *E. Coli* Lysate: Multiplex Detection and Protein Identification at Low-Fermtomole to Subfemtomole Levels," Anal. Chem. 713:2858-2865.
Nemoto N. et al. (1999). "Fluorescence Labeling of the C-Terminus of Proteins with a Puromycin Analogue in Cell- Free Translation Systems," FEBS Letters 462:43-46.

(56) References Cited

OTHER PUBLICATIONS

Ness et al. (2002). "Synthetic Shuffling Expands Functional Protein Diversity by Allowing Amino Acids to Recombine Independently," Nature Biotechnology 20:1251-1255.
Norman et al. (1999). "Genetic Selection of Peptide Inhibitors of Biological Pathways," Science 285:591-595.
Oefner, P.J. et al. (1996). "Efficient Random Subcloning of DNA Sheared in a Recirculating Point-Sink Flow System," Nucleic Acids Research 24(20):3879-3886.
O'Hare et al. (1981). "Transformation of Mouse Fibroblasts to Methotrexate Resistance by a Recombinant Plasmid Expressing a Prokaryotic Dihydrofolate Reductase," Proc. Natl. Acad. Sci. USA 78:1527-1531.
Olins et al (1995) "Saturation Mutagenesis of Human Interleukin-3" JBC 270(40):23754-23760.
Palzkill et al. (1998). "Mapping Protein-Ligand Interactions Using Whole Genome Phage Display Libraries," Gene 221:79-83.
Pande et al. (1994). "Nonrandomness in Protein Sequences: Evidence for a Physically Driven Stage of Evolution?" Proc. Natl. Acad. Sci. USA 91:12972-12975.
Pavlickova, P. et al. (2003). "Microarray of Recombinant Antibodies Using a Streptavidin Sensor Surface Self-Assembled onto a Gold Layer," BioTechniques 34(1):124-130.
Phelan et al. (May 1998). "Intercellular Delivery of Functional p53 by the Herpes Virus Protein VP22," Nature Biotechnol. 16:440-443.
Phylogica Beyond Antibodies, (Oct. 2005) PowerPoint slides.
Pincus et al. (1998). "Peptides that Mimic the Group B Streptococcal Type I11 Capsular Polysaccharide Antigen," J. Immunol. 160:293-298.
Pini et al. (Aug. 21, 1998). "Design and Use of a Phage Display Library," J. Biol. Chem. 21769-21776.
Polacco et al (2006) "Automated discovery of 30 motifs for protein function annotation" Bioinformatics 22(6): 723-730.
Postier, B.L. et al. (2003). "The Construction and Use of Bacterial DNA Microarrays Based on an Optimized Two- Stage PCR Strategy," BMC Genomics, vol. 4, 11 pages.
Raivich et al (2006) "Role of the AP-1 Transcription Factor c-Jun in Developing, Adult and Injured Brain" Progress in Neurobiology 78:347-363.
Read et al. (2001). "Finding Drug Targets in Microbial Genomes," Drug Disc. Today 6:887-892.
Richter et al. (2000). "Refolding, Purification, and Characterization of Human Recombinant pde4a Constructs Expressed in *Escherichia coli*," Protein Expression and Purification 19:375-383.
Robben et al. (2002). "Selection and Identification of Dense Granule Antigen GRA3 by Toxoplasma gindii Whole Genome Phage Display," J. Biol. Chem. 277:17544-17547.
Roberts et al. (1997). "RNA-Peptide Fusions for the in vitro Selection of Peptides and Proteins," Proc. Natl. Acad. Sci. USA 94: 12297-12302.
Rogers et al. (1997). "Behavioral and Functional Analysis of Mouse Phenotype: SHRPA, a Proposed Protocol for Comprehensive Phenotype Assessment," Mamm. Genome 8:711-713.
Rohrer, S. et al. (Aug. 1999). ":The Essential *Staphylococcus aureus* Gene fmhB is Involved in the First Step of Peptidoglycan Pentaglycine Interpeptide Formation," Proc. Natl. Acad. Sci. USA, 96: 9351-9356.
Rosenthal, P. J. et al. (Jul. 1996). "Antimalarial Effects of Vinyl Sulfone Cysteine Proteinase Inhibitors," Antimicrobial Agents and Chemotherapy 40(7): 1600-1 603.
Sali & Blundell (1993) "Comparative protein modelling by satisfaction of spatial restraints" *J Mol Biol* 234(3):779-815.
Sambrook et al. (1989). "Screening Expression Libraries with Antibodies and Oligonucleotides" Molecular Cloning: A Laboratory Manual Second Edition, Cold Spring Harbor Laboratory Press, USA. Chapter 12, p. 12.2.
Santangelo et al (1986) "Cloning of open reading frames and promoters from the *Saccharomyces cerevisiae* genome: construction of genomic libraries of random small fragments" Gene, 46(2-3):181-6.
Santerre et al. (1984). "Expression of Prokaryotic Genes for Hygromycin B and G418 Resistance as Dominant- Selection Markers in Mouse L Cells," Gene 30:147-156.
Satyal et al. (2000). "Polyglutamine Aggregates Alter Protein Folding Homeostatis in Caenorhabditis elegans," Proc. Natl. Acad. Sci. USA 97:5750-5755.
Serebriiskii et al (1999) "A two-hybrid dual bait system to discriminate specificity of protein Interactions" *J Biol Chem* 274(24): 17080-17087.
Serebriiskii et al (2000) "Approaches to Detecting False Positives in Yeast Two-Hybrid Systems" *Biotechniques* 28(2):328-336.
Serebriiskii et al (2002) "Detection of Peptides, Proteins, and Drugs that Selectively Interact with Protein Targets" *Genome Res.* 12:1785-1791.
Serebriiskii et al (2004) "Analysis of Protein-Protein Interactions Utilizing Dual Bait Yeast Two-Hybrid System" Chapter 19 in *Methods of Molecular Biology*, Fu, H., ed, Humana Press, Inc. Totwas:New Jersey, 261:263-296.
Shafikhani et al. (1997). "Generation of Large Libraries of Random Mutants in Bacillus subtilis by PCR-based Plasmid Multimerization" Biotechniques 23(2):304-310.
Shimatake et al. (198 1). "Purified h Regulatory Protein cII Positively Activates Promoters for Lysogenic Development,"Nature 292:128-132.
Sieber et al. (2001). "Libraries of Hybrid Proteins from Distantly Related Sequences," Nature Biotechnology 19:456-460.
Sigal et al (2000) "Oncogenic Mutations of the p53 Tumor Suppressor: The Demons of the Guardian of the Genome" Cancer Research 60:6788-6793.
Skelton et al (2001) "Structure-Function Analysis of a Phage Display-Derived Peptide That Binds to Insulin-like Growth Faction Binding Protein 1" Biochemistry 40:8487-8489.
Soares, M.B. (1997). "Identification and Cloning of Differentially Expressed Genes," Curr. Opinion Biotechnol. 8:542-546.
Stengelin et al. (1988). "Isolation of cDNAs for Two Distinct Human Fc Receptors by Ligand Affinity Cloning," EMBO Journal 7:1053-1059.
Stranden, A.M. et al. (Jan. 1997). "Cell Wall Monoglycine Cross-Bridges and Mathicillin Hypersusceptibility in a femAB Null Mutant of Methicillin-Resistant *Staphylococcus aureus*," Journal of Bacteriology 179(1): 9-16.
Studier et al. (1986). "Use of Bacteriophage T7 RNA Polymerase to Direct Selective High-Level Expression of Cloned Genes," J. Mol. Biol. 189:113-130.
Sugita et al. (2002) "Combined Use of Oligonucleotide and Tissue Microarrays Identifies Cancer/Testis Antigens as Biomarkers in Lung Carcinoma," Cancer Res 62:3971-3979.
Supplementary Partial European Search Report for EP Application No. 04712970.5 mailed Apr. 26, 2006, five pages.
Supplementary Partial European Search Report for EP Application No. 04712970.5 mailed Aug. 3, 2006, seven pages.
Szwarcwort-Cohen et al (2009) "Human Cdk2 is a functional homolog of budding yeast lme2, the meiosis-specific Cdk-like kinase" *Cell Cycle* 8(4):647-654.
Theiss, H.D. et al. (2003). "Enhancement of Gene Transfer With Recombinant Adeno-Associated Virus (rAAV) Vectors into Primary B-Cell Chronic Lymphocytic Leukemia Cells by CpG-oligodeoxynucleotides," Experimental Hematology 3 1: 1223-1229.
Thomas et al. (1990). "Expression in *Escherichia coli* of a High-Molecular-Weight Protective Surface Antigen Found in Nontypeable and Type B Haemophilus influenzae," Infect. & Immun. 58: 1909-191.
Thumm, G. et al. (1997). "Studies on Prolysostaphin Processing and Characterization of the Lysostaphin Immunity Factor (Lit) of *Staphylococcus* simulans Biovar Staphylolyticus," Molecular Microbiology 23(6):1251-1265.
Tiozzo, E. et al. (1998). "Wide-Spectrum Antibiotic Activity of Synthetic, Amphipathic Peptides," Biochem. & Biophys. Res. Comm 249(1):202-206.
Tokmakov et al. (1 997). "Inhibition of MAPK Pathway by a Synthetic Peptide Corresponding to the Activation Segment of MAPK," Biochem. Biophys. Res. Comm 252:214-219.

(56) References Cited

OTHER PUBLICATIONS

Tokmakov et al. (1997)."Phosphorylation-Sensitive Secondary Structure in a Synthetic Peptide Corresponding to the Activation Loop of MAP Kinase," Biochem. Biophys. Res. Commun. 236:243-247.
Tortosa, P. et al (Mar. 2000). "Characterisation of ylbF, a New Gene Involved in Competence Development and Sporulation in Bacillus subtilis," Molecular Microbiology 35(5) : 11 10-1 119.
Tripet et al. (1997). "Demonstration of Coiled-Coli Interactions Within the Kinesin Neck Region Using Synthetic Peptides," J. Biol. Chem. 272:8946-8956.
Tsai et al (2000) "Anatomy of Protein Structures: Visualizing How a One-Dimensional Protein Chain Folds into a Three-Dimensional Shape" PNAS, 97:12038-12043.
Urbanek, M. et al. (Jan. 2003). "Variation in Resistin Gene Promoter Not Associated With Polycystic Ovary Syndrome," Diabetes 52: 214-2 17.
Valentini, S.R. et al (Feb. 1994). "Glucocorticoid-Regulated Gene in Transformed to Normal Phenotypic Reversion," Brazilian J Med Biol Res 27(2): 541-546.
Van Regenmortel M.H.V. (1989). "Structural and Functional Approaches to the Study of Protein Antigenicity," Immunology Today 10:266-272.
Vidal et al. (1999). "Yeast Forward and Reverse In1 -hybrid Systems," Nucl. Acids Res. 27:919-929.
Vranken et al. (2002). "Solution Structures of a 30-Residue Amino-Terminal Domain of the Carp Granulin-1 Protein and its Amino-Terminally Truncated 3-30 Subfragment: Implications for the Conformational Stability of the Stack of Two O-Hairpins," Proteins 47: 14-24.
Waddell et al (2001) "A 'non-hybrids' screen for functional antagonizers of human p53 transactivator function: dominant negativity in fission yeast" *Oncogene* 20:6001-6008.
Wang, et al., PISCES: recent improvement to a PDB sequence culling server, Nucleic acid research. vol. 33, W94-W98, 2005.
Wang, et al., Predicting protein secondary structure be a support vector machine based on a new coding scheme, Genome Informatics, 15(2): 181-190 (2004).
Watt P (2006) "Screening for peptide drugs from the nature repertoire of biodiverse protein folds" Nature Biotechnology, 24(2):177-183.
Wigler et al. (1980). "Transformation of Mammalian Cells with an Amplifiable Dominant-Acting Gene," Proc. Natl. Acad. Sci. USA 77:3567-3570.
Wittrup, K.D. (2001). "Protein Engineering by Cell-Surface Display," Current Opinion in Biotechnology 12:395-399.
Wong, et al. (1996). "Use of Tagged Random Hexamer Amplification (TRHA) to Clone and Sequence Minute Quantities of DNA-Application to a 180 kb Plasmid Isolated From Sphingomonas F199," Nucleic Acids. Res. 24:3778-3783.
Xu et al. (2001). "Dominant Effector Genetics in Mammalian Cells," Nature Genetics 27:23-29.
Xu et al. (Nov. 1997). "Cells That Register Logical Relationships Among Proteins," Proc. Natl. Acad. Sci. USA 94: 12473-12478.
Yang (1999). "Cloning, Expression, and Characterization of a DNA Binding Domain of gpNul, a Phage h DNA Packaging Protein," Biochem. 38:465-477.
Yang et al. (1998). "A 20-Kilodalton N-Terminal Fragment of the D15 Protein Contains a Protective Epitope(s) Against Haemophilus influenzae Type A and Type B," Infect. and Immun. 66:3349-3354.
Yang et al. (2000). "An Integrated Approach to the Analysis and Modeling of Protein Sequences and Structures. 111. A Comparative Study of Sequence Conservation in Protein Structural Families using Multiple Structural Alignments," J. Mol. Biol. 301:691-711.
Yang, P. et al (Dec. 17, 1999). "Direct Activation of the Fission Yeast PAK Shkl by the Novel SH3 Domain Protein, Skb5," The Journal of Biological Chemistry 274(51): 36052-36057.
Yao, S. et al. (1998). "Uncoiling c-Jun Coiled Coils. Inhibitory Effects of Truncated Fos Peptides on Jun Dimerization and DNA binding in Vitro" Biopolymers 47(4):277-283.
Yao, S.Q. et al. (1997). "Inhibiting Dimerization and DNA Binding of c-Jun," In Peptides: Frontiers of Peptide Science,Proceedings of the 15th Amernican Peptide Symposium, Nashville, TN, Jun. 14-19, 1997, Tam, J.P. et al. eds. Kluwer Academic Publishers, Dordrecht.
Yasueda et al. (1996). "Species-Specific Measurement of the Second Group of Dermatophagoides Mite Allergens, Der p 2 and Der f 2, Using a Monoclonal Antibody-based ELISA," Clin. Exp. Allergy. 26:171-177.
Young, K.H. (1998). "Yeast Two-Hybrid: So Many Interactions, (in) so Little Time," Biology of Reproduction 58:302-311.
Zhang et al. (1992). "Whole Genome Amplification From a Single Cell: Implications for Genetic Analysis," Proc. Natl. Acad. Sci. USA 895847-5851.
Zhou, J.M. et al. (2002). "A Novel Strategy by the Action of Ricin that Connects Phenotype and Genotype Without Loss of the Diversity of Libraries," J. Am. Chem. Soc. 124(4):538-543.
Zhou, X-F. et al. (Feb. 1999). "Ligand-Activated Retinoic Acid Receptor Inhibits AP-1 Transactivation by Disrupting c-Junlc-Fos Dimerization," Mol. Endocrin. 13(2):276-285.
Kimball's Biology Pages, "Genome Sizes", (located on-line at users. rcn.com/jkimball.ma.ultranet/BiologyPages/G/GenomeSizes.html), 2013, 3 pages.
Importance of Mouse Genome, "Why Mouse Matters", National Human Genome Research Institute, (located on-line at www.genome.gov/10001345) 2010, 1 page.

METHODS OF CONSTRUCTING AND SCREENING LIBRARIES OF PEPTIDE STRUCTURES

RELATED APPLICATION DATA

This application claims priority from Australian Patent Application No. 2006900864 filed on Feb. 20, 2006, the contents of which are incorporated herein in their entirety.

FIELD OF THE INVENTION

The present invention relates to libraries and databases of structural peptides and methods for producing and/or screening same.

SEQUENCE LISTING

The present specification incorporates by reference in its entirety the Sequence Listing, which is provided as duplicate electronic associated files, each filed concurrently herewith and named "Copy_1_131467_sequence_listing_ST25.txt" and "Copy_2_131467_sequence_listing_ST25.txt". Each of these associated files was created on Feb. 6, 2007 and is 10,134 KB in size. This sequence information was prepared using PatentIn Version 3.3. Each sequence is identified in the sequence listing by the numeric indicator <210> followed by the sequence identifier (e.g. <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Sequences referred to in the sequence listing are defined by the term "SEQ ID NO:", followed by the sequence identifier (e.g. SEQ ID NO: 1 refers to the sequence in the sequence listing designated as <400>1).

General

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts that are incorporated by reference:

(i) J. F. Ramalho Ortigão, "The Chemistry of Peptide Synthesis" In: Knowledge database of Access to Virtual Laboratory website (Interactiva, Germany);

(ii) Sakakibara. D., Teichman, J., Lien, E. Land Fenichel. R. L. (1976). *Biochem. Biophys. Res. Commun.* 73 336-342

(iii) Merrifield. R. B. (1963). *J. Am. Chem. Soc.* 85, 2149-2154.

(iv) Barmy, G. and Merrifield. R. B. (1979) in *The Peptides* (Gross. E. and Meienhofer. J. eds.), vol. 2, pp. 1-284. Academic Press, New York.

(v) Wunsch. E., ed. (1974) *Synthese von Peptiden in Houben-Weyls Metoden der Organischen Chemie* (Müller, E., ed.). vol. 15, 4th edn., Parts 1 and 2. Thieme. Stuttgart.

(vi) Bodanszky. M. (1984) *Principles of Peptide Synthesis*, Springer-Verlag, Heidelberg.

(vii) Bodanszky. M. & Bodanszky, A. (1984) *The Practice of Peptide Synthesis, Springer-Verlag*, Heidelberg.

(viii) Bodanszky. M. (1985) *Int. J. Peptide Protein Res.* 25, 449-474.

BACKGROUND OF THE INVENTION

Description of the Related Art

The majority of biological processes in living organisms are mediated by proteins and their interactions with specific ligands e.g., other proteins, antigens, antibodies, nucleic acids, lipids and carbohydrates. Not only are such interactions involved in normal biological processes, protein interactions are also causative of processes involved in diseases or disorders. As a consequence, protein interactions are important targets for the development of new therapeutic compounds.

To identify suitable therapeutic compounds, the pharmaceutical industry has particularly focussed on screening processes to identify small molecule compounds capable of interacting with a protein and/or inhibiting a protein interaction. To function as a drug suitable for administration to a subject a small molecule must be capable of binding to a target with high affinity and selectivity.

Often, small molecules and short peptides do not effectively modulate protein interactions because they do not generally possess a required shape e.g., to fit into complex protein surfaces or bind to relatively featureless interfaces. As a consequence, small-molecules ands short peptides are generally unable to bind to many surfaces of a target protein with sufficiently-high affinity and specificity to modulate binding of a ligand to the target, or to otherwise agonize or antagonize the activity of the target protein. Accordingly, there is a high attrition rate for the screening of such molecules as drug leads for therapeutic applications, particularly for targets such as protein interactions.

By way of example, notwithstanding that short random peptides may be sufficiently small for commercial i.e., large-scale production by chemical synthesis, they generally provide highly-variable bioactivities against target proteins, and interactions with their targets are generally low affinity interactions. For example, in a screen of a random peptide library to identify a peptide capable of dissociating HIV protease fewer than about $1 \times 10^{-6}$ peptides displayed the desired activity (Park and Raines Nat. Biotechnol., 18: 548-550, 2000). This low "hit" rate appears to be a result of the inability of the such random peptides to assume stable secondary structure and/or tertiary structure to thereby facilitate binding to a target protein.

In response to the low "hit" rate for identifying new drug leads, the pharmaceutical industry has expended some effort in developing synthetic scaffolds for presenting ligands to proteins, with a view to modulating activity of the target protein. However, such constraint of random peptide libraries has failed to increase the "hit" rate for identifying new drug candidates based on random peptide sequences to a level that makes peptides a viable alternative to small molecules. For example, random peptides have been constrained within scaffold structures e.g., the active site loop of thioredoxin ("Trx"; Colas et al., Nature, 380: 548-550, 1996) and tested for binding to cyclin-dependent kinase-2 (Cdk-2), however fewer than $2 \times 10^{-5}$ of the Trx-constrained peptides actually blocked the target. Thus, the provision of synthetic scaffolds does not necessarily enhance "hit" rate. It is also possible that the limited repertoire of artificial scaffolds available to the industry will necessarily limit the diversity of structures that can be produced using such approaches, and may even mask or modify any native structures formed.

Native proteins have considerable structural features, including protein "domains" that are generally of functional significance. Until the present invention, such structural features have largely been utilized to determine evolutionary relationships between proteins, and for dissecting dynamic folding, pathways i.e., how particular proteins fold. For example, the CATH database (Orengo et al., Structure 5, 1093-1108, 1997) classifies proteins according to a hierarchy of Class, Architecture, Topology and Homologous superfamily based upon structure, sequence, and functional considerations. In particular, the CATH hierarchy acknowledges three basic structural features i.e., class, architecture and topology. Protein "class" is highest in the CATH hierarchy and, in this context is a reference to the secondary structure composition and packing of a protein i.e., mainly $\alpha$-helix, mainly $\beta$-strand, and $\alpha$–$\beta$ including alternating $\alpha/\beta$ in which the secondary structures alternate along the protein chain, and $\alpha+\beta$ in which the $\alpha$ and $\beta$ regions are largely segregated. Thus, the "class" to which a protein belongs is a global assignment based on secondary structure considerations. Protein "architecture" refers to the overall shape of a protein based upon groups of similar secondary structural arrangements irrespective of the order in which they are connected in the protein. Protein "topology" describes the relative associations and orientations of secondary structures in 3D and the order in which they are connected. Protein "folds" are recognized in the CATH hierarchy as a function of topology, however the literature is confusing in this respect, because a fold can adopt a specific architecture e.g., Orenao and Thornton. Ann. Rev. Biochem. 74, 867-900, 2005.

As used herein, the term "fold" is therefore taken in its broadest context to mean a tertiary structure formed by the folding of multiple secondary structures including aspects of both architecture and topology. Herein, the term "subdomain" is used interchangeably with the term "fold". A "fold" may form independently or in association with other parts of a protein or other proteins or a scaffold structure.

From a practical perspective, there are significant limitations in utilizing structure data for drug screening applications. For example, structure data are limited, especially when compared to the huge volumes of sequence data available. This is notwithstanding the recent developments of computational methods for obtaining source data consisting essentially of fold recognition and threading algorithm that provide specific sequence annotations PSI-BLAST or IMPALA (Muller et al., J. Mol. Biol. 293, 1257-1271, 1999; Buchan et al., Genome Res. 12, 503-514, 2002; J. Mol. Biol. 287, 797-815, 1999). Such methods are often of limited applicability for drug screening applications because the lengths of annotated sequences produced there from are often too long for practical applications, not being restricted to single folds and more often than not containing flanking sequences. More importantly, such annotated sequence data provides no indication of structural considerations outside the context of the native protein. This is partly due to the fact that these methods have been developed largely as research tools for determining evolutionary relationships between proteins and for assessing how individual proteins fold in nature. For example, Table 1 herein includes descriptions of segments of proteins comprising protein domains.

TABLE 1

Exemplary structures adopted by homologous superfamilies of proteins

| Class of secondary structure | Architecture and/or topology of folds within proteins |
|---|---|
| $\alpha$-helix | $\alpha$-helices; folded leaf, partly opened |
| $\alpha$-helix | 2$\alpha$-helices; antiparallel hairpin, left-handed twist |
| $\alpha$-helix | tandem repeat of two calcium-binding loop-helix motifs comprising $\alpha$--helices |
| $\alpha$-helix | helix-extended loop-helix; parallel $\alpha$-helices |
| $\alpha$-helix | 2$\alpha$-helices; one short, one long; aromatic-rich interface |
| $\alpha$-helix | 3$\alpha$-helices; folded leaf, opened |
| $\alpha$-helix | 3-$\alpha$-helices; bundle, closed or partly opened, right-handed twist; up-and down |
| $\alpha$-helix | 3-$\alpha$-helices; bundle, closed or partly opened, right-handed twist; up-and down |
| $\alpha$-helix | 3$\alpha$-helices; bundle, right-handed twist |
| $\alpha$-helix | 3-4$\alpha$-helices |
| $\alpha$-helix | 3$\alpha$-helices; architecture is similar to that of the "winged helix" fold |
| $\alpha$-helix | 3$\alpha$-helices; bundle, closed, left-handed twist; up-and-down |

TABLE 1-continued

Exemplary structures adopted by homologous superfamilies of proteins

| Class of secondary structure | Architecture and/or topology of folds within proteins |
|---|---|
| α-helix | 3α-helices; bundle, closed, left-handed twist; up-and-down; mirror topology to the spectrin-like fold |
| α-helix | 3α-helices; bundle, closed, right-handed twist; up-and-down |
| α-helix | 3α-helices; bundle, closed, left-handed twist, up-and-down |
| α-helix | core; 3α-helices; bundle, closed, left-handed twist; up-and-down |
| α-helix | 3α-helices; bundle, partly opened |
| α-helix | 3α-helices, the first one is shorter than the other two; bundle, partly opened |
| α-helix | 3 short α-helices; irregular array |
| α-helix | 3 short α-helices; irregular array |
| α-helix | 3α-helices; irregular array |
| α-helix | 3α-helices; irregular array; disulfide-rich |
| α-helix | α-helices; irregular array; disulfide-rich |
| α-helix | 3α-helices; irregular array |
| α-helix | 3α-helices; bundle, closed, right-handed twist; up-and-down |
| α-helix | 3α-helices; bundle, closed, left-handed twist; parallel |
| α-helix | 3α-helices; irregular array |
| α-helix | 3α-helices; long middle helix is flanked at each end with shorter ones |
| α-helix | 3α-helices; bundle, open |
| α-helix | α-helices; irregular array |
| α-helix | 4α-helices; bundle, closed or partly opened, left-handed twist; up-and-down |
| α-helix | 4α-helices; bundle, closed, right-handed twist; 1 crossover connection |
| α-helix | 4α-helices; bundle, closed, left-handed twist; 1 crossover connection |
| α-helix | 4α-helices; bundle, closed; left-handed twist; 2 crossover connections |
| α-helix | 4α-helices; bundle; one loop crosses over one side of the bundle |
| α-helix | 4α-helices, bundle; helix 3 is shorter than others; up-and-down |
| α-helix | 4α-helices; bundle; minor mirror variant of up-and-down topology |
| α-helix | 4α-helices; dimer of identical alpha-hairpin subunits; bundle, closed, left-handed twist |
| α-helix | 4α-helices; bundle, closed, right-handed twist |
| α-helix | 4α-helices; bundle, closed, right-handed twist |
| α-helix | 4α-helices; bundle, closed, right-handed twist |
| α-helix | 4α-helices; bundle, closed, left-handed twist |
| α-helix | 4α-helices; bundle, closed, right-handed twist |
| α-helix | 4α-helices; folded leaf, closed |
| α-helix | 4α-helices; orthogonal array |
| α-helix | 4α-helices; the long C-terminal helix protrudes from the domain and binds to DNA |
| α-helix | 4-α-helices; bundle, closed, left-handed twist; 2 crossover connections |
| α-helix | 4α-helices; array of 2 hairpins, opened |
| α-helix | 4α-helices; bundle |
| α-helix | 4α-helices; bundle |
| α-helix | 4α-helices; open bundle; capped by two small 3-stranded beta-sheets duplication: consists of two structural repeats |
| α-helix | 4α-helices; bundle; flanked by two short beta-hairpins duplication: consists of two structural repeats |
| α-helix | 4α-helices; array of 2 hairpins, opened |
| α-helix | 4 helices; bundle, closed, left-handed twist; right-handed super helix |
| α-helix | 4α-helices; bundle, left-handed twist; right-handed super helix |
| α-helix | 4α-helices; bundle, right-handed twist; right-handed super helix |
| α-helix | 4 long α-helices; bundle, left-handed twist (coiled coil); right-handed super helix |
| α-helix | 4α-helices; bundle, left-handed twist; left-handed super helix |
| α-helix | 4α-helices; bundle, right-handed twist; left-handed super helix |
| α-helix | 4α-helices; irregular array |
| α-helix | 2α-helices and adjacent loops |
| α-helix | 4α-helices; irregular array |
| α-helix | 4α-helices; irregular array |
| α-helix | 4α-helices; irregular array, disulfide-linked |
| α-helix | 4α-helices irregular array, disulfide-linked |
| α-helix | 4α-helices; irregular array, disulfide-linked |
| α-helix | 4α-helices; folded leaf; right-handed super helix |
| α-helix | 4α-helices; folded leaf; right-handed super helix |
| α-helix | 4α-helices; bundle |
| α-helix | 4 long α-helices; bundle |
| α-helix | 4 helices; bundle, partly opened |
| α-helix | core; 4α-helices; bundle, partly opened, capped with a beta-sheet |
| α-helix | 4α-helices, bundle |
| α-helix | 4 helices; the three last helices form a bundle similar to that of the RuvA C-domain |
| α-helix | 4α-helices; an orthogonal array |
| α-helix | 4α-helices; an orthogonal array |
| α-helix | 4α-helices; up-and-down bundle |
| α-helix | 4α-helices; open up-and-down bundle; binds alpha-helical peptides |
| α-helix | 4α-helices; open up-and-down bundle; flexible N-terminal tail |

TABLE 1-continued

Exemplary structures adopted by homologous superfamilies of proteins

| Class of secondary structure | Architecture and/or topology of folds within proteins |
|---|---|
| α-helix | 4α-helices; array |
| α-helix | 4α-helices; bundle, closed, left-handed twist |
| α-helix | 4α-helices dimer of identical alpha-hairpin subunits; open bundle |
| α-helix | 4-5α-helices; bundle of two orthogonally packed alpha-hairpins |
| α-helix | 4-5α-helices; right-handed super helix |
| α-helix | 5α-helices; right-handed super helix; swapped dimer with the two long C-terminal helices |
| α-helix | α-helices array; two long helices form a hairpin that dimerizes into a 4-helical bundle |
| α-helix | 5α-helices; bundle, closed, left-handed twist |
| α-helix | 5α-helices; bundle, closed, left-handed twist |
| α-helix | 5α-helices; bundle, closed, left-handed twist; helices 2-5 adopt the Four-helical up-and-down bundle fold |
| α-helix | 5α-helices; bundle, closed, left-handed twist |
| α-helix | 5α-helices; folded leaf, closed |
| α-helix | 5α-helices; folded leaf, closed |
| α-helix | 5α-helices; folded leaf |
| α-helix | 5α-helices; irregular array; left-handed super helix |
| α-helix | 4-5α-helices; bundle; left-handed super helix |
| α-helix | 5α-helices; bundle |
| α-helix | 5α-helices; bundle |
| α-helix | α-helices; bundle |
| α-helix | 5α-helices; bundle |
| α-helix | α-helices; one helix is surrounded by the others |
| α-helix | 5α-helices; one helix is surrounded by the others |
| α-helix | 5α-helices; one helix is surrounded by the others |
| α-helix | 5α-helices; contains one more helix and a beta-hairpin outside the core |
| α-helix | 5α-helices; bundle |
| α-helix | α-helical bundle; up-and-down; right-handed twist |
| α-helix | 5α-helices; orthogonal array |
| α-helix | 5α-helices; orthogonal array |
| α-helix | 5α-helices; irregular array |
| α-helix | 5α-helices; array |
| α-helix | 5α-helices; orthogonal array; folding similarity to the TipA-S domain |
| α-helix | 5α-helices; array |
| α-helix | 6α-helices; bundle; left-handed twist, up-and-down topology |
| α-helix | 6α-helices, homodimer of 3-helical domains |
| α-helix | 6α-helices, homodimer of 3-helical domains |
| α-helix | 6α-helices, homodimer of 3-helical domains |
| α-helix | 6α-helices, heterodimer of 3-helical domains |
| α-helix | dimer of 3α-helical segments; consists of two subdomains; 4-helical bundle and coiled coil |
| α-helix | 6α-helices; closed bundle; greek-key; internal pseudo twofold symmetry |
| α-helix | 6α-helices; closed bundle; greek-key; internal pseudo twofold symmetry |
| α-helix | 6α-helices; bundle; one central helix is surrounded by 5 others |
| α-helix | 6α-helices; bundle; one central helix is surrounded by 5 others |
| α-helix | 6α-helices; array |
| α-helix | 6α-helices; orthogonal array |
| α-helix | irregular array of 6 short α-helices |
| α-helix | 6α-helices; one central helix is surrounded by 5 others |
| α-helix | 6α-helices; one central helix is surrounded by 5 others |
| α-helix | 6α-helices; bundle; one central helix is surrounded by 5 others |
| α-helix | Multiple α-helices |
| α-helix | Multihelical; core; 5-helical bundle |
| α-helix | multihelical; contains compact array of 6 short helices |
| α-helix | multihelical; irregular array of long and short helices |
| α-helix | multihelical; irregular array of long and short helices |
| α-helix | multihelical bundle; contains buried central helix |
| α-helix | multihelical; contains two buried central helices |
| α-helix | multihelical; can be divided into two subdomains |
| α-helix | multihelical; consists of two all-alpha subdomains contains a 4-helical bundle with left-handed twist and up-and-down topology |
| α-helix | multihelical; consists of two all-alpha subdomains each containing a 3-helical bundle with right-handed twist |
| α-helix | multihelical; consists of two all-alpha subdomains; contains a 4-helical bundle with left-handed twist and up-and-down topology |
| α-helix | multihelical; consists of two tightly associated 3-helical bundles with different twists |
| α-helix | multihelical; consists of two all-alpha subdomains; dimer |
| α-helix | multihelical; consists of two all-alpha subdomains |
| A-helix | multihelical; consists of two all-alpha domains |
| A-helix | multihelical; consists of two different 3-helical domains connected by a long, partly helical linker |

TABLE 1-continued

Exemplary structures adopted by homologous superfamilies of proteins

| Class of secondary structure | Architecture and/or topology of folds within proteins |
|---|---|
| α-helix | multihelical; consists of two different alpha-helical bundles (4-helical and 3-helical) |
| α-helix | multihelical; consists of two different alpha-helical bundles |
| α-helix | multihelical; consists of two different alpha-helical bundles |
| α-helix | multihelical; consists of two different all-alpha subdomains, 4 helices each |
| α-helix | multihelical; consists of two all-alpha domains |
| α-helix | multihelical; consists of two all-alpha domains |
| α-helix | multihelical; consists of two all-alpha subdomains |
| α-helix | multihelical consists of two all-alpha subdomains subdomain 1 (residues 10-100) is a 4-helical bundle |
| α-helix | multihelical |
| α-helix | multihelical; consists of two all-alpha subdomains |
| α-helix | multihelical; common core is formed around two long antiparallel helices related by (pseudo) twofold symmetry |
| α-helix | multihelical |
| α-helix | multihelical; up to seven alpha-hairpins are arranged in closed circular array |
| α-helix | multihelical; consists of two all-alpha domains |
| α-helix | multihelical |
| α-helix | multihelical; forms intertwined dimer of identical 5-helical subunits |
| α-helix | multihelical; intertwined tetramer |
| α-helix | multihelical; intertwined trimer of identical 3-helical subunits |
| α-helix | multihelical; consists of two all-alpha domains |
| α-helix | multihelical; core; 5-helical bundle; binds cofactor at the beginning of third helix |
| α-helix | multihelical; contains a 3-helical bundle surrounded by several shorter helices |
| α-helix | multihelical; contains a 3-helical Hin recombinase-like subdomain and two long dimerisation helices |
| α-helix | multihelical oligomeric protein |
| α-helix | multihelical; consists of a conserved 4-helical core and a variable insert subdomain |
| α-helix | multihelical; consists of 2 all-alpha subdomains |
| α-helix | multihelical; consists of 2 all-alpha subdomains, "rigid" one and "mobile" one |
| α-helix | multihelical; consists of 2 all-alpha subdomains connected by a long helix |
| α-helix | multihelical; array of longer and shorter helices; contains an alpha-hairpin dimerisation subdomain |
| α-helix | multihelical; bundle of longer and shorter helices |
| α-helix | multihelical; three-helical bundle in the core is surrounded by non-conserved helices |
| α-helix | multihelical; consists of two subdomains |
| α-helix | multihelical |
| α-helix | multihelical |
| α-helix | multihelical; can be divided into an alpha-alpha super helix domain and a long alpha-hairpin dimerization domain |
| α-helix | multihelical; can be divided into three subdomains (neck, body and tail) |
| α-helix | multihelical; 2 (curved) layers; alpha/alpha; right-handed super helix |
| α-helix | multihelical |
| α-helix | multihelical; consists of two all-alpha subdomains |
| α-helix | multihelical; interlocked (homo)dimer |
| α-helix | multihelical; interlocked heterodimer with F-box proteins |
| α-helix | multihelical; interlocked heterodimer with the Skp1 dimerisation domain |
| α-helix | multihelical; 3 layers or orthogonally packed helices |
| α-helix | multihelical |
| α-helix | multihelical; consist of two subdomains |
| α-helix | multihelical; open array |
| α-helix | multihelical; 2 layers or orthogonally packed helices |
| α-helix | multihelical bundle; contains buried central helix |
| α-helix | multihelical; consists of two topologically similar alpha-helical bundles |
| α-helix | multihelical; consists of 2 four-helical bundles |
| α-helix | multihelical; one domain consists of two similar disulfide-linked subdomains |
| α-helix | multihelical, consists of three all-alpha domains |
| α-helix | multihelical, consists of three all-alpha domains |
| α-helix | multihelical; core; 8 helices (C-J) are arranged in 2 parallel layers |
| α-helix | multihelical; 8 helices arranged in 2 parallel layers |
| α-helix | multihelical; bundle |
| α-helix | multihelical; core; 6 helices, bundle |
| α-helix | multihelical; forms a boat-shaped protein shell around cofactors |
| α-helix | multihelical; bundle |
| α-helix | multihelical; contains 4-helical bundle and 2-helical arm |
| α-helix | multihelical; array |
| α-helix | multihelical; array |
| α-helix | multihelical; bundle |
| α-helix | multihelical; bundle |
| α-helix | multihelical; bundle |
| α-helix | multihelical; array |

TABLE 1-continued

Exemplary structures adopted by homologous superfamilies of proteins

| Class of secondary structure | Architecture and/or topology of folds within proteins |
|---|---|
| α-helix | common core; 2 helices, disulfide-linked, and a calcium-binding loop |
| α-helix | 5 helices; irregular disulfide-linked array; also contains a small beta-hairpin |
| α-helix | 5 helices; irregular disulfide-linked array; form homodimer |
| α-helix | 5 helices; irregular disulfide-linked array; topological similarity to the Fungal elicitin fold |
| α-helix | 6 helices; irregular non-globular array; also contains two small b-hairpins |
| α-helix | 3 helices, non-globular array; forms interlocked heterodimers with its targets |
| α-helix | variable number of helices and little beta structure |
| β-sheet | sandwich; 7 strands in 2 sheets; greek-key |
| β-sheet | sandwich; 9 strands in 2 sheet; greek-key; subclass of immunoglobin-like fold |
| β-sheet | sandwich; 7 strands in 2 sheets, greek-key |
| β-sheet | sandwich; 6 strands in 2 sheets |
| β-sheet | sandwich; 6 strands in 2 sheets |
| β-sheet | sandwich; 6 strands in 2 sheets |
| β-sheet | six-stranded beta-sandwich, jelly-roll/greek-key topology |
| β-sheet | sandwich; 7 strands in 2 sheets, greek-key |
| β-sheet | sandwich; 7 strands in 2 sheets, greek-key; permutation of the immunoglobulin-like fold |
| β-sheet | sandwich; 8 strands in 2 sheets; greek-key |
| β-sheet | sandwich; 8 strands in 2 sheets; greek-key |
| β-sheet | sandwich; 8 strands in 2 sheets; meander |
| β-sheet | sandwich; 8 strands in 2 sheets; meander |
| β-sheet | sandwich; 8 strands in 2 sheets; jelly-roll; some members can have additional 1-2 strands |
| β-sheet | sandwich; 8 strands in 2 sheets; greek-key |
| β-sheet | sandwich; 8 strands in 2 sheets; complex topology |
| β-sheet | sandwich; 8 strands in 2 sheets; jelly-roll |
| β-sheet | sandwich; 8 strands in 2 sheets; jelly-roll; similarity to the Nucleoplasmin-like/VP fold |
| β-sheet | sandwich; 8 strands in 2 sheets; jelly-roll |
| β-sheet | sandwich; 8 strands in 2 sheets; jelly-roll |
| β-sheet | sandwich; 8 strands in 2 sheets; greek-key |
| β-sheet | beta-sandwich; 8 strands in 2 sheets |
| β-sheet | sandwich; 8 strands in 2 sheets; complex topology with the crossing loops |
| β-sheet | sandwich; 8 strands in 2 sheets; greek-key; partial topological similarity to immunoglobulin-like folds |
| β-sheet | sandwich; 8 strands in 2 sheets; greek-key; partial topological similarity to immunoglobulin-like folds |
| β-sheet | sandwich; 8 strands in 2 sheets; greek-key; partial topological similarity to immunoglobulin-like folds |
| β-sheet | sandwich; 9 strands in 2 sheets; jelly-roll |
| β-sheet | sandwich; 9 strands in 2 sheets; jelly-roll; form trimers |
| β-sheet | sandwich; 9 strands in 2 sheets; greek-key |
| β-sheet | sandwich; 9 strands in 2 sheets; greek-key |
| β-sheet | sandwich; 9 strands in 2 sheets; greek-key/jelly-roll |
| β-sheet | sandwich; 9 strands in 2 sheets; jelly-roll |
| β-sheet | sandwich; 9 strands in 2 sheets; greek-key; contains a few helices in loop regions |
| β-sheet | sandwich; 9 strands in 2 sheets; unusual topology with 2 crossover loops |
| β-sheet | sandwich, 10 strands in 2 sheets; greek-key |
| β-sheet | sandwich, 10 strands in 2 sheets; jelly-roll |
| β-sheet | sandwich, 10 strands in 2 sheets; jelly-roll |
| β-sheet | sandwich, 10 strands in 2 sheets; "folded meander" |
| β-sheet | sandwich, 10 strands in 2 sheets |
| β-sheet | sandwich; 11 strands in 2 sheets |
| β-sheet | sandwich; 11 strands in 2 sheets; greek-key |
| β-sheet | sandwich; 11 strands in 2 sheets; greek-key |
| β-sheet | sandwich; 14 strands in 2 sheets; greek-key |
| β-sheet | sandwich; 12-14 strands in 2 sheets; complex topology |
| β-sheet | sandwich; 18 strands in 2 sheets |
| β-sheet | duplication: two beta-sandwiches of similar topologies are fused together in a single three beta-sheet domain |
| β-sheet | consists of two beta-sandwich domains of similar topologies |
| β-sheet | consists of two different beta-sandwich domains of partial topological similarity to immunoglobulin-like folds |
| β-sheet | consists of two different beta-sandwich domains unrelated to other beta-sandwich folds |
| β-sheet | consists of two all-beta subdomains; conserved small domain has a rubredoxin-like fold; larger domain consists of 6 beta-stands packed in either sandwich of two 3-stranded sheets or closed barrel (n = 6; S = 8) |
| β-sheet | this fold is formed by three glycine-rich regions inserted into a small 8-stranded beta-sandwich |
| β-sheet | barrel, partly opened; $n^* = 4$, $S^* = 8$; meander |
| β-sheet | contains barrel, partly opened; $n^* = 4$, $S^* = 8$; meander |

TABLE 1-continued

Exemplary structures adopted by homologous superfamilies of proteins

| Class of secondary structure | Architecture and/or topology of folds within proteins |
|---|---|
| β-sheet | contains barrel, partly opened; n* = 4, S* = 8; meander; capped by alpha-helix |
| β-sheet | core; barrel, in some members open; n* = 4, S* = 8; meander |
| β-sheet | core; barrel, open; n* = 4, S* = 8; meander; SH3-like topology |
| β-sheet | core; barrel, open; n* = 4, S* = 8; meander; SH3-like topology; some similarity to the Sm-like fold |
| β-sheet | core; barrel, open; n* = 4, S* = 8; meander; SH3-like topology; some similarity to the Sm-like fold |
| β-sheet | core; barrel, closed; n = 4, S = 8; complex topology; helix-containing crossover connection |
| β-sheet | barrel, closed; n = 5, S = 8, meander |
| β-sheet | barrel, closed or partly opened n = 5, S = 10 or S = 8; greek-key |
| β-sheet | core; barrel, partly opened; n* = 5, S* = 8; meander |
| β-sheet | barrel, closed; n = 6, S = 12; and a hairpin triplet; meander |
| β-sheet | barrel, closed; n = 6, S = 10; greek-key |
| β-sheet | barrel, closed; n = 6, S = 10; greek-key |
| β-sheet | barrel; n = 6, S = 10; greek-key |
| β-sheet | core; barrel; n = 6, S = 10; greek-key; topologically similar to the FMN-binding split barrel |
| β-sheet | segment-swapped dimer forming two identical conjoint barrels (n = 6, S = 10) topologically similar to the FMN-binding split barrel |
| β-sheet | barrel, open; n* = 6, S* = 10; greek-key |
| β-sheet | barrel, closed; n = 6, S = 8; greek-key |
| β-sheet | barrel; n = 6, S = 8, greek-key; similar to one trypsin-like protease barrel |
| β-sheet | barrel; n = 6, S = 8, greek-key |
| β-sheet | barrel, closed; n = 6, S = 8; greek-key |
| β-sheet | barrel, closed; n = 6, S = 8, greek-key, partial similarity to the OB-fold |
| β-sheet | barrel, closed; n = 6, S = 10, complex topology |
| β-sheet | core; barrel, closed; n = 6, S = 8; topology is similar to that of the acid proteases barrel |
| β-sheet | barrel, closed; n = 6, S = 8; a crossover loop topology |
| β-sheet | barrel, closed; n = 6, S = 10; complex topology with crossover (psi) loops |
| β-sheet | barrel, closed; n = 6, S = 10; complex topology |
| β-sheet | barrel, closed; n = 6, S = 10; meander; capped at both ends by alpha-helices |
| β-sheet | barrel, partly opened; n* = 6, S* = 12; meander; capped by an alpha-helix |
| β-sheet | barrel, closed; n = 6, S = 12; mixed beta-sheet |
| β-sheet | core; barrel, closed; n = 7, S = 8; complex topology |
| β-sheet | barrel, closed; n = 7, S = 10; complex topology |
| β-sheet | barrel, closed; n = 7, S = 10; order; 1234765; strands 1 and 5 are parallel to each other |
| β-sheet | barrel, closed; n = 7, S = 10; complex topology |
| β-sheet | barrel, closed; n = 7, S = 10; greek-key topology; one overside connection |
| β-sheet | barrel, closed; n = 7, S = 10; complex topology |
| β-sheet | core; barrel, closed; n = 7, S = 12; meander |
| β-sheet | barrel, closed or opened; n = 8, S = 12; meander |
| β-sheet | barrel, closed; n = 8, S = 10; meander |
| β-sheet | barrel, closed; n = 8, S = 10; complex topology |
| β-sheet | barrel, closed; n = 8, S = 10; one overside connection |
| β-sheet | barrel, closed; n = 8, S = 10; mixed sheet; two overside connections |
| β-sheet | barrel, partly open; n* = 8, S* = 10; one psi loop |
| β-sheet | dimer of two non-identical subunits; forms two similar barrels, n = 8, S = 10 each, that are fused together with the formation of third barrel, n = 6, S = 8 |
| β-sheet | consists of four 4-stranded beta-sheet motifs; meander |
| β-sheet | consists of five 4-stranded beta-sheet motifs; meander |
| β-sheet | consists of six 4-stranded beta-sheet motifs; meander |
| β-sheet | consists of seven 4-stranded beta-sheet motifs; meander |
| β-sheet | consists of eight 4-stranded beta-sheet motifs; meander |
| β-sheet | folded sheet; greek-key |
| β-sheet | core; 3-stranded meander beta-sheet |
| β-sheet | small mixed beta-sheet, 4 "generalized" strands |
| β-sheet | coiled antiparallel beta-sheet of 5 strands, order 51324; complex topology, crossing loops |
| β-sheet | twisted meander beta-sheet of 6 strands |
| β-sheet | core; twisted 7-stranded beta-sheet (half-barrel) of complex topology |
| β-sheet | core; twisted 7-stranded beta-sheet (half-barrel) |
| β-sheet | single sheet; 10 strands |
| β-sheet | 11 stranded sheet partly folded in a corner-like structure filled with a few short helices |
| β-sheet | single sheet; 16 strands; meander |
| β-sheet | single sheet formed by beta-hairpin repeats; exposed on both sides in the middle |
| β-sheet | consists of 3 4-stranded sheets; strands are parallel to the 3-fold axis |
| β-sheet | consists of 3 4-stranded sheets; strands are perpendicular to the 3-fold axis |
| β-sheet | superhelix turns are made of parallel beta-strands and (short) turns |
| β-sheet | superhelix turns are made of parallel beta-strands and (short) turns |

TABLE 1-continued

Exemplary structures adopted by homologous superfamilies of proteins

| Class of secondary structure | Architecture and/or topology of folds within proteins |
|---|---|
| β-sheet | one turn of helix is made by two pairs of antiparallel strands linked with short turns |
| β-sheet | (homo)trimer; each chain donates 3 beta-strands per turn of the helix |
| β-sheet | trimer formed by the interlocking beta-hairpin repeat units |
| β-sheet | trimer; contains two different beta-prism-like domains connected by an linker subdomain of less regular structure |
| β-sheet | Trp-rich beta-hairpin repeat units form helical structures of 3 units per turn |
| β-sheet | sandwich of half-barrel shaped beta-sheets |
| β-sheet | double-stranded ribbon sharply bent in two places; the ribbon ends form incomplete barrel; jelly-roll |
| β-sheet | multisheet protein with a mixture of beta-sandwich and beta-prism features |
| β-sheet | multisheet protein containing partial beta-propeller and beta-sandwich regions |
| β-sheet | multisheet protein with a mixture of beta-sandwich and beta-barrel features |
| β-sheet | complex fold made of five beta-hairpin units and a b-ribbon arc |
| β-sheet | complex fold made of several coiled beta-sheets; contains an SH3-like barrel |
| β-sheet | complex fold made of several coiled beta-sheets |
| β-sheet | complex fold made of several coiled beta-sheets |
| β-sheet | complex fold |
| β-sheet | complex fold; consists of two intertwined subdomains |
| β-sheet | complex fold |
| β-sheet | complex fold made of bifurcated and partly folded beta-sheet |
| β-sheet | complex fold made of bifurcated and coiled beta-sheets |
| β-sheet | complex fold made of bifurcated and coiled b-sheets |
| β-sheet | pseudobarrel; mixed sheet of 7 strand folded upon itself and "buckled" by two beta-turns |
| β-sheet | pseudobarrel; sandwich of two sheets packed at a positive interstrand angle and interconnected with many short turns |
| β-sheet | pseudobarrel; capped on both ends by alpha-helices |
| β-sheet | pseudobarrel; capped at one end by an alpha-helix |
| β-sheet | pseudobarrel; capped on both ends by alpha-helices |
| β-sheet | pseudobarrel; mixed folded sheet of 5 strands; order 13452; strand 1 and 3 are parallel to each other |
| β-sheet | pseudobarrel; some similarity to OB-fold |
| β-sheet | non-globular proline-rich hairpin |
| α/β | contains parallel beta-sheet barrel, closed; n = 8, S = 8; strand order 12345678 |
| α/β | core; 3 layers; a/b/a; parallel beta-sheet of 6 strands, order 321456 |
| α/β | core; 3 layers; b/b/a; central parallel beta-sheet of 5 strands, order 32145; top antiparallel beta-sheet of 3 strands, meander |
| α/β | 3 layers; a/b/a; parallel beta-sheet of 5 strands, order 32145; Rossmann-like |
| α/β | 3 layers; a/b/a; parallel beta-sheet of 5 strands, order 32145; incomplete Rossmann-like fold; binds UDP group |
| α/β | variant of beta/alpha barrel; parallel beta-sheet barrel, closed, n = 7, S = 8; strand order 1234567; some members may have fewer strands |
| α/β | contains; barrel, closed; n = 10, S = 10; accommodates a hairpin loop inside the barrel |
| α/β | 3 layers; b/b/a; the central sheet is parallel, and the other one is antiparallel; there are some variations in topology |
| α/β | 2 layers; a/b; parallel beta-sheet of 3 strands, order 123 |
| α/β | core; 3 layers; a/b/a; parallel beta-sheet of 4 strands, order 1234; structural similarity of the MurF and HprK extends beyond the core. |
| α/β | 2 curved layers; a/b; parallel beta-sheet; order 1234 . . . N; there are sequence similarities between different superfamilies |
| α/β | core; three turns of irregular (beta-beta-alpha)n superhelix |
| α/β | core; 4 turns of a (beta-alpha)n superhelix |
| α/β | core; 4 turns of (beta-beta-alpha)n superhelix |
| α/β | 3 layers; a/b/a; core; parallel beta-sheet of 4 strands, order 2134 |
| α/β | 3 layers; a/b/a; core; parallel beta-sheet of 4 strands, order 2134 |
| α/β | 3 layers; a/b/a; core; parallel beta-sheet of 4 strands, order 2134 |
| α/β | 3 layers; a/b/a; core; parallel beta-sheet of 4 strands, order 2134 |
| α/β | 3 layers; a/b/a; parallel beta-sheet of 4 strands, order 2134 |
| α/β | 3 layers; a/b/a; core; parallel beta-sheet of 4 strands, order 2134 |
| α/β | core; 3 layers; a/b/a; parallel beta-sheet of 4 strands; 2134 |
| α/β | 3 layers; a/b/a; parallel beta-sheet of 4 strands, order 2134 |
| α/β | 3 layers; a/b/a; parallel beta-sheet of 4 strands, order 2134 |
| α/β | 3 layers; a/b/a; core; parallel beta-sheet of 4 strands, order 3214 |
| α/β | 3 layers; a/b/a; core; parallel beta-sheet of 4 strands, order 1423 |
| α/β | 3 layers; a/b/a; parallel beta-sheet of 5 strand, order 21345 |
| α/β | 3 layers; a/b/a; parallel beta-sheet of 5 strands, order 32145 |
| α/β | 3 layers; a/b/a; parallel beta-sheet of 5 strands, order 32145 |
| α/β | core; 3 layers; a/b/a; parallel beta-sheet of 5 strands, order 32145 |
| α/β | 3 layers; a/b/a; parallel beta-sheet of 5 strands, order 32145; Rossmann-like |
| α/β | 3 layers; a/b/a; parallel beta-sheet of 5 strands, order 32145; Rossmann-like |
| α/β | 3 layers; a/b/a, core; parallel beta-sheet of 5 strands, order 43215 |
| α/β | 3 layers; a/b/a; core; parallel beta-sheet of 5 strands, order 32145 |

TABLE 1-continued

Exemplary structures adopted by homologous superfamilies of proteins

| Class of secondary structure | Architecture and/or topology of folds within proteins |
|---|---|
| α/β | 3 layers; a/b/a, core; parallel beta-sheet of 5 strands, order 21354; topological similarity to a part of the arginase/deacetylase fold |
| α/β | core; 3 layers; a/b/a, parallel beta-sheet of 5 strands, order 21435; contains a deep trefoil knot |
| α/β | 3 layers; a/b/a; parallel or mixed beta-sheet of 4 to 6 strands |
| α/β | 3 layers; a/b/a; parallel beta-sheet of 6 strands, order 321456; Rossmann-like |
| α/β | 3 layers; a/b/a; parallel beta-sheet of 6 strands, order 321456 |
| α/β | 3 layers; a/b/a; parallel beta-sheet of 6 strands, order 321456 |
| α/β | 3 layers; a/b/a; parallel beta-sheet of 6 strands, order 321456; also contains a C-terminal alpha + beta subdomain |
| α/β | 3 layers; a/b/a; parallel beta-sheet of 6 strands, order 321456 |
| α/β | 3 layers; a/b/a; parallel beta-sheet of 6 strands, order 321456 |
| α/β | core; 3 layers; a/b/a; parallel or mixed beta-sheet of 6 strands, order 321456 |
| α/β | 3 layers; a/b/a; parallel beta-sheet of 6 strands, order 321456 |
| α/β | 3 layers; a/b/a; parallel beta-sheet of 6 strands, order 432156 |
| α/β | 3 layers; a/b/a; parallel beta-sheet of 6 strands, order 342156 |
| α/β | 3 layers; a/b/a; parallel beta-sheet of 6 strands, order 213456 |
| α/β | 3 layers; a/b/a; parallel beta-sheet of 6 strands, order 213465 |
| α/β | 3 layers; a/b/a, parallel or mixed beta-sheets of variable sizes |
| α/β | 3 layers; a/b/a, parallel beta-sheet of 6 strands, order 324156 |
| α/β | 3 layers; a/b/a, parallel beta-sheet of 7 strands, order 7165243 |
| α/β | 3 layers; a/b/a, parallel beta-sheet of 7 strands, order 3214567 |
| α/β | 3 layers; a/b/a, parallel beta-sheet of 7 strands, order 4321567 |
| α/β | 3 layers; a/b/a, parallel beta-sheet of 7 strands, order 3421567 |
| α/β | 3 layers; a/b/a, parallel beta-sheet of 7 strands, order 2314567; left-handed crossover connection between strands 2 & 3 |
| α/β | core; 3 layers; a/b/a; parallel beta-sheet of 7 strands, order 2134756 |
| α/β | 3 layers; a/b/a, parallel beta-sheet of 8 strands, order 21387456 |
| α/β | 3 layers; a/b/a; parallel beta-sheet of 8 strands, order 54321678 |
| α/β | beta(2)-(alpha-beta)2-beta; 2 layers; a/b; mixed beta-sheet of 5 strands, order 12345; strands 1 & 5 are antiparallel to the rest |
| α/β | beta(2)-(alpha-beta)2-beta(3); 3 layers; a/b/b; some topological similarity to the N-terminal domain of MinC |
| α/β | core; 2 layers; a/b; mixed beta-sheet of 6 strands, order 324561; strands 3 & 6 are antiparallel to the rest |
| α/β | 3 layers; a/b/a; parallel beta-sheet of 4 strands, order 2134 |
| α/β | core; 3 layers; a/b/a; parallel beta-sheet of 4 strands, order 1423 |
| α/β | 3 layers; a/b/a; parallel beta-sheet of 5 strands, order 32451 |
| α/β | core; 3 layers; a/b/a; mixed beta-sheet of 4 strands, order 4312; strand 3 is antiparallel to the rest |
| α/β | 3 layers; a/b/a; mixed beta-sheet of 4 strands, order 2143, strand 4 is antiparallel to the rest |
| α/β | 3 layers; a/b/a; mixed beta-sheet of 5 strands, order 13245, strand 1 is antiparallel to the rest |
| α/β | 3 layers; a/b/a; mixed beta-sheet of 5 strands, order 32145, strand 5 is antiparallel to the rest |
| α/β | 3 layers; a/b/a; mixed beta-sheet of five strands, order 21345; strand 4 is antiparallel to the rest |
| α/β | core; 3 layers; b + a/b/a; the central mixed sheet of 5 strands; order 21534; strand 2 is antiparallel to the rest |
| α/β | core; 3 layers; a/b/a; mixed beta-sheet of 5 strands, order 12345; strands 2 &, in some families, 5 are antiparallel to the rest |
| α/β | Core; 3 layers; a/b/a; mixed beta-sheet of 5 strands, order 21345; strand 5 is antiparallel to the rest |
| α/β | 3 layers; a/b/a; mixed beta-sheet of 5 strands, order 21345; strand 5 is antiparallel to the rest |
| α/β | 3 layers; a/b/a; mixed beta-sheet of 5 strands, order 32145; strand 2 is antiparallel to the rest |
| α/β | core; 3 layers; a/b/a; mixed sheet of 5 strands: order 21354; strand 4 is antiparallel to the rest; contains crossover loops |
| α/β | 3 layers; a/b/a; mixed beta-sheet of 5 strands; order: 21354, strand 5 is antiparallel to the rest; permutation of the Phosphorylase/hydrolase-like fold |
| α/β | 3 layers; a/b/a; mixed beta-sheet of five strands, order 21345; strand 1 is antiparallel to the rest |
| α/β | 3 layers; a/b/a; mixed beta-sheet of 6 strands; order: 213546, strand 5 is antiparallel to the rest; topological similarity to the MogA-like family fold |
| α/β | 3 layers; a/b/a; core; mixed beta-sheet of 6 strands, order 213456, strand 6 is antiparallel to the rest |
| α/β | 3 layers; a/b/a; mixed beta-sheet of 6 strands, order 165243, strand 3 is antiparallel to the rest |
| α/β | 3 layers; a/b/a; mixed beta-sheet of 6 strands, order 126345; strand 1 is antiparallel to the rest |
| α/β | core; 3 layers; a/b/a; mixed beta-sheet of 6 strands, order 324156; strand 5 is antiparallel to the rest |

TABLE 1-continued

Exemplary structures adopted by homologous superfamilies of proteins

| Class of secondary structure | Architecture and/or topology of folds within proteins |
|---|---|
| α/β | core; 3 layers; a/b/a; mixed beta-sheet of 6 strands, order 321456; strand 3 is antiparallel to the rest |
| α/β | core; 3 layers; a/b/a; mixed beta-sheet of 6 strands, order 321456; strand 3 is antiparallel to the rest |
| α/β | 3 layers; a/b/a; mixed beta-sheet of 6 strands, order 231456; strand 3 is antiparallel to the rest |
| α/β | 3 layers; a/b/a; mixed beta-sheet of 6 strands, order 251634; strand 6 is antiparallel to the rest |
| α/β | core; 3 layers; a/b/a; mixed beta-sheet of 6 strands, order 432156; strand 4 is antiparallel to the rest |
| α/β | core; 3 layers; a/b/a; mixed sheet of 7 strands, order 1237456; strands 1, 6 and 7 are antiparallel to the rest |
| α/β | 3 layers; a/b/a; mixed beta-sheet of 7 strands, order 3214567; strand 6 is antiparallel to the rest |
| α/β | core; 3 layers; a/b/a; mixed beta-sheet of 7 strands, order 3214576; strand 7 is antiparallel to the rest |
| α/β | 3 layers; a/b/a; mixed beta-sheet of 7 strands, order 3214576; strand 7 is antiparallel to the rest; topological similarity to SAM-dependent methyltransferases |
| α/β | main domain: 3 layers; a/b/a, mixed beta-sheet of 7 strands, order 3245671; strand 7 is antiparallel to the rest |
| α/β | 3 layers; a/b/a; mixed beta-sheet of 7 strands, order 3214657; strand 6 is antiparallel to the rest |
| α/β | 3 layers; a/b/a; mixed beta-sheet of 8 strands, order 32145678; strands 6 and 8 are antiparallel to the rest |
| α/β | core; 3 layers; a/b/a; mixed beta-sheet of 8 strands, order 12435678, strand 2 is antiparallel to the rest |
| α/β | core; 3 layers; a/b/a; mixed beta-sheet of 8 strands, order 32145687; strand 7 is antiparallel to the rest |
| α/β | 3 layers; a/b/a; mixed beta-sheet of 8 strands, order 34251687; strand 8 is antiparallel to the rest |
| α/β | core; 3 layers; a/b/a; mixed beta-sheet of 8 strands, order 21345678, strand 7 is antiparallel to the rest |
| α/β | 3 layers; a/b/a; mixed (mainly parallel) beta-sheet of 8 strands, order 32145678; strand 8 is antiparallel to the rest |
| α/β | 3 layers; a/b/a; mixed (mainly parallel) beta-sheet of 8 strands, order 34215786; strand 8 is antiparallel to the rest |
| α/β | core; 3 layers; a/b/a; mixed beta-sheet of 8 strands, order 45321678, strands 4 and 5 are antiparallel to the rest |
| α/β | core; 3 layers; a/b/a; mixed beta-sheet of 8 strands, order 43516728, strand 7 is antiparallel to the rest |
| α/β | 3 layers; a/b/a; mixed beta-sheet of 8 strands, order 78612354; strands 3, 4 and 8 are antiparallel to the rest |
| α/β | 3 layers; a/b/a; mixed beta-sheet of 9 strands, order 918736452; strands 1, 2 and 8 are antiparallel to the rest |
| α/β | 3 layers; a/b/a; mixed (mostly antiparallel) beta-sheet of 9 strands, order 432159876; left-handed crossover between strands 4 and 5 |
| α/β | 3 layers; a/b/a; mixed beta-sheet of 9 strands, order 342156798; strands 3, 8 and 9 are antiparallel to the rest; left-handed crossover connection between strands 6 and 7 |
| α/β | consists of two intertwined (sub)domains related by pseudo dyad; duplication |
| α/β | possible duplication: the topologies of N- and C-terminal halves are similar; 3 layers; a/b/a; single mixed beta-sheet of 10 strands, order 213549A867 (A = 10); strands from 5 to 9 are antiparallel to the rest |
| α/β | consists of two similar domains related by pseudo dyad; duplication |
| α/β | consists of two similar domains related by pseudo dyad; duplication |
| α/β | 3 layers; a/b/a; parallel beta-sheet of 5 strands, order 21345 |
| α/β | contains of two similar intertwined domains related by pseudo dyad; duplication |
| α/β | consists of two similar domains with 3 layers (a/b/a) each; duplication |
| α/β | consists of three similar domains with 3 layers (a/b/a) each; duplication |
| α/β | consists of three similar domains with 3 layers (a/b/a) each; duplication |
| α/β | consists of two domains of similar topology, 3 layers (a/b/a) each |
| α/β | consists of two non-similar domains, 3 layers (a/b/a) each |
| α/β | consists of two non-similar domains with 3 layers (a/b/a) each |
| α/β | consists of two non-similar alpha/beta domains, 3 layers (a/b/a) each |
| α/β | consists of two non-similar domains, 3 layers (a/b/a) each |
| α/β | consists of two non-similar domains |
| α/β | consists of two non-similar domains |
| α/β | 2 different domains; d1: [core; 3 layers; a/b/a; parallel sheet of 5 strands, order: 2134]; D2: [2 layers; a/b; mixed sheet of 6 strands, order 321645; strands 2 and 6 are antiparallel to the rest] |

TABLE 1-continued

Exemplary structures adopted by homologous superfamilies of proteins

| Class of secondary structure | Architecture and/or topology of folds within proteins |
|---|---|
| α/β | consists of two non-similar domains |
| α/β | consists of two different alpha/beta domains; (1) of the Flavodoxin-like fold (scop_cf 52171); (2) similar to the Restriction endonuclease-like fold (scop_cf 52979), inserted into domain 1 |
| α/β | contains a P-loop NTP-binding motif; mixed beta-sheet folds into a barrel-like structure with helices packed on one side |
| α/β | contains mixed beta-sheets; topology is partly similar to that of the catalytic C-terminal domain |
| α/β | duplication: tandem repeat of two domains; 3 layers (a/b/a); parallel beta-sheet of 4 strands, order 2134 |
| α/β | consists of two similar intertwined domain with 3 layers (a/b/a) each: duplication |
| α/β | consists of two similar intertwined domain with 3 layers (a/b/a) each: duplication |
| α/β | consists of two similar domains related by pseudo dyad; duplication |
| α/β | consist of two intertwined domains; duplication: contains two structural repeats of alpha-beta-(beta-alpha)3 motif with mixed beta-sheet, order: 1432, strand 1 is antiparallel to the rest |
| α/β | consist of two intertwined domains; contains partial duplication |
| α/β | consist of two different alpha/beta domains; N-terminal domain has a SurE-like topology with a left-handed beta-alpha-beta unit |
| α/β | core; alpha-beta(2)-(alpha-beta)2; 3 layers (a/b/a); mixed beta-sheet of 4 strands, order 2134; strand 2 is antiparallel to the rest |
| α/β | single helix packs against antiparallel beta-sheet |
| α/β | common alpha + beta motif for the active site region |
| α/β | consists of one alpha-helix and 4 strands of antiparallel beta-sheet and contains the catalytic triad Cys-His-Asn |
| α/β | core; (alpha)-beta-omega_loop-beta-alpha; embedded in larger different structures |
| α/β | contains long curved beta-sheet and 3 helices |
| α/β | beta-alpha-beta-alpha(2); antiparallel beta-ribbon |
| α/β | beta-alpha(2)-beta; antiparallel strands |
| α/β | alpha-beta(2)-alpha; antiparallel hairpin |
| α/β | alpha-beta(2)-alpha; 2 layers a/b; antiparallel beta-hairpin |
| α/β | alpha(3)-beta(2); antiparallel hairpin |
| α/β | beta(3)-alpha |
| α/β | beta(3)-alpha; 2 layers; alpha/beta |
| α/β | alpha1-beta3; 2 layers; alpha/beta; order 132 |
| α/β | beta-alpha-beta(2); 2 layers; alpha/beta; antiparallel beta-sheet: order 132 |
| α/β | beta-(alpha)-beta-alpha-beta(2); 3 layers; alpha/beta/alpha; antiparallel beta-sheet: order 1243 |
| α/β | beta-(2)-alpha(2)-beta(2); 2 layers; beta/alpha; antiparallel beta-sheet: order 1243; topological similarity to the common core of ribosomal proteins L23 and L15e |
| α/β | beta-(2)-alpha(3)-beta(2); 2 layers; beta/alpha; mixed beta-sheet: order 1234; strands 2 and 3 a parallel to each other |
| α/β | alpha-beta(3)-alpha-beta(2); 3 layers; alpha/beta/alpha |
| α/β | alpha-beta(3)-alpha-beta(2)-alpha; 2 layers; alpha/beta |
| α/β | beta(2)-alpha(2)-beta; 2 layers; 3-stranded antiparallel beta-sheet, order 213; HTH motif; also includes the extra N-terminal, DNA minor groove-binding helix |
| α/β | alpha-beta(4)-alpha-beta(2)-alpha; 2 layers; alpha/beta |
| α/β | beta(4)-alpha-beta(2)-alpha; 2 layers; alpha/beta; antiparallel beta-sheet, order: 651234 |
| α/β | core; beta(3)-alpha-beta-alpha; 2 layers; alpha/beta; left-handed crossover |
| α/β | core; beta(2)-alpha-beta(2); mixed beta-sheet 2143 |
| α/β | alpha + beta sandwich |
| α/β | core; alpha-beta(4); helix packs against coiled antiparallel beta-sheet |
| α/β | alpha-beta-alpha-beta-alpha(2)-beta(3); antiparallel beta-sheet; order: 15432 |
| α/β | alpha(2)-beta(4)-alpha, 2 layers; alpha/beta, antiparallel beta sheet, meander |
| α/β | beta(3)-alpha-beta(2)-alpha; 2 layers; alpha/beta; antiparallel beta-sheet, order: 12543 |
| α/β | core; alpha-beta(3)-alpha, 2 layers; alpha/beta, three-stranded antiparallel beta sheet, strand order 123 |
| α/β | core; beta(2)-alpha(2), 2 layers; alpha/beta; long C-terminal helix forms dimeric parallel and tetrameric antiparallel coiled coils |
| α/β | helix-swapped dimer of beta(4)-alpha motifs |
| α/β | beta-BETA(2)-beta-alpha-beta(2); antiparallel sheet: order 2134 packed against helix and BETA-hairpin on the same side; irregular C-terminal tail |
| α/β | Dimeric |
| α/β | alpha-beta(4)-alpha(3); core; meander beta-sheet plus one helix 2 |
| α/β | core; three short helices packed against a barrel-like beta-sheet; some similarity to the SH3-like fold |

TABLE 1-continued

Exemplary structures adopted by homologous superfamilies of proteins

| Class of secondary structure | Architecture and/or topology of folds within proteins |
|---|---|
| α/β | beta*-alpha-beta(2)-alpha-beta-alpha; mixed beta sheet forms a partly open barrel: (n* = 4, S* = 8) |
| α/β | beta-alpha-beta(4)-alpha-beta(2); contains beta-sheet barrel (n = 5, S = 8) |
| α/β | beta(3)-alpha(2)-beta; 2 layers; mixed beta-sheet, order 4123, strands 1 and 4 are parallel to each other |
| α/β | mixed beta-sheet folds into a barrel (n = 8, S = 14) around the central helix |
| α/β | beta-sheet folds into a barrel (n = 11, S = 14) around the central helix |
| α/β | beta-sheet folds into a barrel (n = 12, S = 12) around the central helix |
| α/β | contains very long N-terminal helix, which end is packed against beta-sheet |
| α/β | core; beta(7)-alpha(2); N- and C-terminal extensions form a coiled coil subdomain |
| α/β | beta(6)-alpha; antiparallel beta-sheet, meander |
| α/β | beta(3)-alpha-beta(3)-alpha; 3 layers a/b/a |
| α/β | alpha(2)-beta(5)-alpha(2); 3 layers a/b/a; meander beta-sheet |
| α/β | core; beta(2)-alpha-beta(2); antiparallel beta-sheet |
| α/β | beta(4)-alpha-beta; 2 layers; alpha/beta; mixed beta-sheet, order: 51234 |
| α/β | alpha-beta-X-beta(2); 2 layers; alpha/beta; mixed beta-sheet, order: 123 |
| α/β | beta-alpha-beta-(alpha)-beta(2); 2 layers; alpha/beta; mixed beta-sheet, order: 1342 |
| α/β | beta(2)-alpha-beta; 2 layers; alpha/beta |
| α/β | beta-alpha-beta(3); 2 layers; alpha/beta |
| α/β | beta-alpha-beta(3); 2 layers; alpha/beta |
| α/β | beta(2)-alpha-beta(3); 2 layers; alpha/beta |
| α/β | multiple repeats of beta(2)-alpha(2) motif |
| α/β | beta(2)-alpha(3)-beta; two layers; alpha/beta; antiparallel sheet: order 213 |
| α/β | beta(4)-alpha(2); two layers; alpha/beta; antiparallel sheet: order 1432 |
| α/β | beta(2)-alpha(2)-beta(2)-alpha-beta; two layers; alpha/beta; antiparallel sheet: order 51234 |
| α/β | beta-alpha(2)-beta(4)-alpha-beta(2); two layers; alpha/beta; bifurcated coiled beta-sheet: order of the first 5 strands: 23154 |
| α/β | beta(4)-alpha(2)-beta(2)-alpha; antiparallel sheet: order 123465 |
| α/β | beta-alpha-beta(6)-alpha(2); antiparallel sheet: order 165432 |
| α/β | beta(3)-alpha(2)-beta-alpha(2)-beta3; 2 layers alpha/beta; antiparallel sheet: order 1234567 |
| α/β | alpha-beta(6)-alpha(2)-beta-alpha(n); 3 layers alpha/beta/alpha; antiparallel sheet: order 1234567 |
| α/β | beta(4)-alpha-beta(2)-alpha(2); mixed, predominately antiparallel beta-sheet, order: 123465, strands 4 and 5 are parallel to each other |
| α/β | core; beta-alpha-beta(4); 2 layers; alpha/beta |
| α/β | core; beta-alpha-beta(4); 2 layers; alpha/beta |
| α/β | core; beta-alpha(2)-beta-X-beta(2); 2 layers; alpha/beta; antiparallel beta-sheet: order 1342 |
| α/β | alpha + beta sandwich; loop across free side of beta-sheet |
| α/β | alpha-beta-loop-beta(3); loop across free side of beta-sheet |
| α/β | core; beta-BETA-alpha-beta-BETA-beta-alpha; contains a beta-hammerhead motif similar to that in barrel-sandwich hybrids |
| α/β | core; beta(2)-alpha(2)-beta(2)-alpha(2); 2 layers a/b; mixed sheet: 2143 |
| α/β | beta(2)-alpha(n)-beta; 2 layers a/b; antiparallel sheet: 123 |
| α/β | alpha-beta(2)-alpha-beta-alpha(2); 3 strands of antiparallel sheet: 213 |
| α/β | beta-alpha(2)-beta-alpha-beta; 2 layers; alpha/beta |
| α/β | beta-alpha-beta(2)-alpha(2); 3 layers; alpha/beta/alpha; antiparallel beta-sheet: order 123 |
| α/β | beta-alpha(2)-beta(2); 2 layers; alpha/beta; antiparallel beta-sheet: order 123 |
| α/β | alpha-beta(3)-alpha(2); 2 layers; alpha/beta |
| α/β | (beta)-alpha-beta(3)-alpha; 2 layers; alpha/beta |
| α/β | alpha-beta(3)-alpha; 2 layers; alpha/beta |
| α/β | duplication: consists of two beta(3)-alpha repeats; 3 layers; beta/alpha/beta |
| α/β | beta-alpha-beta(2)-alpha; 2 layers; alpha/beta |
| α/β | alpha(2)-beta(3)-alpha(3); 2 layers alpha/beta, 3-stranded antiparallel beta-sheet; order 123 |
| α/β | alpha(3)-beta-alpha(2)-beta(2); 2 layers alpha/beta, 3-stranded antiparallel beta-sheet; order 123 |
| α/β | beta-alpha(2)-beta(2)-alpha; 2 layers; alpha/beta |
| α/β | core; alpha-beta(2)-(alpha)-beta; 2 layers; alpha/beta |
| α/β | core; alpha-beta-turn-beta-X-beta-(alpha); mixed beta-sheet, order of core strands: 123 |
| α/β | alpha(2)-beta(4); 2 layers; alpha/beta; antiparallel beta-sheet: order 2143 |
| α/β | alpha-beta(3)-alpha-beta-alpha; bifurcated coiled beta-sheet |
| α/β | beta(3)-alpha(3); meander and up-and-down bundle |
| α/β | beta-alpha(3)-beta(2); 2 layers; alpha/beta; related to the enolase/MLE N-domain fold by a circular permutation |
| α/β | alpha-beta-alpha(3)-beta(2); 2 layers; alpha/beta; |

TABLE 1-continued

Exemplary structures adopted by homologous superfamilies of proteins

| Class of secondary structure | Architecture and/or topology of folds within proteins |
|---|---|
| α/β | 3-helical bundle packed against 3-stranded mixed beta-sheet |
| α/β | beta(3)-alpha(4); meander beta-sheet packed against array of helices; contains Pro-rich stretch |
| α/β | beta(3)-alpha(5); meander beta-sheet packed against array of helices |
| α/β | beta-alpha-beta(2)-alpha; 2 layers; alpha/beta; mixed sheet 213; crossing loops |
| α/β | alpha-beta(3)-alpha(3); 2 layers; a/b; mixed beta-sheet, order: 132; crossing loops |
| α/β | alpha + beta sandwich with antiparallel beta-sheet; (beta-alpha-beta) × 2 |
| α/β | consists of two alpha + beta subdomains with some similarity to the ferredoxin-like fold |
| α/β | beta-alpha-beta-X-beta(2)-alpha(2)-beta; antiparallel beta-sheet, order 24153; topological similarity to the ferredoxin-like fold (scop_cf 54861) |
| multi | contains a cluster of helices and a beta-sandwich |
| multi | contains a cluster of helices and a beta-sandwich |
| multi | contains a cluster of helices and an alpha + beta sandwich |
| multi | consists of an all-alpha and alpha + beta domains |
| multi | contains a helical bundle with a buried helix and an alpha + beta insert domain |
| multi | consists of an all-alpha and alpha + beta domains connected by antiparallel coiled coil |
| multi | contains a cluster of helices and an alpha/beta domain |
| multi | contains an (8, 10) beta-barrel and an all-alpha domain |
| multi | 2 domains; (1) all-alpha; 5 helices; (2) contains an open beta-sheet barrel: n* = 5, S* = 8; complex topology |
| multi | N-terminal domain is an alpha + beta, C-terminal domain is an alpha/beta with mixed beta-sheet |
| multi | divided into morphological domains including "palm", "thumb" and "fingers"; the catalytic "palm" domain is conserved to all members |
| multi | Multidomain subunits of complex domain organization |
| multi | 3 domains; (1&2) alpha + beta, with domain 2 being inserted in domain 1; (3) all-alpha |
| multi | 4 domains; (1) Toprim alpha/beta; (2&4) "winged helix"-like; (3) barrel: n = 6, S = 8 |
| multi | 4 domains; (1) toprim alpha/beta; (2) "winged helix"-like; (3) alpha + beta; (4) all-alpha |
| multi | 2 domains; (1) toprim alpha/beta; (2) "winged helix"-like |
| multi | 2 domains; (1) alpha + beta; (2) toprim alpha/beta |
| multi | consists of three domains; alpha-helical dimerisation domain (res. 1-53) with HhH motif (Pfam 00633); 'treble cleft' C4 zinc-finger domain (54-76; Pfam 02132); and Toprim domain (76-199; segment-swapped dimer; Pfam 01751) |
| multi | 2 domains; alpha + beta and all-beta |
| multi | 2 domains; (1) alpha + beta; beta3-alpha2-beta2; (2) alpha/beta, a part of its mixed sheet forms barrel: n = 6, S = 8 |
| multi | 3 domains; (1) all-alpha; (2&3) alpha + beta |
| multi | 2 domains; (1) alpa/beta; (2) Fe—S cluster-bound |
| multi | 2 domains; (1) alpha/beta of a Rossmann-fold topology, binds NAD (2) multihelical array |
| multi | 4 domains; (1&2) duplication: share the same alpha/beta fold; (3) beta-barrel; (4) alpha + beta |
| multi | 2 domains; (1) alpha + beta; (2) alpha/beta (interrupts domain 1) |
| multi | 4 domains; (1) 3-helical bundle; (2) alpha + beta of ferredoxin-like fold (3 and 4) alpha + beta of dsRDB-like fold |
| multi | 3 domains; (1) 3-helical bundle; (2 and 3) alpha + beta of different folds: domain 3 has a ferredoxin-like fold and is inserted in domain 2 |
| multi | 3 domains; (1) 4-helical bundle; (2) alpha + beta; (3) "winged helix"-like |
| multi | 3 domains; (1 and 2) alpha + beta; (3) mostly alpha, inserted in domain 2 |
| multi | 3 domains; (1) spectrin repeat-like 3-helical bundle; (2 and 3) alpha/beta; Rossmann-fold topology |
| multi | 3 domains; (1) protozoan pheromone-like alpha-helical bundle; (2) rubredoxin-like domain lacking metal-binding site; (3) alpha + beta heterodimerisation domain: alpha-beta(5)-alpha |
| multi | 2 domains; (1) alpha-helical bundle; (2) beta-barrel (n = 5, S = 8) |
| multi | 3 domains; (1) alpha-helical bundle; (2&3) complex all-beta folds |
| multi | 2 closely associated domains; (1) all-alpha, EF-hand like; (2) alpha + beta, Frataxin-like |
| multi | 2 domains; d1: [all-alpha; 3-helical bundle, similar to the immunoglobulin/albumin-binding domain-like fold (scop_cf 46996)]; d2: [alpha/beta; 3 layers; a/b/a; 6-stranded mixed beta-sheet, order: 321456, strand 6 is antiparallel to the rest] |
| multi | 3 domains; d1: alpha + beta [alpha(2)-beta(3); mixed sheet: 213]; d2: alpha/beta of the NAD(P)-binding Rossmann-fold superfamily (scop_sf 51735, most similar to scop_fa 51883 and scop_fa 51736); d3: alpha + beta of the glutamine synthetase/guanido kinase fold (scop_cf 55930); d1 and d3 form a single beta-sheet |

TABLE 1-continued

Exemplary structures adopted by homologous superfamilies of proteins

| Class of secondary structure | Architecture and/or topology of folds within proteins |
|---|---|
| multi | 2 domains; d1 [alpha/beta; related to the PFK N-terminal domain (scop_sf 53784)]; d2 [all-beta; atypical beta-sandwich made of 4 structural repeats of beta(3) unit] |
| multi | 2 domains; d1 (1-64, 174-335) [alpha/beta; 3 layers; a/b/a; mixed beta sheet of 9 strands, order: 219863457; strands 1, 5 and 8 are antiparallel to the rest]; d2 (65-142) [all-beta; barrel, closed (n = 6, S = 10); greek-key; topologically similar to the split barrel fold (scop_cf 50474) |
| multi | 2 domains; (1) alpha + beta (res 1-192), a circularly permuted rS5 domain 2-like fold (scop_cf 54210); (2) alpha/beta with parallel beta-sheet of 4 strands, order 2134 |
| multi | consists of two domains; d1: alpha + beta (78-190; alpha-beta(4)-alpha-beta-alpha; 3 layers; antiparallel beta-sheet of 5 strands; order 51234); d2: alpha/beta similar to the G-domain fold (191-381; scop_fa 52592) |
| multi | 2 domains; (1) all-alpha, (2) alpha + beta; asymmetric homodimer with each domain intertwining with its counterpart |
| multi | 4 domains; three intertwined predominately alpha domains and one jelly-roll beta-sandwich |
| multi | large protein without apparent domain division; has a number of all-alpha regions and one all beta domain near the C-end |
| multi | large protein without apparent domain division |
| multi | large protein without apparent domain division |
| membrane + surface | multi-helical domains of various folds which unfold in the membrane |
| membrane + surface | core; up-and-down bundle of seven transmembrane helices tilted 20 degrees with respect to the plane of the membrane |
| membrane + surface | five transmembrane helices forming a sheet-like structure |
| membrane + surface | 12 transmembrane helices in an approximate threefold rotational symmetric arrangement |
| membrane + surface | core; 7 transmembrane helices organized into two bundles, one formed by the first two helices and the other by the rest |
| membrane + surface | two antiparallel transmembrane helices |
| membrane + surface | core; up-and-down bundle of four transmembrane helices |
| membrane + surface | core; 8 helices, 2 short helices are surrounded by 6 long transmembrane helices |
| membrane + surface | 11 transmembrane helices; duplication: consist of 2 structural repeats of five helices each plus extra C-terminal helix |
| membrane + surface | 12 transmembrane helices; duplication: the N- and C-terminal halves are structurally similar |
| membrane + surface | core; 18 transmembrane helices |
| membrane + surface | oligomeric transmembrane alpha-helical proteins |
| membrane + surface | oligomeric transmembrane alpha-helical protein |
| membrane + surface | oligomeric transmembrane alpha-helical protein |
| membrane + surface | heteropentameric transmembrane alpha-helical protein; 4 transmembrane helices per subunit |
| membrane + surface | oligomeric fold; 3 transmembrane helices per subunit |
| membrane + surface | oligomeric fold; 3 transmembrane helices per subunit |
| membrane + surface | 9 transmembrane helices |
| membrane + surface | 10 transmembrane helices forming of a gated channel |
| membrane + surface | core; 11 transmembrane helices |
| membrane + surface | core; hairpin of two transmembrane helices |
| membrane + surface | core; three transmembrane helices, bundle |
| membrane + surface | multihelical; complex architecture with several transmembrane helices |
| membrane + surface | multihelical; complex architecture with several transmembrane helices |
| membrane + surface | 12 transmembrane helices; duplication: the N- and C-terminal halves of the whole proteins are structurally similar |
| membrane + surface | core; three transmembrane helices, up-and-down bundle |

TABLE 1-continued

Exemplary structures adopted by homologous superfamilies of proteins

| Class of secondary structure | Architecture and/or topology of folds within proteins |
|---|---|
| membrane + surface | core; four transmembrane helices, up-and-down bundle, binds one or two heme groups in between the helices |
| membrane + surface | membrane-associated alpha-helical protein; no transmembrane helices |
| membrane + surface | membrane-associated alpha-helical protein; no transmembrane helices |
| membrane + surface | 2 helices, hairpin |
| membrane + surface | core; multihelical; consists of three transmembrane regions of 2, 2 and 6 helices, separated by cytoplasmic domains |
| membrane + surface | membrane all-alpha fold |
| membrane + surface | membrane all-alpha fold; 6-helical "barrel" with internal binding cavity |
| membrane + surface | membrane all-alpha fold; three transmembrane helices |
| membrane + surface | , gathers together transmembrane barrels of different (n, S) |
| membrane + surface | subunit fold contains tandem repeat of alpha-beta hairpin-alpha(2) motif |
| membrane + surface | consists of three domains; beta-barrel (res. 29-38, 170-259; scop_cf 50412); barrel-sandwich hybrid (39-72, 135-169; scop_sf 51230) and long alpha-hairpin (73-134; scop_cf 46556) |
| membrane + surface | subunit fold contains beta-sandwich of Ig-like (grerk-key) topology and a beta-ribbon arm that forms an oligomeric transmembrane barrel |
| membrane + surface | contains several large open beta-sheets |
| membrane + surface | 3 domains; (1) alpha + beta; (2&3) all-beta |
| membrane + surface | 2 domains; (1) alpha + beta; (2) all-beta, similar to the CalB domain fold but the two last strands are transposed |
| membrane + surface | 2 intertwined domains; all-beta and alpha + beta |
| membrane + surface | 2 domains; d1: complexed all-beta fold; d2: coiled-coil (trimeric) helical region |
| membrane + surface | 3 intertwined all-beta domains |
| membrane + surface | trimer; one subunit consists of an alpha/beta oligomerization subdomain [3-stranded parallel beta-sheet, order 213], and an antiparallel coiled coil |
| membrane + surface | 4 domains; I (res. 14-225) and II (226-487) are beta-sandwiches of similar gamma-crystallin like topologies; III (488-594) has a beta-grasp like fold; IV (595-735) has an Ig-like fold |
| Other | nearly all-alpha |
| Other | disulfide crosslinked alpha-helical hairpin |
| Other | disulfide-bound fold; contains beta-hairpin with two adjacent disulfides |
| Other | disulfide-rich fold; all-beta; 3 antiparallel strands |
| Other | disulfide-rich fold; all-beta; 3 antiparallel strands |
| Other | disulfide-rich fold; all-beta; 3 antiparallel strands |
| Other | disulfide-rich; alpha + beta; 3 antiparallel strands followed by a short alpha helix |
| Other | disulfide-rich fold; nearly all-beta |
| Other | disulfide-rich alpha + beta fold |
| Other | Disulfide-rich fold, nearly all-beta |
| Other | alpha + beta fold with two crossing loops |
| Other | disulfide-rich fold |
| Other | disulfide-rich calcium-binding fold |
| Other | disulfide-rich alpha + beta fold |
| Other | disulfide-rich fold; nearly all-beta |
| Other | disulfide-rich small alpha + beta fold; topological similarity to the Ovomucoid domain III |
| Other | disulfide-rich fold; common core is alpha + beta with two conserved disulfides |
| Other | disulfide-rich fold; all-beta; duplication: contains two structural repeats |
| Other | disulfide-rich fold; common core is all-beta |
| Other | disulfide-rich all-beta fold |
| Other | disulfide-rich all-alpha fold |
| Other | small disulfide-rich |
| Other | disulfide-rich; nearly all-beta |
| Other | disulfide-rich; nearly all-beta |
| Other | disulfide-rich; alpha + beta |
| Other | duplication: consists of three similar disulfide-rich domains |
| Other | duplication: consists of two similar disulfide-rich domains, alpha + beta |
| Other | disulfide-rich; all-beta; open barrel, 5 strands; OB-fold-like |
| Other | disulfide-rich, all-beta |
| Other | disulfide-rich, alpha + beta |
| Other | disulfide-rich, alpha + beta |

TABLE 1-continued

Exemplary structures adopted by homologous superfamilies of proteins

| Class of secondary structure | Architecture and/or topology of folds within proteins |
|---|---|
| Other | disulfide-rich, alpha + beta |
| Other | disulfide-rich, alpha + beta |
| Other | disulfide-rich |
| Other | disulfide-rich, all-alpha |
| Other | disulfide-rich; all-alpha |
| Other | disulfide-rich, alpha + beta |
| Other | disulfide-rich |
| Other | disulfide-rich; all-alpha; calcium-binding |
| Other | disulfide-rich |
| Other | disulfide-rich all-beta fold; contains beta sandwich of 5 strands |
| Other | disulfide-rich six-stranded beta-sandwich; jelly-roll |
| Other | bipartite cysteine-rich all-alpha domain; a single helix in the N-terminal part (chain A) is linked by disulfides to the C-terminal part (chain B) [3-helical bundle of the RuvA C-terminal domain-like fold (scop_cf 46928) |
| Other | Calcium ion-bound |
| Other | a few helical turns and a disulfide-crosslinked loop |
| Other | a few helical turns assembled without a hydrophobic core? |
| Other | folds around 4Fe—4S cluster |
| Other | folds around 4Fe—4S cluster |
| Other | alpha + beta metal(zinc)-bound fold; beta-hairpin + alpha-helix |
| Other | all-alpha dimetal(zinc)-bound fold |
| Other | alpha + beta metal(zinc)-bound fold |
| Other | consist of two different zn-binding subdomains, each subdomain resembles a distorted glucocorticoid receptor-like fold |
| Other | metal(zinc)-bound fold |
| Other | metal(zinc or iron)-bound fold; sequence contains two CX(n)C motifs, in most cases n = 2 |
| Other | zinc-bound beta-ribbon motif |
| Other | zinc-bound beta-ribbon motif |
| Other | zinc-bound alpha + beta motif |
| Other | dimetal(zinc)-bound alpha + beta motif; structurally diverse |
| Other | zinc-bound alpha + beta motif |
| Other | metal(iron)-bound fold |
| Other | metal(zinc)-bound alpha + beta fold |
| Other | metal(zinc)-bound alpha + beta fold |
| Other | dimetal(zinc)-bound alpha + beta fold |
| Other | dimetal(zinc)-bound alpha + beta fold |
| Other | metal(zinc)-bound alpha + beta fold |
| Other | metal(zinc)-bound alpha + beta fold |
| Other | metal(zinc)-bound alpha + beta fold |
| Other | Zn-binding, all-alpha fold |
| Other | all-alpha fold; Zn-binding sites are in the loops connecting helices |
| Other | alpha-helical fold with two Zn-binding sites |
| Other | metal(zinc)-bound extended beta-hairpin fold |
| Other | metal(zinc)-bound fold |
| Other | metal(zinc)-bound fold |
| Other | metal(calcium)-bound fold |

Terms used in Table 1 will be apparent to the skilled artisan. However, the following definitions are provided for clarity below.

"Meander" is a simple topology of a beta-sheet where any two consecutive strands are adjacent and antiparallel.

"Up-and-down" is the simplest topology for a helical bundle or folded leaf, in which consecutive helices are adjacent and antiparallel; it is approximately equivalent to the meander topology of a beta-sheet.

"Crossover connection" links secondary structures at the opposite ends of the structural core and goes across the surface of the domain.

"Greek-key" is a topology for a small number of beta sheet strands in which some interstrand connections going across the end of barrel or, in a sandwich fold, between beta sheets.

"Jelly-roll" is a variant of Greek key topology with both ends of a sandwich or a barrel fold being crossed by two interstrand connections.

"All-alpha" class has the number of secondary structures in the domain or common core described as 3-. 4-, 5-. 6- or multi-helical.

"Bundle" is an array of alpha-helices each oriented roughly along the same (bundle) axis. It may have twist, left-handed if each helix makes a positive angle to the bundle axis, or be right-handed if each helix makes a negative angle to the bundle axis.

"Folded leaf" is a layer of alpha-helices wrapped around a single hydrophobic core but not with the simple geometry of a bundle.

"Array" (of hairpins) is an assembly of alpha-helices that can not be described as a bundle or a folded leaf.

"Closed", "partly opened" and "opened" for all-alpha structures describes the extent in which the hydrophobic core is screened by the comprising alpha-helices. "Opened" means that there is space for at least one more helix to be easily attached to the core.

Beta-sheets can be "antiparallel" (i.e. the strand direction in any two adjacent strands are antiparallel), "parallel" (all strands are parallel each other) or "mixed" (there is one strand at least that is parallel to one of its two neighbours and antiparallel to the other).

"All-beta" class includes two major fold groups: sandwiches and barrels. The "sandwich" folds are made of two beta-sheets which are usually twisted and pack so their strands are aligned. The "barrel" fold are made of single beta-sheet that twists and coils upon itself so, in most cases, the first strand in the beta sheet hydrogen bond to the last strand. The strand directions in the two opposite sides of a barrel fold are roughly orthogonal. Orthogonal packing of sheets is also seen in a few special cases of sandwich folds "Barrel structures" are usually closed by main-chain hydrogen bonds between the first and last strands of the beta sheet, in this case it is defined by the two integer numbers: the number of strand in the beta sheet, n, and a measure of the extent the extent to which the strands in the sheet are staggered the shear number, S.

"Partly open barrel" has the edge strands not properly hydrogen bonded because one of the strands is in two parts connected with a linker of more than one residue. These edge strands can be treated as a single but interrupted strand, allowing classification with the effective strand and shear numbers, n* and S*. In the few open barrels the beta sheets are connected by only a few side-chain hydrogen bonds between the edge strands.

An additional limitation on the use of available structure data on proteins for screening applications, as opposed to theoretical analyses of individual proteins is that they are largely biased data sets containing large numbers of redundant sequences and sequence annotations. For example, the CATH database is a hierarchical classification of domains, within protein structures, in the Protein Data Bank (PDB; Berman et al., Nucl. Acids Res. 28, 235-242, 2000) and, as a consequence, provides structure data that is reflective of the PDB. For example, there are about 32 architectures described in the CATH database, however there is an enormous amount of bias in those architectures, because approximately 30% of folds and 50% of protein superfamilies are contained within about 4-5 architectures, in particular αβ-sandwiches (two- and three-layer). αβ-barrel. β-barrel, α-updown structures (see Orengo et al., Ann. Rev. Biochem. 74, 867-900, 2005). As with architecture of proteins, there is enormous bias in the population of folds in public databases, such that less than 0.1% of fold groups are very large, accounting for nearly 40% of all sequence families in the PDB, see Orengo et al., Ann. Rev. Biochem. 74, 867-900 (2005). Many folds are also reported as sharing common structural motifs due to the recurrence of simple structural motifs e.g., αβ-motifs, ββ-motifs, split βαβ-motifs. These biases may not necessarily be reflective of a true distribution of protein structures in nature and, in fact, may arise because the bulk of information available to date is based on crystallization studies or limited classes of proteins that have been studied extensively (Ranea et al., J. Mol. Biol. 336, 871-887, 2004).

On the other hand, it is likely that there does exist a bias in nature towards particular folds, simply because of the evolutionary constraints applied to protein structure and function determination. For example, nearly 80 different folds are classified as adopting a three-layer αβ-sandwich architecture, and the most highly-populated fold groups adopt regular architectures (e.g., TIM barrel fold, αβ-barrel, Rossman fold; three-layer, αβ-sandwich; αβ-plait, two-layer αβ-sandwich) that may be more stable when mutated (Orengo et al., ibid.). In support of this conclusion, recent statistical analyses suggest that more highly-represented folds i.e., "superfolds" support a much broader repertoire of primary sequences than other folds (Shakhnovich et al., J. Mol. Biol. 326, 1-9, 2003). Thus, whilst peptide libraries have been produced from native proteins e.g., using proteolytic digestions products (see, for example WO2004/008148) the source protein samples are inevitably biased for common structures such that less common structures are under-represented, or lost.

In general, methods known in the art for producing peptide libraries generally attempt to provide large numbers of sequences in order to be "representative" of the complement of proteins in the source oraanism(s) from which the sequences were derived. In so doing, these methods inevitable introduce redundancy into the libraries e.g., by virtue of the natural bias towards the more common regular folds, as discussed supra.

Accordingly, there is a need in the art for libraries of peptides capable of forming, structures such as protein folds that retain their structures when isolated from their native contexts i.e., when sequences flanking the folds in the full-length proteins from which they are derived are substantially removed. The production of such libraries is not trite, because many folds are buried in proteins in connection with other parts of the protein, upon which their stability depends i.e., they are not independent. Additionally, whilst it is clearly desirable from a practical perspective to produce synthetic peptide libraries for high-throughput screening approaches, such libraries have an upper limit of peptide length that can readily be synthesized and displayed, whereas many sequence annotations indicate structures that are much longer than such practical considerations permit. Furthermore, based on the hypothesis that distinct folds are conserved generally such that variations in primary amino acid sequence largely affect their ligand-binding affinities, it is desirable for such libraries to separately display distinct folds. However, there is an absence of large data sets of distinct folds that could readily be adapted to the synthesis of peptide libraries, and a natural bias towards folds that appear capable of withstanding mutations. Moreover, one needs to be particularly judicious in the choice of particular sequences in a library if one is to represent the natural repertoire of sequences comprehensively, without undue bias for more commonly used classes of folds at the expense of less commonly used structures.

SUMMARY OF INVENTION

The present invention is predicated in part on the understanding by the inventors that protein structures, including secondary structures (i.e., conformations), assemblies of secondary structures, and tertiary structures (e.g., folds or subdomains) formed by interactions between secondary structures, are both necessary and sufficient for high affinity protein interactions to occur; and that there are a limited number of "folds" in nature. This is notwithstanding enormous diversity in primary amino acid sequences of proteins having, conserved structure.

Unless specifically stated or the context requires otherwise, the term "structure" is to be taken in its broadest context to mean shape as opposed to a primary sequence of amino acids.

The term "secondary structure" will be known by those skilled in the biochemical and biophysical arts to refer to a conformation assumed by a primary amino acid sequence such as, for example an α-helical structure or β=sheet.

As used herein, the term "assemblies" is meant a collection or plurality of stated integers. Accordingly, the term "assemblies of secondary structures" are a plurality of conformations including those that are loosely-associated with one another and those that are folded onto one another i.e., folds.

By "ligand" in the present context is meant a molecule having a binding affinity for a particular secondary structure, assembly of secondary structures or fold. Ligands include, but are not limited to, enzyme substrates, cofactors, receptors, binding partners in protein-protein interactions or DNA-protein interactions or RNA-protein interactions etc., antibodies, antigens, agonists, antagonists, inverse agonists. Ligands may be nucleic acid (e.g., DNA, mRNA, rRNA, tRNA. RNAi, ribozyme, antisense RNA, minizyme, etc), amino acid, peptide, protein, carbohydrate or other organic molecule, small molecule, metal ion, etc.

The inventors have now applied these realizations to a new generation of peptide libraries for drug discovery, said libraries comprising peptides e.g., synthetic peptides, that form such secondary and tertiary structures. The secondary structures (i.e., conformations), assemblies of secondary structures, and tertiary structures (e.g., folds) contained within the structure libraries described herein are generally independent of the need for flanking, sequences in the proteins from which they are derived, in the sense that they have a high probability of maintaining sufficient structure when isolated from those flanking sequences in the protein of origin i.e., "their native context". This is subject to the proviso that one or more other sequences a linker, tag, or protein transduction domain) may be added to a primary sequence that folds or associates with another integer to produce a secondary structure, assemblies of secondary structures, or fold. Libraries produced using the method described herein according to any embodiment are useful for identifying a peptide capable of binding to a target molecule and, as a consequence, having a bioactivity of interest. Such peptides represent attractive therapeutic and/or diagnostic compounds in addition to reagents for therapeutic target validation.

The libraries produced in accordance with the inventive method are based on "source data" comprising annotations of primary sequences determined and/or predicted structures for proteins from which the component peptides are derived. Exemplary source data include, for example, protein sequence resources such as PRINTS, Pfam, SMART, ProDom, InterPro, TIGRFAMs, ADDA, CHOP, ProtoNet, SYSTERS, iProClass, SWISSPROT, COG/KOG, and protein structure family resources such as CAMPASS (Cambridge University, UK), CATH database (University College, London, UK), CE (SDSC, La Jolla, Calif., USA), DHS (University College, London, UK), ENTREZ/MMDB (NCBI. Bethesda Md., USA), Structural Classification of Protein Database (SCOP) (Andreeva et al., *Nucl. Acid Res.* 32:D226-D229, 2004), or the Protein Data Bank (PDB) (Berman et al., *Nucleic Acid Res.* 28: 235, 2000). It is to be understood that such source data generally need additional refinement to enrich for particular amino acid sequence products capable of independently-forming secondary structures and/or assemblies of secondary structures and/or folds suitable for practical application in drug screening and to ensure that an optimal structural diversity of the library is achieved Accordingly, the present invention provides a method for producing a peptide library, said method comprising:
(i) obtaining a plurality of amino acid sequences capable of independently-forming secondary structures and/or assemblies of secondary structures and/or folds;
(ii) producing peptides having the amino acid sequences obtained at (i); and
(iii) displaying the peptides at (ii) such that said peptides form secondary structures and/or assemblies of secondary structures and/or folds.

It is to be understood that, notwithstanding the involvement of primary amino acid sequences in the determination of protein secondary structures and folds and the construction of the library, the present invention is not merely a method for producing a library of peptides characterized by their primary amino acid sequences. The present invention provides libraries of peptides characterized by their ability to form stable assemblies of secondary structures and/or tertiary structures, and especially stable tertiary structures. The libraries produced in accordance with the present invention provide a significant advantage over libraries characterized by mere primary sequence, because the libraries of the invention combine individual peptides according to their shape (a major determinant of affinity for a particular ligand), and display these shapes independent of their native context. In contrast, libraries of peptides characterized by primary structure do not comprise peptides necessarily selected for such affinity characteristics.

In this example, the assemblies of secondary structures and/or folds are more likely to be independent i.e., an assembly or fold having a low propensity to be in contact with the rest of the protein from which it is derived, as determined by structural studies or predictive methods. Thus, by "amino acid sequences capable of independently-forming secondary structures and/or assemblies of secondary structures and/or folds" is meant a sequence that, on average, has a predicted probability of forming (i.e., is likely to form) a stated structure without the need for flanking sequences derived from the same protein as that sequence i.e., in its native context, and without the need for artificial scaffolding of the peptide, whether or not such structure formation is autonomous or induced. Alternatively, or in addition, the sequence may have been tested empirically to form one or more of such structures. The advantage of such independence is that structures formed by peptide libraries made as described herein have a greater propensity i.e., likelihood of being stable when displayed e.g., by virtue of being compact when folded and/or with some hydrophobic surface area buried. Preferred fragments have a higher degree of independence predicted from their low contact in the context of the full protein structure, because such fragments will generally not require extensive contact(s) with other sequences in the native protein to fold or retain a folded conformation. "Independence", while construed here to not require the context of the source protein to form particular structures, shall not, in this context, exclude those sequences which are able to form induced folds on target proteins which are distinct from the source protein.

In a particularly preferred example, fragments of proteins that are computationally predicted to fold independently are identified e.g., according to one or more criteria selected from compactness, non-polar buried surface area, and degree of independence, and fragments having a propensity to fold independently are selected.

By "compactness" is meant overall surface area of a fragment, when determined in isolation i.e., when removed from the full protein structure.

By "non-polar buried surface area" is meant the amount of non-polar surface area buried within the fragment.

By "degree of independence" is meant the degree of contact the fragment has with the rest of the protein.

Preferably, fragments of proteins that are computationally predicted to fold independently are identified e.g., according to two or three criteria selected from compactness, non-polar buried surface area, and degree of independence, and fragments having a propensity to fold independently are selected.

More preferably, fragments of proteins that are computationally predicted to fold independently are identified e.g., according to the criteria of compactness, non-polar buried surface area, and degree of independence, and fragments having a propensity to fold independently are selected.

Preferably, the amino acid sequences are capable of forming secondary structures and/or folds and the peptides are displayed so as to form secondary structures and/or folds.

More preferable, the amino acid sequences are capable of forming assemblies of secondary structures and/or folds and the peptides are displayed so as to form assemblies of secondary structures and/or folds.

Still more preferably, the amino acid sequences are capable of forming folds and the peptides are displayed so as to form folds.

A particular structure may form autonomously, or be induced. By "autonomous" is meant that structure formation is not dependent upon the interaction of a primary or secondary structure with a ligand, or by external intervention e.g., by denaturation and renaturation. By "induced" is meant that structure formation depends upon an interaction with a ligand, or by external intervention e.g., by denaturation and renaturation albeit not including constraint of ha peptide by means of an artificial scaffold.

Since the peptides produced by this method may also comprise single amino acid chains that mimic tertiary structures produced by interaction of non-contiguous portions of native proteins, it is also within the scope of the invention for the resultant library to comprise single chain peptide mimetics of tertiary structures.

Preferably, the obtained data set of sequences having a capability for producing a particular structure is refined by size-selection. More preferably, the method of the present invention preferably comprises the additional step of size-selecting sequences at (i) to thereby identify a sub-set of sequences having the average length of an independent protein fold.

Without being bound by theory or mode of action, such size selection permits the identification of a data set of fold sequences that are amenable to large-scale production of synthetic peptides for the purposes of display. Preferred amino acid sequences capable of forming, secondary structures and/or assemblies of secondary structures and/or folds will not exceed 100 or 75 or 50 or 40 or 30 amino acids in length. The minimum length of such sequences is about 5 amino acid residues, however sequences of at least about 15 amino acid residues, more preferably at least 20 amino acid residues, still more preferably at least 25 amino acid residues in length can form such structures. Longer peptides are not to be excluded, especially where it is desired to produce multidomains or mixed domain peptides e.g., for binding to multiple ligands. For convenience in synthesis and display, and as exemplified herein, a preferred size class for peptides having, amino acid sequences capable of forming secondary structures and/or assemblies of secondary structures and/or folds is in the range of about 20 amino acid residues in length to about 30 amino acid residues in length.

By producing, an extensive repertoire of distinct sequence structures e.g., by reducing redundancy and/or identifying related sequences to an additional data set and/or by mutational approaches, peptides capable of forming structurally distinct secondary structures and/or associations of secondary structures and/or folds are produced. As a consequence, the diversity of the peptide library is enhanced, thereby increasing the probability of identifying a peptide having a desirable bioactivity when screening the library. Accordingly, it is preferable that the method of the invention additionally comprises selecting amino acid sequences and/or peptides having distinct structures.

It is also preferred for the method of the invention to additionally comprise identifying redundant sequences and removing or deleting redundant sequences to thereby leave a "non-redundant" or "normalized" plurality of amino acid sequences.

By "redundant" means that two or more secondary and/or tertiary structure are the same or substantially the same, or alternatively, that two or more primary amino acid sequences are sufficiently related so as to form or be predicted to form the same or substantially the same secondary and/or tertiary structures.

"Non-redundant" in this context means that only a limited number of secondary and/or tertiary structures are the same or substantially the same, or alternatively, that only a limited number of primary amino acid sequences are sufficiently homologous so as to form or be predicted to form the same or substantially the same secondary and/or tertiary structures. A "limited number" in this context shall be taken to mean one or two or three or four or five occurrences of each sequence or each structure in the library, preferably one or two or three occurrences, more preferably one or two occurrences and most preferably a single occurrence.

By "normalized" means that the structures are represented in the pool of structures contained within the library at approximately the same frequency independent of the number of occurrences.

Both non-redundant and normalized libraries are sufficient for the purpose of reducing bias in the structure libraries that has been introduced by a bias in the source data employed and/or a natural bias in representation of folds. For ease of downstream processing of primary screening "hits", it is preferred that the libraries are non-redundant, as this eliminates the need for sorting to identify identical or highly-related structures.

Such removal or deletion can be performed at the stage of obtaining amino acid sequences capable of forming secondary structures and/or assemblies of secondary structures and/or folds, or alternatively, at the peptide production stage. Removal of redundant sequences at an earlier stage in the inventive method is preferred, to reduce costs.

In one example, a computational method is employed that removes redundant sequences from the pool of sequences obtained i.e., from the source data, or from a data set of independent folds produced as described herein, or from a size-selected data set of independent folds produced as described herein. In accordance with this example, the PISCES server (Wang and Dunbrack, Bioinformatics 19, 1589-1591, 2003; Wang and Dunbrack. Nucl. Acids. Res. 33, W94-W98, 2005; available from Fox Chase Cancer Center, PA, USA) can be employed to remove sequences such that no two proteins in the set share more than 30% identity with one another. PISCES uses structure alignments to determine sequence alignments and sequence identities. This is a far more accurate procedure for removing sequence-redundant proteins than previous methods. Peptides comprising diverse protein structures are thus produced, and subsequently arrayed or combined to form a combinatorial structural library e.g., a protein fold library.

It is also preferred for the method of the invention to additionally comprise identifying related sequences to the obtained plurality of amino acid sequences and adding those sequences to the plurality of amino acid sequences.

Preferably, the related sequences are identified from a data source that is independent i.e., different to the source from the which the plurality of sequences was originally identified, to maximize the probability that a related sequence is different to one contained in the original data set and, more preferably, using a data source compiled using different criteria to the criteria employed by the original source database. By performing this step, the data set is expanded and made more diverse. This process can be performed for several iteration, theoretically encompassing all available sets of source data referred to herein, thereby capturing the diversity of protein structures in nature. Another advantage of this process step is that is counters the low representation of sequences and structures in any particular database.

The identification of related sequences can be performed at any stage in the process of the invention. For example, related sequences can be identified at the stage of obtaining amino acid sequences capable of forming secondary structures e.g., by collating data from several databases simultaneously. Alternatively, the related sequences can be identified following size selection, or alternatively, using non-redundant data sets. Expansion at the at the stage of obtaining amino acid sequences capable of forming secondary structures, or alternatively, using non-redundant data sets, is preferred. Of these two preferred embodiments, the identification of related sequences using non-redundant data sets is more preferred, because it reduces the size of the query term. Again, it is clearly preferred to perform such steps before peptide synthesis, to reduce costs.

Computational methods can be used to find sequences having high sequence identity and/or homology to the obtained sequences or peptides having those sequences. Preferably, a database that identifies and eliminates sequences having high sequence identity e.g., more than about 30% or about 40% or about 50% or about 60% sequence identity to the query sequences, is utilized.

In a particularly preferred embodiment, the algorithm PSI-BLAST (Altschul et al., Nucl. Acids Res. 25, 3389-3402, 1997) is used to search the UniRef$_{50}$ database (a subset of the UniProt database of all publicly available protein sequences; Bairoch et al., Nucl. Acids Res. 33, D154-D159, 2005), and aligned sequences to the query sequence are identified and/or isolated. Such methods may enhance diversity by about 10-fold or 20-fold or 30-fold or 40-fold or 50-fold.

Alternatively, or in addition, the diversity of the library is enhanced by mutagenesis of peptides that are predicted to form a secondary structure or assembly of secondary structures or fold, using any means known to the skilled artisan. The production of synthetic peptides containing mutations at each position relative to the sequence of the "base" peptide is preferred.

By "base peptide" is meant a peptide that is subjected to mutation including affinity maturation.

Mutations that maintain structure e.g., conservative amino acid substitutions at each position in the peptide are preferred. Such an approach may be saturated i.e., throughout the peptide, or targeted. In one example of a targeted approach, alanine-scanning mutagenesis can be used to determine empirically those residues that are important for structure formation and then mutations can be introduced at those positions.

It is also possible to expand diversity of a recombinant peptide expression library (as opposed to a library of synthetic peptides) by introducing mutations into nucleic acid encoding the peptides, e.g., by random mutagenesis of peptides, by mutagenesis of nucleic acid encoding the peptides e.g., by random mutagenesis, expression in cells having error-prone mismatch-repair systems, use of error-prone polymerases and/or replicases such as Qβ-replicase, inducing translational slippage, expressing nucleic acid in the six different reading frames, etc. Such methods for mutating nucleic acid are described in the scientific literature.

Preferably, a mutational approach such as that explained in the preceding paragraph produces peptides having different affinities for particular ligands and more preferably, produces one or more peptides having higher affinities for one or more ligands. This embodiment includes the affinity maturation of a peptide capable of forming a naturally-occurring structure to thereby enhance or improve the binding affinity of that structure for a ligand, which may be the same or a different ligand to the ligand in respect of which the structure evolved. For example, affinity maturation may be performed to enhance the affinity of the peptide for a peptide or small molecule agonist, antagonist, partial agonist or inverse agonist that mimics the structure of the natural ligand of the base peptide.

Because mutational process and the identification of related sequences may introduce or reintroduce redundancy into a data set of peptide structures, the present invention clearly encompasses combinations of these processes i.e., a combination of mutation with removal of redundant sequences, and a combination of related sequence identification with removal of redundant sequences, and a combination of mutation with removal of redundant sequences and related sequence identification. Such combinations may be iterative i.e., repeated one or two or three or as many times as necessary to produce a non-redundant yet highly diverse data set.

Having determined the capability of a protein fragment to form a secondary structure or association of secondary structures or protein fold, the amino acid sequence producing that structure is determined, and a peptide having the sequence is produced (e.g., by synthetic or recombinant means), and the produced peptide displayed (e.g., by direct display on a physical medium or by phage display or recombinant expression) by means described herein.

For example, the peptides are produced by any synthetic or recombinant means and introduced to or maintained in, conditions sufficient for the peptide to attain a secondary structure, or to assemble or form a fold that it forms in nature. As will be apparent from the preceding description, this may be autonomous or induced e.g., by contacting a ligand with the peptide or incubating the peptide under suitable buffering conditions or physiological conditions.

Suitable display methods will be apparent to the skilled artisan and include, for example, producing the peptides by synthetic means and maintaining the peptides under suitable conditions such that they associate or fold. Such synthetic peptides may be arrayed on a solid surface, e.g., a microarray, or on a plurality of solid surfaces, e.g., a plurality of beads or in microwells.

In this respect, the peptides may be synthesized directly onto a solid surface or immobilized on a solid surface, e.g., using a method known in the art and/or described herein. For example, a parallel array or pool of peptides is produced, e.g., synthetically, and arrayed in a multi-well plate, e.g., using robotic technology. Such arrays are useful for, for example, high-throughput screening of peptides, including phenotype driven screens.

Alternatively, the peptides are displayed using recombinant means. For example, the peptides are expressed on the surface of a phage or a cell or by ribosome display or by in vitro display or the peptides are expressed within a cell or a plurality of cells.

In the case of peptides produced by a recombinant method, the method of the invention preferably additionally comprises determining or identifying nucleotide sequences of nucleic acids capable of encoding the peptides. The skilled artisan will be aware of methods for determining such nucleotide sequences. For example, the nucleotide sequence is obtained from a database, such as, for example, the database of the National Center for Biotechnology Information at the National Library of Medicine at the National Institutes of Health of the Government of the United States of America, Bethesda. Md., 20894. Alternatively, the amino acid sequence is reverse translated by in silico analysis to provide a suitable nucleotide sequence, e.g., using the Reverse Translate software available from Colorado State University.

Preferably, the method of the invention additionally comprises producing or providing nucleic acids comprising the nucleotide sequences capable of encoding the peptides and/or expressing the peptides from the nucleic acids. For example, the method of the invention additionally comprises providing or producing an expression construct comprising the nucleic acid capable of encoding the peptides.

However, it is to be understood that a particularly preferred embodiment of the present invention does not comprise the use or production of recombinant peptides or DNA expression libraries. Synthetic peptide libraries are particularly preferred because they are relatively easy to produce and maintain. For example, synthetic libraries do not require intermediate steps of cloning and/or host cell production or maintenance, and they can be stored for long periods.

Preferably, the method of the invention additionally comprises confirming that the peptides or a subset thereof are displayed such that they fold to produce the requisite or desired structures. Suitable methods for determining a peptide that has attained a desired or requisite structure will be apparent to the skilled artisan and/or described herein, however empirical means are clearly preferred. For example, a sample of the peptides displayed in a library can be assayed using a thermal denaturation assay or circular dichroism. Alternatively or in addition, a displayed peptide can be contacted with a ligand of the structure in nature labelled with a suitable reporter molecule and binding of the ligand to the peptide determined.

By producing libraries comprising combinations of peptides having requisite or desired secondary structure and/or assembly of secondary structures and/or folds, the present invention also facilitates the production of peptide libraries having a relatively low structure redundancy.

In one example, the present invention provides a method for producing a peptide library having a relatively low structure redundancy, said method comprising:
(i) obtaining a plurality of amino acid sequences capable of independently-forming secondary structures and/or assemblies of secondary structures and/or folds;
(ii) identifying redundant structures from the plurality at (i) and removing or deleting redundant sequences capable of forming the redundant structures to thereby leave a non-redundant plurality of amino acid sequences;
(iii) producing peptides having the amino acid sequences of the non-redundant plurality at (ii); and
(iv) displaying the peptides at (iii) such that said peptides form secondary structures and/or assemblies of secondary structures and/or folds.

Non-redundancy i.e., "distinctness" in a non-redundant library produced in accordance with this embodiment means that the structures are not iterative of the same assembly of secondary structures or fold. Preferably, the non-redundant i.e., "distinct" structures are selected according to the compactness of an assembly of secondary structures or a fold, and/or the surface area of an assembly of secondary structures or a fold, and/or the hydrophobic surface area of a fold, and/or the degree of independence. More preferably, the non-redundant structures differ in at least one of these attributes, even more preferably in at least two of these attributes, still more preferably in three attributes and in a most preferred embodiment all four attributes.

It is to be understood that the non-redundant i.e., "distinct" structures may have permissible similarities. It is also clearly permissible for a structure that forms autonomously to be distinct from a structure that needs to be induced e.g., by ligand binding, since such differences indicate subtle distinctions. Other permissible similarities in such non-redundant i.e., "distinct" structures include, for example, the type/class of secondary structures constituting the assembly of secondary structures or folds, and/or the ligand to which the assemblies of secondary structures or folds bind, and/or the binding affinity and/or dissociation constant of an assembly of secondary structures or fold for a ligand and/or their chemical modification e.g., incorporation of one or more labels and/or reporter molecules and/or tags and/or protein transduction domains and/or D-amino acids and/or phosphorylated moieties and/or glycosylated moieties such as sugars. For example, α-helices and/or n-sheets may occur in a variety of distinct assemblies of secondary structures or folds. Similarly, the same ligand may bind to different assemblies of secondary structures or folds, and at different affinities. Rather, the secondary structure may vary in a minor feature, such as, for example, in the size of a turn in the protein domain or the length of a helix or a sheet. Chemical modifications e.g., incorporation of D-amino acids, phosphorylation or glycosylation of amino acids may also modify secondary structures. Such structural variations may control the affinity or specificity with which a protein domain interacts with a target molecule.

The degree of redundancy in a peptide library produced according to this embodiment is low unless, of course, the library is subjected subsequently to mutagenesis such as for the purpose of affinity maturation, which subsequent processes would be understood by a skilled artisan to produce a large number of closely-related sequences and similar structures of different affinities for a particular ligand. Preferably, the degree of redundancy in a primary peptide library i.e., without subsequent mutation or affinity maturation, is such that there are no more than about five peptides in the library capable of forming the same assembly of secondary structures or folds. More preferably, the degree of redundancy in a primary peptide library i.e., without subsequent mutation or affinity maturation, is such that there are no more than four or five peptides in the library capable of forming the same assembly of secondary structures or folds. Even more preferably, the degree of redundancy in a primary peptide library i.e., without subsequent mutation or affinity maturation, is such that there are no more than three peptides in the library capable of forming the same assembly of secondary structures or folds. Still even more preferably, the degree of redundancy in a primary peptide library i.e., without subsequent mutation or affinity maturation, is such that there are no more than two peptides in the library capable of forming the same assembly of secondary structures or folds. In a most particularly preferred embodiment, the degree of redundancy in a primary peptide library i.e., without subsequent mutation or affinity maturation, is such that there is no more than one peptide in the library capable of forming the same assembly of secondary structures or folds.

In a preferred embodiment, the method comprises determining non-redundant i.e., "distinct" structures using a computational methods, such as, for example, employing PISCES. Alternatively, or in addition, such non-redundant sequences are identified by manual searching in silico, such as, for example using SCOP or PDB.

In another example, the present invention provides a method for producing a peptide library having low structure redundancy, said method comprising:
(i) obtaining a plurality of amino acid sequences capable of forming independent-secondary structures and/or assemblies of secondary structures and/or folds;
(ii) producing peptides having the amino acid sequences obtained at (i);
(iii) identifying redundant sequences from the peptides produced at (ii) and removing or deleting peptides having the redundant sequences to thereby leave a non-redundant plurality of amino acid sequences; and
(iv) displaying the peptides at (iii) such that said peptides form secondary structures and/or assemblies of secondary structures and/or folds.

Non-redundancy i.e., "distinctness" in a non-redundant library produced in accordance with this embodiment means that the sequences are sufficiently different to ensure that the displayed peptides form distinct structures as described herein above e.g., with reference to their compactness, surface area, hydrophobic surface area and independence. Preferably, the sequences are not more than about 60% identical, more preferably not more than about 50% identical, still more preferably not more than about 50% identical or not more than about 40% identical at the level of the primary amino acid sequence. In a particularly preferred embodiment, amino acid sequences are not more than about 30% identical to ensure non-redundant structures in the displayed peptide library. Standard sequence alignment and comparison tools can be utilized for this purpose.

It is to be understood that the non-redundant i.e., "distinct" sequences may have permissible sequence similarities that result in the permissible structural similarities discussed herein above, including e.g., incorporation of one or more labels and/or reporter molecules and/or tags and/or protein transduction domains and/or D-amino acids and/or phosphorylated moieties and/or glycosylated moieties such as sugars.

As with other embodiments for producing non-redundant libraries described herein, the degree of redundancy in a peptide library produced according to this embodiment is low unless the library is subjected subsequently to mutagenesis such as for the purpose of affinity maturation. Preferably, the degree of redundancy in a primary peptide library i.e., without subsequent mutation or affinity maturation, is such that there are no more than about two or about three peptides in the library having the a primary amino acid sequence that is more than about 30% identical. This includes allowances for related sequences that form the same structure wherein one sequence forms that structure autonomously and the other sequence requires induction to form the structure, however does not allow for sequences arising by subsequent mutation and/or affinity maturation.

In one example, a computational method is used to find sequences having high sequence identity and/or homology to the obtained sequences or peptides having those sequences. Preferably, a database is searched that identifies and eliminates sequences having high sequence identity e.g., more than 30% or 40% or 50% or 60% sequence identity/similarity to a query sequence.

In an even more preferred embodiment, the present invention provides a method for producing a peptide library, said method comprising:
(i) identifying a plurality of amino acid sequences capable of folding independently from other parts of the proteins in which they are contained in their native contexts;
(ii) size-selecting those sequences at (i) to thereby identify a sub-set of sequences having the average length of an independent protein fold;
(iii) identifying redundant sequences from the sequences selected at (ii) and removing or deleting redundant sequences to thereby leave a non-redundant plurality of amino acid sequences;
(iv) producing peptides from the non-redundant plurality of amino acid sequences at (iii); and
(v) displaying the peptides at (iv) such that said peptides form secondary structures and/or assemblies of secondary structures and/or folds.

Preferably, the displayed peptides form structural folds e.g., in solution or when bound to their target(s).

As with other embodiments described herein, it is entirely permissible to enhance the diversity of the non-redundant plurality of amino acid sequences or the peptides produced there from obtained amino acid sequences, either before or after the peptides are displayed.

In an even more preferred embodiment, the present invention provides a method for producing a peptide library, said method comprising:
(i) identifying a plurality of amino acid sequences capable of folding independently from other parts of the proteins in which they are contained in their native contexts;
(ii) size-selecting those sequences at (i) to thereby identify a sub-set of sequences having the average length of an independent protein fold;
(iii) identifying redundant sequences from the sequences selected at (ii) and removing or deleting redundant sequences to thereby leave a non-redundant plurality of amino acid sequences;
(iv) producing a diverse pool of sequence by a process comprising identifying related sequences to the non-redundant plurality of amino acid sequences at (iii) and adding those sequences to the non-redundant plurality of amino acid sequences at (iii);
(v) producing peptides from the diverse pool of sequences at (iv); and
(vi) displaying the peptides at (v) such that said peptides form secondary structures and/or assemblies of secondary structures and/or folds.

Preferably, the displayed peptides form structural folds e.g., in solution or when bound to their target(s).

Preferably, the identification and elimination of redundant sequences and the production of a diverse pool of sequences are performed using computational methods and by database searching, respectively. In both stages, a percentage limit will be applied to determine the constitution of redundant sequences at (iii) and to the search for related sequences at (iv). It will be understood by a skilled artisan that it is not absolutely necessary for these limits to be the same and such limits at each stage should be determined empirically. In the exemplified embodiment, a percentage limit of 30% was applied to identify and remove redundant sequences, and a percentage limit of 50% was applied for the identification of related sequences. Conveniently, a sequence identity not exceeding about 60% should be used for determining redundancy and for determining relatedness such that no sequences are present in the library having a sequence identity greater than 60% to any other sequence. Preferably, a sequence identity not exceeding about 50% is used for determining redundancy and for determining relatedness such that no sequences are present in the library having a sequence identity greater than 50% to any other sequence. More preferably, a sequence identity not exceeding about 40% should be used for determining redundancy and for determining relatedness such that no sequences are present in the library having a sequence identity greater than 40% to any other sequence. Still more preferably, a sequence identity not exceeding about 30% should be used for determining redundancy and for determining relatedness such that no sequences are present in the library having a sequence identity greater than 30% to any other sequence. As will be known to the skilled artisan, iteration of steps (iii) and (iv) will produce a cut-off value in the peptide library that is the lower of the two levels applied to either step.

In another embodiment, the method additionally comprises providing the amino acid sequences of the secondary structures and/or assemblies of secondary structures and/or folds produced as described herein according to any embodiment e.g., to a person or entity for sale or for screening purposes.

The present invention clearly encompasses the use in drug screening applications of a data set comprising a plurality of non-redundant amino acid sequences capable of forming independent folds or a subset of said plurality selected e.g., on the basis of amino acid content or composition, pI, or a combination thereof.

Accordingly, the present invention also provides a computer-readable medium for use in screening applications said computer-readable medium comprising a database of non-redundant amino acid sequences capable of forming independent folds or a subset of said plurality selected e.g., on the basis of amino acid content or composition, pI, or a combination thereof.

Preferably, each sequence in said plurality of the database corresponds on average to the length of a protein fold. For example, each sequence in said plurality can comprise an upper length of about 50 amino acid residues, more preferably about 40 amino acid residues, still more preferably about 30 amino acid residues. In a particularly preferred embodiment, the data set comprises SEQ ID NOs: 1-30000 or a subset thereof selected e.g., on the basis of amino acid content, amino acid composition, pI, or immunogenicity.

Selection of subsets of sequences from the plurality is particularly useful for particular applications e.g., searching for intrinsic or extrinsic membrane structures, cross-linking structures, etc., and is readily achievable from sequence data or using standard algorithms known to the skilled artisan. For example, preferred amino acid content for selecting a subset of sequences is the presence of a proline, cysteine, arginine, lysine, histidine, aspartate, glutamate, tryptophan, tyrosine, etc. The absence of proline is also preferred, since proline residues disrupt structure. Preferred amino acid compositions for selecting a subset of sequences includes the percentages of sulphur-containing, hydrophobic, hydrophilic, charged, or polar amino acids.

A database can be divided into multiple parts, wherein each part comprises information that is different in nature e.g., one part for structure data and another part for storing information regarding the sequences. A database may also contain additional information e.g., ligands to which the structures bind in nature.

A database of the present invention can be a flat file database or a relational database or an object-oriented database. The database can be internal i.e., a private database not accessible to external users, and typically maintained behind a firewall, by an enterprise. Alternatively, the database can be external i.e., accessible to external users by virtue of being located outside an internal database, and typically maintained by a different entity than an internal database.

A number of external public biological sequence databases, particularly chemical libraries and/or less-refined protein structure data sources referred to herein, are available and can be used with the current invention.

In a further example, the database comprises a population of information that can be modified by users to include new information. The population of information is typically included within a database, and can be identified using the methods of the current invention.

The present invention also provides a computer system for use in screening applications said computer system comprising a computer-readable medium comprising a database of non-redundant amino acid sequences capable of forming independent folds or a subset of said plurality selected e.g., on the basis of amino acid content or composition, pI, or a combination thereof and a user interface allowing a user to input protein structure data and/or ligand structure data e.g., for querying the database and displaying results of a database query. The interface may also permit population of one or more fields of data in the database where a user has authority to populate information.

The interface can be a graphic user interface where entries and selections are made e.g., using a series of menus, dialog boxes, and/or selectable buttons. The interface typically takes a user through a series of screens beginning with a main menu. The user interface can include links to access additional information, including information from other external or internal databases.

A computer system of the present invention that processes input data and displays the results of a database query will typically comprise a processing unit that executes a computer program, such as, for example, a computer program comprising a computer-readable program code embodied on a computer-usable medium and present in a memory function connected to the processing unit. The memory function can be ROM or RAM. The computer program is typically read and executed by the processing unit.

The computer-readable program code relates to a plurality of data files stored in a database.

For example, the computer program can also comprise a computer-readable program code for providing a user interface capable of allowing a user to input structure and/or sequence data for proteins, locating data corresponding to the entered query information, and displaying the data corresponding to the entered query.

Data corresponding to the entered query information is typically located by querying a database as described above.

In another example, the computer system and computer program are used to perform a method of the present invention, such as for refining protein structure data.

A computer system of the present invention can be a stand-alone computer, a conventional network system including a client/server environment and one or more database servers, and/or a handheld device. A number of conventional network systems, including a local area network (LAN) or a wide area network (WAN), are known in the art. Additionally, client/server environments, database servers, and networks are well documented in the technical, trade, and patent literature. For example, the database server can run on an operating system such as UNIX, running a relational database management system, a World Wide Web application, and a World Wide Web Server. When the computer system is a handheld device it can be a personal digital assistant (PDA) or another type of handheld device, of which many are known.

The present invention also provides a peptide library comprising a plurality of non-redundant amino acid sequences capable of forming independent folds or a subset of said plurality selected e.g., on the basis of amino acid content or composition, pI, or a combination thereof.

Preferably, each sequence in said plurality of the library corresponds on average to the length of a protein fold. For example, each sequence in said plurality can comprise an upper length of about 50 amino acid residues, more preferably about 40 amino acid residues, still more preferably about 30 amino acid residues.

In a particularly preferred embodiment, the library comprises a plurality of peptides having sequences comprising SEQ ID NOs: 1-30000 or a subset thereof selected e.g., on the basis of amino acid content, amino acid composition, pI, or immunogenicity.

The present invention also provides a peptide library produced by a method described herein according to any embodiment. In a particularly preferred embodiment, the peptide library is a synthetic peptide library.

The present invention also provides a high-throughput system for drug screening comprising a solid support consisting essentially of or having a plurality of peptides bound directly or indirectly thereto, wherein said plurality of peptides comprises non-redundant amino acid sequences capable of forming independent folds or a subset of said plurality selected e.g., on the basis of amino acid content or composition, pI, or a combination thereof. Preferably, the high-throughput system comprises sufficient sequences to be representative of the diversity of fold structures in nature. The peptides may be arrayed in subsets e.g., on the basis of amino acid content or composition, pI, or a combination thereof. It will be apparent from the foregoing description that the arrayed peptides contained in the high throughput system can be obtained by an intermediate step in a method of the present invention. In use, the high-throughput system of the present invention is used for drug screening to identify one or more ligands of a protein structure, especially a fold structure. Preferably, a peptide library or subset thereof is immobilized on a solid surface, such as, for example, a glass slide or a bead.

Alternatively, the peptide library is displayed, for example, on the surface of a cell or viral particle. For example, the peptide library is a phage display library. Additional suitable libraries include a library of peptides expressed within a cell or within a population of cells, for example within a population of yeast cells.

The libraries of the present invention are suitable for screening to identify a peptide having a desired bioactivity, such as, for example, a peptide that binds to a target molecule and/or inhibits a target interaction. In one example, the present invention additionally provides a process comprising:

(i) performing a method for producing a peptide library according to any embodiment described herein; and (ii) screening the peptide library so produced.

In another example, the present invention additionally provides a process comprising:

(i) obtaining a peptide library that has been produced according to any embodiment described herein; and (ii) screening the peptide library.

These embodiments clearly encompass performing one or more iterations of a screening procedure e.g., a second round of screening employing a peptide library or expression library wherein the members of said library comprise or express peptides having a related structure to the identified peptide. Such "panning" is useful for identifying peptides that bind to a target at higher affinity or lower affinity compared to the peptide identified in primary screens, or have a modified bioactivity compared to the peptide identified in primary screens.

The skilled artisan will also be aware of suitable methods for screening a peptide library, for example, affinity purification or N-hybrid screening, FRET, BRET, protein fragment complementation assay, Fluorescence polarization assays, time resolved capture assay, probing of arrays of the synthetic peptides.

Preferably, these processes further result in the identification and more preferably, the subsequent isolation, of a peptide from the screened peptide library. In such embodiments, the present invention clearly extends to such identified and/or isolated products.

These processes for utilizing the library of the present invention may also comprise determining the secondary structure of a peptide. Alternatively, or in addition, the amino acid sequence of an identified peptide is determined. Alternatively, or in addition, an identified peptide is synthesized, e.g., by recombinant or synthetic means. Alternatively, or in addition, an identified peptide is subjected to mutation or affinity maturation.

In another example, the processes additionally comprise identifying a chemical compound, e.g., a small molecule mimetic of the structure formed by an identified peptide. For example, such a small molecule is a putative drug lead for clinical trial. Methods for predicting the structure of a small molecule and/or identifying a small molecule having a desired structure are described herein and/or known in the art e.g., QASR.

The present invention additionally provides a process comprising:

(i) performing a method for producing a peptide library according to any embodiment described herein;

(ii) screening the peptide library so produced to thereby identify a peptide having a desired structure; and (iii) optionally, providing the peptide or the structure of the peptide to a person such as, for example, in a paper form, machine-readable form, or computer-readable form.

In a preferred embodiment, the peptide or the structure of the peptide is provided with an indication as to its use e.g., as determined by a screen used for its isolation.

In another example, this process further comprises identifying one or more chemical compounds having the secondary structure of the peptide and, preferably, identifying one or more chemical compounds having the same activity as the peptide e.g., as determined by the screen used for its isolation.

DETAILED DESCRIPTION OF THE PREFERRED EMBODIMENTS

The present invention is further described with regard to the following non-limiting examples.

Example 1

Identifying Non-Redundant Data Sets of Protein Folds

Source Data for Protein Structures

Numerous databases comprising structures of protein folds in their native contexts i.e., in the proteins in which they are found, are known in the art.

An example of one such database is the Structural Classification of Protein database (SCOP) available from the Medical Research Council Laboratory of Molecular Biology and/or originally described in Murzin et al., *J. Mol. Biol.* 247, 536-540, 1995. Version 1.69 released July 2005 of the SCOP database comprises the amino acid sequences of approximately 945 protein folds in their native contexts.

Alternatively, as at Feb. 14, 2006, the Protein Data Bank (PDB) comprises the amino acid sequence of approximately 700 protein folds in their native contexts The amino acid sequences contained within the PDB are available from, for example, Research Collaboratory for Structural Bioinformatics, NJ, USA. The PDB is also described in Berman et al., *Nucleic Acids Research,* 28: 235-242, 2000.

The Class, Architecture, Topology, Homologous super family (CATH) database version 2.6.0 (released April, 2005) comprises the amino acid sequences of a large number of distinct protein folds in their native contexts and, in total, approximately 40,000 folds i.e., including redundancies. Information from the CATH database may be accessed from University College London, Department of Biochemistry and Molecular Biology, London UK. The CATH database is also described in Orengo et al., *Structure.* 5: 1093-1108, 1997 and/or Pearl et al., *Nucleic Acids Research.* 33: D247-D251, 2005.

The Fold classification based on Structure-Structure alignment of Proteins (FSSP) database also provides amino acid sequences of protein folds in their native contexts. The FSSP database is available from the European Bioinformatics Institute.

Alternatively, or in addition, the structure of a protein fold or other structure is predicted using an in silico method, such as, for example, a method described supra or threading (Jones, *Curr. Opin. Struct. Biol.* 7:377-87, 1997; Sippl et al., *Structure* 4:15-19, 1996), "profile analysis" (Bowie et al., *Science.* 253:164-70, 1991; Gribskov et al., *Methods Enzymol.* 183:146-59, 1990; Gribskov et al., *Proc. Nat. Acad. Sci. U.S.A.* 84:4355-58, 1989), and "evolutionary linkage"

For example, conventional threading of an amino acid sequence is used to predict the 3 dimensional structure of a peptide or protein comprising said amino acid sequence. Typically, threading is a process of assigning the fold or other structure of the protein by threading (or comparing) its sequence to a library of potential structural templates by using a scoring function that incorporates the sequence as well as the local parameters such as structure and solvent exposure (Rost et al. 270: 471-480, 1997; Xu and Xu Proteins: Structure, Function, and Genetics 40: 343-354, 2000); and Panchenko et al. *J. Mol. Biol.* 296: 1319-1331, 2000). For example, the threading process starts from prediction of the structure of the amino acid sequence and solvent accessibility for each residue of the query sequence. The resulting one-dimensional (1D) profile of the predicted structure is threaded into each member of a library of known 3 dimensional structures. The optimal threading for each sequence-structure pair is obtained using dynamic programming. The overall best sequence-structure pair constitutes the predicted 3 dimensional structure for the query sequence.

Alternatively, the amino acid sequence of a protein fold or other structure is determined by determining or predicting the structure of a peptide comprising a specific amino acid sequence. Methods for predicting the structure of a peptide comprising a specific amino acid sequence are known in the art and include, for example, methods described in US Patent Application No 20020150906, or using a computer program or algorithm, such as, for example, MODELLER, (Sali and Blundell, *J. Mol. Biol.* 234, 779-815, 1993). These techniques rely upon aligning the sequence of a peptide with the sequences of a protein fold or other structure having a previously characterized structure. Such alignment algorithms are known in the art and are accessed through software packages such as, for example BLAST at NCBI. Structural information, i.e., three-dimensional structure, of a query peptide is then be predicted based upon structural information corresponding to the sequence or subsequence aligned in the protein fold or other structures that have previously been characterized.

Obtaining Independent Structures

Computational methods are used to predict the likelihood that any sequence constitutes an independent fold.

For example, the algorithm developed by Tsai et al., Proc. Natl Acad. Sci, (USA) 97, 12038-12043 (2000) for the purpose of studying the dynamics of protein folding is employed. Because Tsai et al. required a procedure for progressively dissecting native protein structures to reveal their anatomy, they were interested in producing a hierarchy of protein domains independent of fragment size, by cutting the protein into building blocks and measuring the relative conformational stabilities of all candidate building blocks. In the criteria used, hydrophobicity was considered by Tsai et al. to be the dominant driving force for protein folding.

In a particular example of the present invention, fragments of proteins that are computationally predicted to fold independently are predicted by "cutting" proteins into hydrophobic folding units, i.e., single segments of a protein that achieve a positive score for attributes including e.g., compactness, non-polar buried surface area, and a propensity to be associated with other part of the protein in nature. Compactness evaluates the overall surface area of a peptide fragment when removed from the full protein structure. Non-polar buried surface area evaluates the amount of non-polar surface area buried within the fragment. A propensity to be associated with other parts of a protein reflects the degree of contact the fragment has with the rest of the protein in its native context, which is highly relevant to the likelihood that a predicted fold will have at least some folded stability when isolated from its native context i.e., when expressed as a peptide. Preferably, this propensity is the dominant attribute and weighted accordingly, since the purpose in this context is to determine independence. The predicted folds should preferably be compact when folded, bury some hydrophobic surface area, and have low contact in the context of a full protein structure in the native context, and thereby be less likely to require extensive contacts with the remainder of the native protein or a heterologous scaffold in order to fold. Implementation of this preferred approach for identifying protein folds to proteins in the Protein Data Bank produces a data file for each of about 45,000 proteins containing residue numbers and scores for each segment in each protein predicted to be independently folding. Of these about 45,000 proteins in an initial data set, approximately 17,500 proteins are predicted to contain at least one segment of 30 amino acid residues or less in length having a positive fragment folding score.

Reducing Redundancy in Amino Acid Sequence and/or Structure

As will be apparent to the skilled artisan from the foregoing description, a preferred peptide library of the present invention preferably has reduced structural redundancy. Accordingly, in some embodiments of the invention it is preferred to produce a library in which peptides identical in structure, albeit not identical in amino acid sequence are not present or are present in limited amounts.

Any one of a number of computational methods are used to identify an remove redundant amino acid sequences from a data set. Such computational methods may select amino acid sequences of protein folds or other structures from one or more databases, compare the sequences to other sequences in the data set and delete the redundant sequences.

In a particularly preferred example, many of the approximately 17,500 proteins referred to in the preceding section that are predicted to contain at least one segment of 30 amino acid residues or less in length having a positive fragment folding score actually comprised similar or identical sequences. To remove the redundancy in this data set, the PISCES server was employed to remove sequences such that no two proteins in the set shared more than 30% identity with one another. PISCES uses structure alignments to determine sequence alignments and sequence identities. This is a far more accurate procedure for removing sequence-redundant proteins than methods described before PISCES was developed. By utilizing the PISCES software, a non-redundant data set comprising a total of 2,011 sequences of 30 amino acid residues or less in length and having a positive fragment folding score were identified. Thus, from an initial data set of about 45,000 proteins were reduced to about 2,000 sequences of folds. This means that less than 5% of protein sequences in the initial data set comprised distinct protein folds.

Enhancing Diversity of the Protein Fold Data Set

In one embodiment, the amino acid sequence diversity in the data set is enhanced to improve the complexity of the peptide libraries. Standard mutational approaches can be applied for this purpose, however the approaches taken for achieving enhanced diversity may differ depending upon whether the peptides are to be produced synthetically or as recombinant peptides in an expression library.

For libraries of synthetic peptides, it is preferred to generate diverse amino acid sequences and then produce synthetic peptides by standard peptide synthesis. In contrast, for enhancing the diversity of recombinant expression libraries, it is necessary to mutate nucleic acids encoding a diverse set of amino acid sequences by site-directed or random mutagenesis approaches.

For example, the amino acid sequences of a plurality of peptide folds can be used as probes in silico to identify related sequences from public databases of protein sequences, and the related sequences included in the data set of protein folds. Accordingly, by aligning a plurality of amino acid sequences capable of forming diverse protein folds can be derived.

In accordance with this example, the inventors have used PSI-BLAST to identify those proteins in the UniRef50 database having homology to 2,011 sequences of protein folds referred to in the preceding section as a non-redundant data set comprising a total of 2,011 sequences of 30 amino acid residues or less in length and having a positive fragment folding score. The UniRef50 database is a subset of the UniProt database of all publicly available protein sequences, such that no two proteins in the set have more than 50% sequence identity to any other sequence i.e., it is a non-redundant database. From these PSI-BLAST searches, the inventors identified regions aligned to the independently-folding segments of the queries, and isolated those sequences from their native contexts as described herein above. To reduce the possibility that the homologous sequences are from well-conserved regions of proteins, subsets of the homologs were selected such that they also had less than 50% identity to one another. Up to a maximum of 20 fragments were selected for each of the 2,011 folds. This procedure resulted in 23,548 non-redundant sequences.

As an alternative to selecting sub-sets of homologues having less than 50% identity to each other, it is possible to simply add all homologous sequences to the dataset of 2,011 sequences and then perform one or more iterations of PISCES to thereby remove redundancies from the data set. For example, using PISCES at 30% cut-off value as described herein above would result in a more stringent selection than selecting homologs such that they also had less than 50% identity to one another and, as a consequence, a smaller data set.

Alternatively, PISCES can be combined with selection of homologs having less than 50% identity to one another.

Because many small, naturally-occurring proteins are likely to have binding properties to other proteins, and many such proteins are enzyme inhibitors, protein hormones, or small components of larger complexes, it may indeed be necessary to remove redundancy from such proteins to attain a desirable non-redundant data set of protein folds. For example, 6,480 proteins with lengths from 10 to 30 amino acids in the Uniref50 database were identified by the present inventors and those proteins having undetermined or non-standard amino acids e.g., designated as X in Uniref50, were removed. The amino acid content of each peptide was calculated, and those peptides with one amino acid type covering more than 25% of the peptide length were also removed. This procedure resulted in 6,452 additional protein folds, which were then combined with the 23,548 non-redundant sequences referred to herein above, thereby producing the 30,000 sequences set forth in SEQ ID NOs: 1-30000.

For peptides to be expressed from a nucleic acid, the foregoing procedures may also be employed and nucleic acids encoding the diverse protein folds synthesized and expressed by convention methods for expressing recombinant proteins. However, this approach is likely to be more cumbersome than producing and cloning a smaller set of nucleic acids and then enhancing diversity in the nucleic acids by mutagenesis, as explained in the following paragraphs.

For example, nucleic acid may be amplified using mutagenic PCR such as by (i) performing the PCR reaction in the presence of manganese; and/or (ii) performing the PCR in the presence of a concentration of dNTPs sufficient to result in misincorporation of nucleotides. Methods of inducing random mutations using PCR are known in the art and are described, for example, in Dieffenbach (ed) and Dveksler (ed) (In: PCR Primer: A Laboratory Manual, Cold Spring Harbour Laboratories, NY, 1995). Furthermore, commercially available kits for use in mutagenic PCR are obtainable, such as, for example, the Diversify PCR Random Mutagenesis Kit (Clontech) or the GeneMorph Random Mutagenesis Kit (Stratagene).

For example, a PCR reaction is performed in the presence of at least about 200 µM manganese or a salt thereof, more preferably at least about 300 µM manganese or a salt thereof, or even more preferably at least about 500 µM or at least about 600 µM manganese or a salt thereof. Such concentrations manganese ion or a manganese salt induce from about 2 mutations per 1000 base pairs (bp) to about 10 mutations every 1000 bp of amplified nucleic acid (Leung et al *Technique* 1, 11-15, 1989).

Alternatively, nucleic acid is mutated by inserting said nucleic acid into a host cell that is capable of mutating nucleic acid. Such host cells are deficient in one or more enzymes, such as, for example, one or more recombination or DNA repair enzymes, thereby enhancing the rate of mutation to a rate that is rate approximately 5,000 to 10,000 times higher than for non-mutant cells. Strains particularly useful for the mutation of nucleic acids carry alleles that modify or inactivate components of the mismatch repair pathway. Examples of such alleles include alleles selected from the group consisting of mutY, mutM, mutD, mutT, mutA, mutC and mutS. Bacterial cells that carry alleles that modify or inactivate components of the mismatch repair pathway are known in the art, such as, for example the XL-1Red, XL-mutS and XL-mutS-Kan$^r$ bacterial cells (Stratagene).

Example 2

Production of Peptides Capable of Forming Folds or Other Structures

Peptide Synthesis

Preferably, a peptide is produced using a synthetic means or method For example, synthetic peptides are prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield. *J. Am. Chem. Soc.*, 85:2149-2154, 1963, or the base-labile Nα-amino protected 9-fluorenylmethoxycarbonyl (Fmoc) amino acids described by Carpino and Han, *J. Org. Chem.*, 37:3403-3409, 1972. Both Fmoc and Boc Na-amino protected amino acids can be obtained from various commercial sources, such as, for example, Fluka, Bachem, Advanced Chemtech, Sigma, Cambridge Research Biochemical, Bachem, or Peninsula Labs. Furthermore, phospho-amino acids or glycol-amino aicds may also be used to generate a phosphorylated synthetic polypeptide. Methods for producing glycopeptides and/or phosphorpeptides will be apparent to the skilled artisan and/or described in Fmoc Solid Phase Peptide Synthesis: A Practical Approach (Chan and White Eds.) Dec. 16, 1999, Oxford University Press.

Generally, chemical synthesis methods comprise the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final peptide. Alternatively, the peptide is retained on the solid support to thereby produce, for example, an array of peptides. By simple modification of this general procedure, it is possible to add more than one amino acid at a time to a growing chain, for example, by coupling a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis. Synthesis. Biology, Vol. 1, for classical solution synthesis. These methods are suitable for synthesis of a peptide.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

Peptides can be also be produced using alternative synthesis methodologies to enhance the efficient production of long peptides, including microwave enabled synthesis, protein ligation of shorter peptide sequences with a peptidyl bond (or alternatively with other covalent bonds such a through oxidation of cysteine residues to form a disulphide bond or the formation of a thioester bond.

Alternative peptide synthesis methods will be apparent to the skilled artisan, such as, for example, methods of simultaneous multiple peptide synthesis, e.g., as described in Houghten *Proc. Karl. Acad. Sci. USA* 82: 5131-5135, 1985 or U.S. Pat. No. 4,631,211.

As will be apparent to the skilled artisan based on the description herein, a peptide may comprise D-amino acids, a combination of D- and L-amino acids, and various unnatural amino acids (e.g., α-methyl amino acids, Cα-methyl amino acids, and Nα-methyl amino acids, etc) to convey special properties. Synthetic amino acids include ornithine for lysine, fluorophenylalanine for phenylalanine, and norleucine for leucine or isoleucine. Methods for the synthesis of such peptides will be apparent tot eh skilled artisan based on the foregoing.

Peptide Analogues

In another embodiment, the library comprises one or more peptide analogues and/or peptide derivatives. In this respect, the library may be made up entirely of peptide analogues or peptide derivatives or a mixture of peptide analogues and peptide; a mixture of peptide derivatives and peptides; or a mixture of peptide analogues, peptide derivatives and peptides.

As used herein, the term "analogue" shall be taken to mean a peptide that is modified to comprise one or more naturally-occurring and/or non-naturally-occurring amino acids. For example, the term "analogue" encompasses a peptide capable of forming a fold or other structure and comprising one or more conservative amino acid changes relative to a base peptide. The term "analogue" also encompasses a peptide comprising, for example, one or more D-amino acids. For example, such an analogue has the characteristic of reduced immunogenicity and/or protease resistance.

As used herein the term "derivative" shall be taken to mean a peptide that is derived from a peptide capable of fold or other structuring to produce a structure or a tertiary structure, e.g., a fragment or processed form of the peptide. The term "derivative" also encompasses fusion proteins comprising the peptide. For example, the fusion protein comprises a label, such as, for example, biotin or an epitope, e.g., a FLAG epitope or a V5 epitope or an HA epitope. Such a tag is useful for, for example, purifying the fusion protein.

Suitable peptide analogues include one or more conservative amino acid substitutions. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), .beta.-branched side chains (e.g., threonine, valine, isoleucine) and aromatic side chains (e.g., tyrosine, phenylalanine, tryptophan, histidine). Those skilled in the art are well aware that the following substitutions are permissible conservative substitutions for maintaing structure: (i) substitutions involving arginine, lysine and histidine; (ii) substitutions involving alanine, glycine and serine; and (iii) substitutions involving phenylalanine, tryptophan and tyrosine.

Analogues of the peptide described herein according to any embodiment are intended to include peptides in which one or more amino acids of the peptide structure are substituted with a homologous amino acid such that the properties of the original peptides are maintained. Preferably conservative amino acid substitutions are made at one or more amino acid residues.

The importance of the hydropathic amino acid index in conferring interactive biological function on a protein is generally understood in the art (Kyte & Doolittle, J. Mol. Biol. 157, 105-132, 1982). It is known that certain amino acids may be substituted for other amino acids having a similar hydropathic index or score and still retain a similar biological activity, for example, the ability to fold or other structure to form a structure and/or a tertiary structure. The hydropathic index of amino acids also may be considered in determining a conservative substitution that produces a functionally equivalent molecule. Each amino acid has been assigned a hydropathic index on the basis of their hydrophobicity and charge characteristics, as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making changes based upon the hydropathic index, the substitution of amino acids whose hydropathic indices are within +/−0.2 is preferred. More preferably, the substitution will involve amino acids having hydropathic indices within +/−0.1, and more preferably within about +/−0.05.

It is also understood in the art that the substitution of like amino acids is made effectively on the basis of hydrophilicity. As detailed in U.S. Pat. No. 4,554,101, the following hydrophilicity values have been assigned to amino acid residues: arginine (+3.0); lysine (+3.0); aspartate (+3.0+/−0.1); glutamate (+3.0+/−0.1); serine (+0.3); asparagine (+0.2); glutamine (+0.2); glycine (0); threonine (−0.4); proline (−0.5+/−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is preferred to substitute amino acids having hydrophilicity values within about +/−0.2 of each other, more preferably within about +/−0.1, and even more preferably within about +/−0.05

It also is contemplated that other sterically similar compounds may be formulated to mimic the key portions of the peptide structure. Such compounds, which may be termed peptidomimetics, may be used in the same manner as the peptides of the invention and hence are also analogues of a peptide of the invention. The generation of such an analogue may be achieved by the techniques of modeling and chemical design known to those of skill in the art. It will be understood that all such sterically similar antimicrobial peptide analogues fall within the scope of the present invention.

Another method for determining the "equivalence" of modified peptides involves a functional approach. For example, a given peptide analogue is tested or analysed for its ability to fold or other structure to produce a structure and/or a tertiary structure e.g., using any screening method described herein.

Preferred analogues of a peptide of the invention will comprise one or more non-naturally occurring amino acids or amino acid analogues. For example, an antimicrobial peptide of the invention may comprise one or more naturally occurring non-genetically encoded L-amino acids, synthetic L-amino acids or D-enantiomers of an amino acid. For example, the peptide comprises only D-amino acids. More particularly, the analogue may comprise one or more residues selected from the group consisting of: hydroxyproline, β-alanine, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylananine 3-benzothienyl alanine 4-chlorophenylalanine, 2-fluorophenylalanine, 3-fluorophenylalanine. 4-fluorophenylalanine, penicillamine, 1,2,3,4-tetrahydro-tic isoquinoline-3-carboxylic acid β-2-thienylalanine, methionine sulfoxide, homoarginine, N-acetyl lysine, 2,4-diamino butyric acid, ρ-aminophenylalanine, N-methylvaline, homocysteine, homoserine, ε-amino hexanoic acid, δ-amino valeric acid, 2,3-diaminobutyric acid and mixtures thereof.

Commonly-encountered amino acids that are not genetically encoded and which can be present, or substituted for an amino acid in an analogue of an antimicrobial peptide of the invention include, but are not limited to, β-alanine (β-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); .beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe (pNH$_2$)); N-methyl valine (MeVal); homocysteine (hCys) and homoserine (hSer).

Other amino acid residues that are useful for making the peptides and peptide analogues described herein can be found, e.g., in Fasman, 1989, CRC Practical Handbook of Biochemistry and Molecular Biology, CRC Press, Inc., and the references cited therein.

The present invention additionally encompasses an isostere of a peptide described herein. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) known to those skilled in the art. Such modifications include modifications of the amide nitrogen, the α-carbon, amide carbonyl, complete replacement of the amide bond, extensions, deletions or backbone cross links. Several peptide backbone modifications are known, including ψ[CH$_2$S], ψ[CH$_2$NH], ψ[CSNH$_2$], ψ[NHCO], ψ[COCH$_2$], and ψ[(E) or (Z) CH=CH]. In the nomenclature used above, ψ indicates the absence of an amide bond. The structure that replaces the amide group is specified within the brackets.

Other modifications include, for example, an N-alkyl (or aryl) substitution (ψ[CONR]), or backbone cross linking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides.

In one embodiment, the peptide analogue is a retro peptide analogue (Goodman et al., *Accounts of Chemical Research*, 12:1-7, 1979). A retro peptide analogue comprises a reversed amino acid sequence of a peptide capable of fold or other structuring to produce the structures and/or tertiary structure.

In a preferred embodiment, a peptide analogue is a retro-inverso peptide (Sela and Zisman, *FASEB J.* 11:449, 1997). Evolution has ensured the almost exclusive occurrence of L-amino acids in naturally occurring proteins. As a consequence, virtually all proteases cleave peptide bonds between adjacent L-amino acids. Accordingly, artificial proteins or peptides composed of D-amino acids are preferably resistant to proteolytic breakdown. Retro-inverso peptide analogues are isomers of linear peptides in which the direction of the amino acid sequence is reversed (retro) and the chirality, D- or L-, of one or more amino acids therein is inverted (inverso) e.g., using D-amino acids rather than L-amino acids, e.g., Jameson et al., *Nature*, 368, 744-746 (1994); Brady et al., *Nature.* 368, 692-693 (1994). The net result of combining D-enantiomers and reverse synthesis is that the positions of carbonyl and amino groups in each amide bond are exchanged, while the position of the sidechain groups at each alpha carbon is preserved.

An advantage of retro-inverso peptides is their enhanced activity in vivo due to improved resistance to proteolytic degradation. i.e., the peptide has enhanced stability. (e.g., Chorev et al., Trends Biotech. 13, 438-445, 1995).

Retro-inverso peptide analogues may be complete or partial. Complete retro-inverso peptides are those in which a complete sequence of an antimicrobial peptide of the invention is reversed and the chirality of each amino acid in a sequence is inverted. Partial retro-inverso peptide analogues are those in which only some of the peptide bonds are reversed and the chirality of only those amino acid residues in the reversed portion is inverted. For example, one or two or three or four or five or six or seven or eight or nine or ten or eleven or twelve or thirteen or fourteen or fifteen or sixteen or seventeen or eighteen or nineteen or twenty or twenty one or twenty two or twenty three or twenty four or twenty five or twenty six or twenty seven or twenty eight or twenty nine or thirty or thirty one or thirty two or thirty three or thirty four or thirty five or thirty six or thirty seven or thirty eight amino acid residues are D-amino acids. Alternatively, 10% or 15% or 20% or 25% or 30% or 35% or 40% or 45% or 50% or 55% or 60% or 65% or 70% or 75% or 80% or 85% or 90% or 95% of the amino acids in a peptide are D-amino acids. The present invention clearly encompasses both partial and complete retro-inverso peptide analogues.

Preferred retro-inverso analogues are partial analogues wherein the complete amino acid sequence of a peptide is reversed and an amino acid residue in said sequence other than glycine is inverted (i.e., substituted with a corresponding D-amino acid residue). Preferably, all amino acid residues other than glycine are inverted.

In another embodiment, a peptide analogue is modified to reduce the immunogenicity of said analogue. Such reduced immunogenicity is useful for a peptide that is to be, for example, injected into a subject. Methods for reducing the immunogenicity of a peptide will be apparent to the skilled artisan. For example, an antigenic region of a peptide is predicted using a method known in the art and described, for example, in Kolaskar and Tongaonkar *FEBS Letters*, 276: 172-174, 1990. Any identified antigenic region may then be modified to reduce the immunogenicity of a peptide analogue, provided that said analogue is capable of fold or other structureing to produce a 10 secondary and/or tertiary structure.

Alternatively, or in addition, Tangri et al., *The Journal of Immunology*: 174: 3187-3196, 2005, describe a process for identifying an antigenic site in a peptide and modifying said site to thereby reduce the immunogenicity of the protein without significantly reducing the activity of said protein. The approach is based on 1) the identification of immunedominant epitopes, e.g., by determining binding to purified HLA molecules; and 2) reducing their binding affinity to HLA-DR molecules to levels below those associated with naturally occurring helper T lymphocyte epitopes. Generally, the approach is based on quantitative determination of HLA-DR binding affinity coupled with confirmation of these epitopes by in vitro immunogenicity testing.

Peptide Derivatives

Peptide derivatives encompass a peptide or an analogue thereof as described herein in any embodiment that is modified to contain one or more-chemical moieties other than an amino acid. The chemical moiety may be linked covalently to the peptide or analogue e.g., via an amino terminal amino acid residue, a carboxyl terminal amino acid residue, or at an internal amino acid residue. Such modifications include the addition of a protective or capping group on a reactive moiety in the peptide, addition of a detectable label, and other changes that do not adversely destroy the activity of the peptide compound (e.g., its ability to form a fold or other structure).

An "amino terminal capping group" of a peptide described herein is any chemical compound or moiety that is covalently linked or conjugated to the amino terminal amino acid residue or analogue of a peptide or analogue. An amino-terminal capping group may be useful to inhibit or prevent intramolecular cyclization or intermolecular polymerization, to protect the amino terminus from an undesirable reaction with other molecules, or to provide a combination of these properties. A peptide of this invention that possesses an amino terminal capping group may possess other beneficial activities as compared with the uncapped peptide, such as enhanced efficacy or reduced side effects. Examples of amino terminal capping groups that are useful in preparing peptide derivatives according to the invention include, but are not limited to, 1 to 6 naturally occurring L-amino acid residues, preferably, 1-6 lysine residues, 1-6 arginine residues, or a combination of lysine and arginine residues; urethanes; urea compounds; lipoic acid ("Lip"); glucose-3-O-glycolic acid moiety ("Gga"); or an acyl group that is covalently linked to the amino terminal amino acid residue of a peptide, wherein such acyl groups useful in the compositions of the invention may have a carbonyl group and a hydrocarbon chain that ranges from one carbon atom (e.g., as in an acetyl moiety) to up to 25 carbons (e.g., palmitoyl group, "Palm" (16:0) and docosahexaenoyl group, "DHA" (C22:6-3)). Furthermore, the carbon chain of the acyl group may be saturated, as in Palm, or unsaturated, as in DHA. It is understood that when an acid, such as docosahexaenoic acid, palmitic acid, or lipoic acid is designated as an amino terminal capping group, the resultant peptide is the condensed product of the uncapped peptide and the acid.

A "carboxyl terminal capping group" of a peptide described herein is any chemical compound or moiety that is covalently linked or conjugated to the carboxyl terminal amino acid residue of the peptide. The primary purpose of such a carboxyl terminal capping group is to inhibit or prevent intramolecular cyclization or intermolecular polymerization, to promote transport of the peptide compound across the blood-brain barrier, and to provide a combination of these properties. A peptide of this invention possessing a carboxyl terminal capping group may also possess other beneficial activities as compared with the uncapped peptide, such as enhanced efficacy, reduced side effects, enhanced hydrophilicity, enhanced hydrophobicity. Carboxyl terminal capping groups that are particularly useful in the peptide compounds described herein include primary or secondary amines that are linked by an amide bond to the α-carboxyl group of the carboxyl terminal amino acid of the peptide. Other carboxyl terminal capping groups useful in the invention include aliphatic primary and secondary alcohols and aromatic phenolic derivatives, including flavenoids, with 1 to 26 carbon atoms, which form esters when linked to the carboxylic acid group of the carboxy-terminal amino acid residue of a peptide described herein.

Other chemical modifications of a peptide or analogue, include, for example, glycosylation, acetylation (including N-terminal acetylation), carboxylation, carbonylation, phosphorylation. PEGylation, amidation, addition of trans olefin, substitution of α-hydrogens with methyl groups, derivatization by known protecting/blocking groups, circularization, inhibition of proteolytic cleavage (e.g., using D amino acids), linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH$_4$, acetylation, formylation, oxidation, reduction, etc.

Other peptide derivatives include, for example, a tag to facilitate isolation of the peptide and/or immobilization of the peptide on a solid surface and/or detection of the peptide. For example, the peptide comprises a biotin tag. Such a biotinylated peptide may be synthesized using known methods. Such a peptide is useful, for example, for immobilizing on a streptavidin coated chip.

Alternatively, or in addition peptide or analogue is fused to a tag or label, such as, for example, influenza virus hemagglutinin (HA) (SEQ ID NO: 30001), Simian Virus 5 (V5) (SEQ ID NO: 30002), polyhistidine (SEQ ID NO: 30003), c-myc (SEQ ID NO: 30004) or FLAG (SEQ ID NO: 30005).

In yet another embodiment the peptide is artificially cyclized by a means, for example, of oxidation of flanking cysteine residues or alternatively by the formation of a thioester linkage. Such constraint should not be required for independent folds, however may be required in some circumstances for assemblies of secondary structures.

In another embodiment, a peptide comprises a linker that facilitates the independent fold or other structureing the peptide to form a structure and/or tertiary structure. A suitable linker will be apparent to the skilled artisan. For example, it is often unfavourable to have a linker sequence with high propensity to adopt α-helix or β-strand structures, which could limit the flexibility of the peptide and consequently its functional activity. Rather, a more desirable linker is a sequence with a preference to adopt extended conformation. In practice, most currently designed linker sequences have a high content of glycine residues that force the linker to adopt loop conformation. Glycine is generally used in designed linkers because the absence of a β-carbon permits the polypeptide backbone to access dihedral angles that are energetically forbidden for other amino acids.

Preferably, the linker is hydrophilic, i.e. the residues in the linker are hydrophilic.

Linkers comprising glycine and/or serine have a high freedom degree for linking of two proteins or peptides, i.e., they enable the fused proteins or peptides to fold or other structure. Robinson and Sauer *Proc. Natl. Acad. Sci.* 95: 5929-5934, 1998 found that it is the composition of a linker peptide that is important for stability and fold or other structureing of a fusion protein rather than a specific sequence. For example, the authors found that a fusion protein comprising a linker consisting almost entirely of glycine was unstable. Accordingly, the use of amino acid residues other than glycine, such as, for example, alanine, cysteine, or serine, is also useful for the production of a linker.

In one embodiment, the linker is a glycine rich linker. Preferably, the linker is a glycine linker that additionally comprises alanine and/or serine.

Exemplary linkers comprise from one to about six glycine and/or serine and/or alanine residues, or an amino acid sequence selected from any one of SEQ ID NOs: 30006 to 30031.

In a particularly preferred embodiment, the linker is a single amino acid residue, preferably a single glycine residue, e.g., conveniently added to the C-terminus or N-terminus of either constituent peptidyl moiety tht it links together.

In another embodiment, the peptide derivative of the invention additionally comprises, for example a sequence of amino acids that facilitate uptake of the peptide into a cell, e.g., a protein transduction domain. For example, the amino acid sequence capable of enhancing, increasing or assisting uptake is the *Drosophila* penetratin targeting sequence. This peptide sequence at least comprises the amino acid sequence CysArgGlnIleLysIleTrpPheGlnAsnArgArg-
MetLysTrpLysLys (SEQ ID NO. 30032) further comprising (Xaa)n after the final Lys residue and followed by Cys wherein Xaa is any amino acid and n has a value greater than or equal to 1. Alternatively, a homologue, derivative or analogue of said sequence is used.

Alternative protein transduction domains are known in the art, and include, for example, a protein transduction domain from the HIV-1 TAT protein, such as, for example the TAT fragment 48-60 (SEQ ID NO: 30036) or a retroinverted analog thereof wherein each residue other than glycine is a D-amino acid residue, or a homolog, derivative or analog of the $TAT_{48-60}$ fragment e.g., any one of SEQ ID NOs: 30033-30035 or any one of SEQ ID NOs: 30037-30040, or a retroinvented analog thereof e.g., any one of SEQ ID NOs: 30041-30048, especially SEQ ID NO: 30048.

Alternate protein transduction domains include non-inverted and retroinverted forms of a Kaposi fibroblast growth factor (FGF) hydrophobic peptide, optionally with a glycine spacer added (e.g., SEQ ID NOs: 30049-30052); a non-inverted form of the signal sequence based peptide 1 (SEQ ID NO: 30053) and a retroinverted form thereof; a non-inverted form of the signal sequence based peptide 2 (SEQ ID NO: 30054) and a retroinverted form thereof; a non-inverted form of transportan protein transduction domain (SEQ ID NO: 30055) and a retroinverted form thereof; a non-inverted form of the an amphiphilic model peptide (SEQ ID NO: 30056) and a retroinverted form thereof; and a non-inverted form of a polyarginine peptide (SEQ ID NO: 30057) and a retroinverted form thereof.

Other protein transduction domains are known in the art, and are clearly useful in the present invention. For example, amino acids 43-58 of *Drosophila* antennapedia, polyarginine, PTD-5, Transportan and KALA (reviewed in Kabouridis, *TRENDS in Biotechnology.* 21: 498-503, 2003).

As explained herein, the protein transduction domain peptide may be produced with a glycine spacer residue that is endogenous to the peptide sequence and/or added to the C-terminus or N-terminus of the endogenous peptide sequence. Preferably, if the peptide is not a retroinverted peptide, the spacer occurs in the native sequence or is added to the C-terminus of the peptide's native sequence during synthesis. Preferably, if the peptide is a retroinverted peptide comprising D-amino acids other than glycine, the spacer occurs at the C-terminus of the corresponding native sequence such that it is introduced at the N-terminus of the retroinverted sequence or is added to the N-terminus of the retroinverted peptide sequence during synthesis. This preferred embodiment produces a configuration such that the protein transduction domain is positioned at the N-terminus of a non-inverted peptide and at the C-terminus of a retro-inverted peptide.

Recombinant Peptide Production

In one embodiment, a peptide is produced by recombinant means or methods. To facilitate the production of a recombinant peptide or fusion protein nucleic acid encoding same is preferably isolated or synthesized. In this respect, the nucleotide sequence of a nucleic acid encoding the peptide is identified using a method known in the art and/or described herein, e.g., reverse translation. Such a nucleic acid is then produced by synthetic means or recombinant means. For example, the nucleic acid is isolated using a known method, such as, for example, amplification (e.g., using PCR or splice overlap extension). Methods for such isolation will be apparent to the ordinary skilled artisan and/or described in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001).

For example, nucleic acid encoding a peptide is isolated using polymerase chain reaction (PCR). Methods of PCR are known in the art and described, for example, in Dieffenbach (ed) and Dveksler (ed) (In: PCR Primer: A Laboratory Manual, Cold Spring Harbour Laboratories, NY, 1995). Generally, for PCR two non-complementary nucleic acid primer molecules comprising at least about 20 nucleotides in length, and more preferably at least 25 nucleotides in length are hybridized to different strands of a nucleic acid template molecule, and specific nucleic acid molecule copies of the template are amplified enzymatically. Preferably, the primers hybridize to nucleic acid adjacent to a nucleic acid encoding the peptide, thereby facilitating amplification of the nucleic acid that encodes the subunit. Following amplification, the amplified nucleic acid is isolated using a method known in the art and, preferably cloned into a suitable vector.

Other methods for the production of a nucleic acid of the invention will be apparent to the skilled artisan and are encompassed by the present invention. For example, the nucleic acid is produced by synthetic means. Methods for synthesizing a nucleic acid are described, in Gait (Ed) (In: Oligonucleotide Synthesis: A Practical Approach, IRL Press, Oxford, 1984). Methods for oligonucleotide synthesis include, for example, phosphotriester and phosphodiester methods (Narang, et al. *Meth. Enzymol* 68: 90, 1979) and synthesis on a support (Beaucage, et al *Tetrahedron Letters* 22: 1859-1862, 1981) as well as phosphoramidate technique, Caruthers, M. H., et al., "Methods in Enzymology," Vol. 154, pp. 287-314 (1988), and others described in "Synthesis and Applications of DNA and RNA," S. A. Narang, editor, Academic Press, New York, 1987, and the references contained therein.

For expressing protein by recombinant means, the peptide encoding nucleic acid is placed in operable connection with a promoter or other regulatory sequence capable of regulating expression in a cell-free system or cellular system to thereby produce an expression construct. For example, nucleic acid comprising a sequence that encodes a peptide placed in operable connection with a suitable promoter is expressed in a suitable cell for a time and under conditions sufficient for expression to occur.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Preferred promoters can contain additional copies of one or more specific regulatory elements to further enhance expression and/or alter the spatial expression and/or temporal expression of said nucleic acid.

As used herein, the term "in operable connection with" "in connection with" or "operably linked to" means positioning a promoter relative to a nucleic acid such that expression of the nucleic acid is controlled by the promoter. For example, a promoter is generally positioned 5' (upstream) to the nucleic acid, the expression of which it controls. To construct heterologous promoter/nucleic acid combinations, it is generally preferred to position the promoter at a distance from the gene transcription start site that is approximately the same as the distance between that promoter and the nucleic acid it controls in its natural setting, i.e., the gene from which the promoter is derived. As is known in the art, some variation in this distance can be accommodated without loss of promoter function.

Should it be preferred that a peptide or fusion protein of the invention is expressed in vitro a suitable promoter includes, but is not limited to a T3 or a T7 bacteriophage promoter (Hanes and Plückthun *Proc. Natl. Acad. Sci. USA*, 94 4937-4942 1997).

Typical expression vectors for in vitro expression or cell-free expression have been described and include, but are not limited to the TNT T7 and TNT T3 systems (Promega), the pEXP1-DEST and pEXP2-DEST vectors (Invitrogen).

Typical promoters suitable for expression in bacterial cells include, but are not limited to, the lacz promoter, the Ipp promoter, temperature-sensitive λL or λR promoters, T7 promoter, T3 promoter, SP6 promoter or semi-artificial promoters such as the IPTG-inducible tac promoter or lacUV5 promoter. A number of other gene construct systems for expressing the nucleic acid fragment of the invention in bacterial cells are well-known in the art and are described for example, in Ausubel et al (In: Current Protocols in Molecular Biology. Wiley Interscience, ISBN 047 150338, 1987), U.S. Pat. No. 5,763,239 (Diversa Corporation) and Sambrook et al (In: Molecular Cloning: Molecular Cloning: A Laboratory Manual, Cold Spring Harbor Laboratories, New York, Third Edition 2001).

Numerous expression vectors for expression of recombinant polypeptides in bacterial cells and efficient ribosome binding sites have been described, and include, for example, PKC30 (Shimatake and Rosenberg, Nature 292, 128, 1981); pKK173-3 (Amann and Brosius, Gene 40, 183, 1985), pET-3 (Studier and Moffat, J. Mol. Biol. 189, 113, 1986); the pCR vector suite (Invitrogen), pGEM-T Easy vectors (Promega), the pL expression vector suite (Invitrogen) the pBAD/TOPO or pBAD/thio—TOPO series of vectors containing an arabinose-inducible promoter (Invitrogen, Carlsbad, Calif.), the latter of which is designed to also produce fusion proteins with a Trx loop for conformational constraint of the expressed protein; the pFLEX series of expression vectors (Pfizer nc., CT, USA); the pQE series of expression vectors (QIAGEN, CA. USA), or the pL series of expression vectors (Invitrogen), amongst others.

Typical promoters suitable for expression in yeast cells such as for example a yeast cell selected from the group comprising *Pichia pastoris, S. cerevisiae* and *S. pombe*, include, but are not limited to, the ADH1 promoter, the GAL) promoter, the GAL4 promoter, the CUP1 promoter, the PHO5 promoter, the nmt promoter, the RPR1 promoter, or the TEF1 promoter.

Expression vectors for expression in yeast cells are preferred and include, but are not limited to, the pACT vector (Clontech), the pDBleu-X vector, the pPIC vector suite (Invitrogen), the pGAPZ vector suite (Invitrogen), the pHYB vector (Invitrogen), the pYDI vector (Invitrogen), and the pNMT1, pNMT41, pNMT81 TOPO vectors (Invitrogen), the pPC86-Y vector (Invitrogen), the pRH series of vectors (Invitrogen), pYESTrp series of vectors (Invitrogen).

Typical promoters suitable for expression in viruses of eukaryotic cells and eukaryotic cells include the SV40 late promoter, SV40 early promoter and cytomegalovirus (CMV) promoter, CMV IE (cytomegalovirus immediate early) promoter amongst others. Preferred vectors for expression in mammalian cells (e.g., 293, COS, CHO, T cells, 293T cells) include, but are not limited to, the pcDNA vector suite supplied by Invitrogen, in particular pcDNA 3.1 myc-His-tag comprising the CMV promoter and encoding a C-terminal 6xHis and MYC tag; and the retrovirus vector pSRαtkneo (Muller et al., *Mol. Cell. Biol.*, 11, 1785, 1991).

A wide range of additional host/vector systems suitable for expressing an antimicrobial peptide or fusion protein of the present invention are available publicly, and described, for example, in Sambrook et al (In: Molecular cloning, A laboratory manual, second edition, Cold Spring Harbor Laboratory, Cold Spring Harbor, N.Y., 1989).

Means for introducing the isolated nucleic acid molecule or a gene construct comprising same into a cell for expression are well-known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA). PEG-mediated DNA uptake, electroporation and microparticle bombardment such as by using DNA-coated tungsten or gold particles (Agracetus Inc., WI, USA) amongst others.

Peptide Isolation

In one embodiment, the peptide is isolated or purified following synthesis or expression. Standard methods of peptide purification are employed to obtain an isolated peptide, including but not limited to various high-pressure (or performance) liquid chromatography (HPLC) and non-HPLC peptide isolation protocols, such as size exclusion chromatography, ion exchange chromatography, phase separation methods, electrophoretic separations, precipitation methods, salting in/out methods, immunochromatography, and/or other methods.

Alternatively, affinity purification is useful for isolating a fusion protein comprising a label. Methods for isolating a protein using affinity chromatography are known in the art and described, for example, in Scopes (In: Protein purification: principles and practice, Third Edition, Springer Verlag, 1994). For example, an antibody or compound that binds to the label (in the case of a polyhistidine tag this may be, for example, nickel-NTA) is preferably immobilized on a solid support. A sample comprising a fusion protein is then contacted to the immobilized antibody or compound for a time and under conditions sufficient for binding to occur. Following washing to remove any unbound or non-specifically bound protein, the fusion protein is eluted.

Example 3

Peptide Display Methods

Solid Supports

Peptides capable of forming folds or other structures can be synthesized directly onto a solid support, such as, for example, a microchip or immobilized on the solid support to thereby produce an array of peptides. Suitable methods for immobilizing a peptide on a solid support are known in the art and include, for example, either direct linkage (e.g. by covalent linkage, such as, for example, Schiff's base formation, disulfide linkage, or amide or urea bond formation) or indirect linkage. Methods of generating such a protein chip are known in the art and are described in for example U.S. Patent Application No. 20020136821, 20020192654, 20020102617 and U.S. Pat. No. 6,391,625 or Lee et al, *Proteomics.* 3: 2289-2304, 2003.

In one embodiment, the peptides are pooled or a parallel array is produced. For example, each candidate peptide is produced individually (i.e., in isolation from other peptides), a number or a plurality of different peptides are then pooled. Two or more of these pools of peptides are then pooled, and if necessary, this process is repeated. Accordingly, pools of several thousands or millions of peptides may be produced. The largest of these pools may then be screened to determine whether or not it comprises a peptide having a bioactivity of interest. Should the pool comprise such a peptide, one or more groups of smaller pools (i.e. sub-pools) of peptides are screened to determine which comprise the peptide of interest. This process can be iteratively repeated with pools of descending size until the individual peptide of interest is isolated (i.e., the pool of peptides is deconvoluted). Alternatively, a pool of a smaller number of peptides (e.g. 10 or 100) may be directly screened to determine which, if any, of the peptides are capable of modulating a phenotype of interest.

It is also possible to discriminate individual peptides from mixtures of up to about 100 peptides by mass spectrometry during the screening process. The individual peptides can then be readily synthesized using standard methods from the mass spectrometry data and their efficacy validated. Methods for validating a peptide will be apparent to the skilled person, e.g., using a method described herein. For example, the peptide is administered to a cell, tissue or organism and its effect on the phenotype of interest determined. Alternatively, or in addition, the peptide is administered to an animal (e.g., an animal model of a disease) and its effect on the phenotype of interest (e.g., the disease phenotype) is determined along with any other phenotypes that the peptide may modulate (e.g., toxicology screening).

As will be apparent to the skilled artisan the present invention clearly encompasses the production of multiple different libraries. Accordingly, the present invention also includes pooled libraries. For example, the present invention encompasses the pooling of two or more libraries. In one embodiment, the libraries are derived from the same organism/s. In another embodiment, the libraries are derived from different organisms (e.g. a library derived from eukaryotes comprising a compact genome, and another library derived from bacteria).

Peptides that are displayed on the surface of a solid support or maintained in a solution are preferably maintained in a neutral buffer to facilitate fold or other structureing of the peptides into protein fold or other structures or subfold or other structures. Preferably, such a buffer does not comprise significant levels of a detergent or a reducing agent (e.g., dithiothreitol) or a denaturing reagent, e.g., urea.

In Vitro Display

In an alternative embodiment, the peptide library is an in vitro display library (i.e., the peptides are displayed using in vitro display wherein the expressed peptide is linked to the nucleic acid from which it was expressed such that said peptide is presented in the absence of a host cell). For example, the peptide library is a ribosome display library. The skilled artisan will be aware that a ribosome display library directly links mRNA encoded by an expression construct to the peptide that it encodes. To display a nascent polypeptide, nucleic acid encoding it is cloned downstream of an appropriate promoter (e.g., bacteriophage T3 or T7 promoter) and a ribosome binding sequence, optionally including a translatable spacer nucleic acid (e.g., encoding amino acids 211-299 of gene III of filamentous phage M13 mp19) that stabilizes the expressed fusion protein within the ribosomal tunnel. Ribosome complexes are stabilized against dissociation from the peptide and/or its encoding mRNA by the addition of reagents such as, for example, magnesium acetate or chloroamphenicol.

Ribosome Inactivation Display

Alternatively, the library is a ribosome inactivation display library, e.g., as described in Tabuchi, *Biochem Biophys Res Commun.* 305:1-5, 2003 or a covalent display library Phage Display In yet another embodiment, the peptide library is a phage display library wherein the expressed peptides or protein fold or other structures are displayed on the surface of a bacteriophage, as described, for example, in U.S. Pat. No. 5,821,047 and U.S. Pat. No. 6,190,908. The basic principle described relates to the fusion of a first nucleic acid comprising a sequence encoding a peptide or protein to a second nucleic acid comprising a sequence encoding a phage coat protein, such as, for example a phage coat proteins selected from the group, M13 protein-3, M13 protein-7, or M13, protein-8. These sequences are then inserted into an appropriate vector, e.g., a vector capable of replicating in bacterial cells. Suitable host cells, such as, for example *E. coli*, are then transformed with the recombinant vector. Said host cells are also infected with a helper phage particle encoding an unmodified form of the coat protein to which a nucleic acid fragment is operably linked. Transformed, infected host cells are cultured under conditions suitable for forming recombinant phagemid particles comprising more than one copy of the fusion protein on the surface of the particle. This system has been shown to be effective in the generation of virus particles such as, for example, a virus particle selected from the group comprising λ phage, T4 phage, M13 phage, T7 phage and baculovirus. Such phage display particles are then screened to identify a displayed protein having a conformation sufficient for binding to a target protein or nucleic acid.

Cell-Based Display

In yet another embodiment, the peptide library is a bacterial display library wherein the expressed peptides or protein fold or other structures are displayed on the surface of a bacterial cell. The cells displaying the expressed peptides or protein fold or other structures are then used for biopanning as described, for example, in U.S. Pat. No. 5,516,637. Alternatively, the library is a yeast display library, e.g., as described in U.S. Pat. No. 6,423,538 or a mammalian display library, as described in Strenglin et al *EMBO J,* 7, 1053-1059, 1988.

Alternatively, the library of peptides is displayed by expressing the peptides in a cell or in a population of cells using a method known in the art and/or described herein. For example, the each of the peptides in the library is expressed in a separate cell.

Example 4

Confirming Structural Integrity of Displayed Peptides

Preferably, the correct folding of the peptides is confirmed by any one of a verity of methods. Naturally, such procedures are generally be performed by way of sampling a structure library, to assess its structural integrity.

Circular Dichroism

For example, a random sample of the peptides in the library is analyzed using circular dichroism. Circular dichroism spectroscopy is performed by passing plane polarized light through a birefringent plate, which splits the light into two plane-polarized beams oscillating along different axes (e.g., fast and slow). When one of the beams is retarded by 90° (using a quarter-wave retarder) then the two beams which are now 90° out of phase are added together, the result is circularly polarized light of one direction. By inverting the two axes such that the alternate beam is retarded than circularly polarized light of the other direction is generated. The result of adding the right and left circularly polarized that passes through the optically active sample is elliptically polarized light, thus circular dichroism is equivalent to ellipticity. By determining the absorption of a purified peptide in solution at various wavelengths and comparing the absorption to expected absorptions for proteins and/or peptides having the predicted structures, it is possible to confirm that the peptides of the library have the correct structure.

Thermal Denaturation

Alternatively, or in addition, correct folding or structural integrity of the library is confirmed using a thermal denaturation assay. In adapting such an assay to the present invention, the fluorescence of a peptide from the library is monitored at about 340 nm, with excitation at about 295 nm, e.g., using a spectrophotometer. Fluorescence data is acquired at a variety of temperatures, e.g., between about 4° C. and 90° C. Optionally, the melting curve for free tryptophan is subtracted from the results obtained for the peptide to account for the intrinsic temperature dependence of tryptophan fluorescence. A significant reduction in the fluorescence of a peptide as the temperature increases indicates that the peptide is capable of achieving a structure and has denatured. Thermal denaturation assays are known in the art and described, for example, in Socolich et al., *Nature*, 437: 512-518, 2005. In one example, the thermal denaturation profile obtained for a peptide from the library is compared to the thermal denaturation profile of the protein fold or other structure as it occurs in nature to thereby determine whether or not the peptide has assumed the correct conformation.

Ligand Binding

Alternatively, or in addition, correct folding or structural integrity of the library is confirmed by contacting the library of peptides with one or more ligands, e.g., a known antibody that is known to bind to a conformational epitope as opposed to a linear epitope. Binding of the ligand(s) to the library indicates that the library comprises peptides capable of forming a structure. For example, the library is assayed using an ELISA or FLISA assay. In adapting such an assay to the present embodiment of the invention, the peptide library or cells displaying same are immobilised onto a solid surface, e.g., a microplate well or a pin. An antibody that is known to bind to a conformational is epitope is brought into direct contact with the immobilized library of peptides for a time and under conditions sufficient for an antibody-antigen complex to form. The antibody is preferably labelled with an enzymatic label, e.g., horse-radish peroxidase in the case of an ELISA or a fluorescent label in the case of a FLISA. Following washing to remove unbound or non-specifically bound antibody, a substrate of the enzyme is added and metabolisation of said substrate detected. Alternatively, the fluorescent marker is detected by fluorescent means. Presence of a metabolite of the substrate or fluorescence is indicative of a structure (i.e., a conformational epitope) to which the antibody is capable of binding.

Example 5

Screening Procedures

It will be apparent from the disclosure herein that the libraries produced in accordance with the present invention are particularly useful for identifying novel drug leads for therapeutic purposes. Several screening methods can be employed, as described below.

Affinity Purification of Peptides

In one embodiment, the peptide library of the present invention is screened using affinity purification. Affinity purification techniques are known in the art and are described in, for example, Scopes (In: Protein purification: principles and practice, Third Edition, Springer Verlag, 1994). Methods of affinity purification typically involve contacting the peptides in the library with a specific target molecule, e.g., a target protein or nucleic acid, and, following washing to remove unbound or non-specifically bound peptides, eluting those peptides that remain bound to the target protein or nucleic acid. By performing increasingly stringent washes, peptides having higher affinity for the target molecule are identified.

In one example, a protein chip or series of pins having immobilized thereon a peptide library of the invention is contacted with a target, e.g., a target protein or nucleic acid. Preferably, the target is labelled with a detectable marker, e.g., a fluorescent marker. It is also preferred that each of the peptides is immobilized at a predetermined site, thereby facilitating identification of the peptide. Following washing to remove any unbound target, the location of bound label is detected. The location of bound label is indicative of a peptide capable of binding to the target molecule. The identity of the peptide may then be conformed. e.g., using a method described herein, e.g., MALD-TOF.

Surface Plasmon Resonance

Alternatively the library is screened using a surface-plasmon resonance assay, such as, for example, Biacore sensor chip technology (Biacore AB, UK). The Biacore sensor chip is a glass surface coated with a thin layer of gold modified with carboxymethylated dextran, to which a target molecule, e.g., protein or nucleic acid is covalently attached. The peptide library of the invention is then brought into contact with the target molecule. Essentially, a surface plasmon resonance assay detects changes in the mass of the aqueous layer close to the chip surface, through measuring changes in the refractive index. Accordingly, when a peptide from a library of the present invention binds to the target protein or nucleic acid the refractive index increases.

As will be apparent to the skilled artisan another biosensor, such as, for example, an evanescent biosensor, a membrane based biosensor (as described in AU 623,747, U.S. Pat. No. 5,234,566 and USSN 20030143726) or a microcantilever biosensor (as described in USSN 20030010097) is useful for screening the peptides of the present invention.

Biosensor Detection

Alternatively, a biosensor based on the detection of diffractive optics technology (light-scattering) is used to determine a peptide having a bioactivity of interest. Such biosensors are available commercially, e.g., from Axela Biosensors Inc., Toronto, Canada. Alternatively a biosensor may be used which is based on acoustic resonance, such as that produced by Akubio, Cambridge UK.

Other Ligand Binding Assays

Alternatively, the peptide library is screened to identify a peptide capable of binding to a receptor, e.g., a G-protein coupled receptor (GPCR). For example, a GPCR chip is used to screen a library of the invention essentially as described in Fang et al., *Chembiochem.*, 3: 987-991, 2002).

Alternatively, the peptide is identified using a screen, such as, for example, a radioimmunoassay (RIA), an enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, eg LC MS/MS), biosensor technology, evanescent fiber-optics technology or protein chip technology. Such methods are known in the art and/or described herein.

Forward and Reverse Hybrid Assays

A preferred form of screening identifies a peptide capable binding to a protein and/or a peptide capable of reducing, preventing or inhibiting the interaction of a protein with another molecule, e.g., another protein, a peptide, an antibody or a nucleic acid.

For example, a peptide is identified that is capable of binding to a target protein or peptide using the two-hybrid assay described in U.S. Pat. No. 6,316,223 and Bartel and Fields, The Yeast Two-Hybrid System, New York, N.Y., 1997. The basic mechanism described requires that the binding partners are expressed as two distinct fusion proteins in an appropriate host cell, such as for example bacterial cells, yeast cells, or mammalian cells. In adapting the standard two-hybrid screen to the present purpose, a first fusion protein consists of a DNA-binding fold or other structure fused to the target protein, and a second fusion protein consists of a transcriptional activation fold or other structure fused to a peptide from the library of the present invention. The DNA-binding fold or other structure binds to an operator sequence which controls expression of one or more reporter genes. The transcriptional activation fold or other structure is recruited to the promoter through the functional interaction between the peptide from the library of the present invention and the target protein. Subsequently, the transcriptional activation fold or other structure interacts with the basal transcription machinery of the cell, thereby activating expression of the reporter gene(s), the expression of which can be determined.

As used herein, the term "reporter gene" shall be taken to mean a nucleic acid that encodes a peptide, polypeptide or protein that displays a physically measurable property that alters in a way that can be measured and correlated with changes in the biological activity or a target protein or nucleic acid. Reporter molecules are known in the art, and include, but are not limited to, proteins that fluoresce, for example green fluorescence protein, proteins that induce a colour change in the presence of a substrate, for example *E. coli* β-galactosidase, molecules that confer growth characteristics on the host cells, such as for example HIS1, and molecules that induce the death or reduced growth ability of the host cells, such as for example URA3 and CYH2CYH3.

Other modifications of the N-hybrid screens are known in the art, such as for example the PolIII two hybrid system, the Tribrid system, the ubiquitin based split protein sensor system and the Sos recruitment system as described in Vidal and Legrain *Nucl. Acid Res.* 27(4), 919-929 (1999) or the three hybrid assay as described in Zhang et al (In: Bartel and Fields, The Yeast Two-Hybrid System, New York, N.Y. pp 289-297, 1997). All of these systems are contemplated by the present invention.

A preferred screening assay identifies one or more peptides in a library of the invention that antagonize or inhibit the interaction between a target protein and another molecule, e.g., a protein or nucleic acid. Accordingly, reverse 'n'-hybrid screens are employed to identify agonist molecules. Reverse hybrid screens differ from the forward hybrid screens supra in that they use a counter selectable reporter marker(s), such as for example the URA3 gene, the CYH2 gene or the LYS2 gene, to select against interactions between the target protein or nucleic acid and another protein or nucleic acid. Cell survival or cell growth is reduced or prevented in the presence of a drug or a toxigenic substrate of the counter selectable reporter gene product, which is converted by the counter selectable marker to a toxic compound, such as for example the URA3 gene product which confers lethality in the presence of the drug 5-FOA. Accordingly, cells in which the interaction between the target protein and another molecule is blocked or inhibited survive in the presence of the substance. This is because the counter selectable reporter molecule will not be expressed, and accordingly, the substrate will not be converted to a toxic product or the drug (in the case of cycloheximide) will not be active against the essential target encoded by the reporter gene. Such a result indicates that the peptide is an inhibitor of the interaction between the target protein or nucleic acid and another molecule.

Suitable reverse N-hybrid, e.g., reverse two-hybrid systems are known in the art and described, for example, by Watt et al. (U.S. Ser. No. 09/227,652). For example, wherein a protein-protein interaction is being assayed, the binding of the two protein binding partners reconstitutes a functional transcriptional regulatory protein, such as, for example, by virtue of the binding partners being expressed as fusion proteins wherein each fusion protein comprises a portion of a transcriptional regulatory protein that does not modulate transcription without the other portion (eg., a fusion protein comprising a transcriptional activator fold or other structure and a fusion protein comprising a DNA-binding fold or other structure, as described supra). A cell in which the fusion proteins are expressed also comprises a counter selectable reporter gene operably under the control of the reconstitution of the transcription factor. Accordingly, in the absence of inhibition of the protein interaction, the counter selectable reporter gene is expressed, thereby killing the cell when cultured in the presence of a suitable substrate (e.g., 5-FOA for an URA3 counter-selectable reporter gene). A cell that displays a peptide from a library of the invention, wherein said peptide antagonizes or inhibits the protein interaction, survives even in the presence of the substrate, as the counter-selectable reporter gene is not expressed.

As will be known to the skilled artisan, the reverse 'n'-hybrid technique briefly described above is readily modified for use in I-hybrid, 2-hybrid or 3-hybrid assays.

Screens for Modified Phenotype

In another embodiment, nucleic acid encoding the peptide library of the present invention is introduced into a plurality of suitable host cells using the methods of introducing recombinant expression vectors described herein. Cells are then monitored for a change in phenotype, such as, for example, as described in Xu et al. (In: *Nature Genetics* 27, 23-29, 2001). Examples of phenotypic changes include, but a not limited to, a phenotypic change selected from the group consisting of modulation of cellular proliferation, morphological changes, resistance to toxins, susceptibility to toxins and gene expression changes. In adapting the described technique to the present invention, appropriate host cells are transformed or transfected with nucleic acid encoding a peptide library of the invention. Alternatively, synthetic or recombinant peptides isolated from the expression libraries of the present invention is incubated with the host cells, in the presence of a polypeptide that facilitates the uptake of peptides into host cells, i.e., a protein transduction domain. Said host cells are then monitored for specific phenotype changes, such as, for example, gene expression changes monitored using DNA microarrays. The nucleic acid encoding the peptide that induces the phenotypic change is then isolated. Further testing of the peptide that induces the desired change in phenotype is clearly envisaged, such as, for example, two-hybrid analysis to determine which proteins the peptides interacts with, and which cellular pathways it is affect.

Screens for Antimicrobial Activities

Alternatively, or in addition, a peptide library is screened to determine an antimicrobial peptide. For example, the peptide library of peptides are brought into direct contact with a population of microorganisms (e.g., bacteria) for a time and under conditions sufficient for the microorganisms to grow. By determining a peptide that prevents or reduces microbial growth, an anti-microbial peptide is determined. Suitable screening methods are known in the art and described, for example, in Steinberg and Lehrer, *Methods Mol. Biol.*, 78: 169-88, 1997.

Further Peptide Characterization

Following screening a peptide library of the present invention, a peptide is further characterized ed using any of a number of known methods. For example, the peptide is identified using a method selected from the group consisting of Edman sequencing, mixed peptide sequencing, mass spectrometry including MALDI-TOF, ESI and ion trap analysis amongst others.

For example, the identity of a peptide is identified using Edman sequencing (essentially as described by Edman, *Arch. Biochem. Biophys.*, 22, 475-483, 1949) to determine the N-terminal sequence of the peptide and comparing this sequence to a known sequence Preferably, the peptide is separated from a contaminating molecule, such as, for example another protein, prior to Edman sequencing. Following isolation of a peptide, the amino terminus of said protein is derivatized with phenylisothiocyanate under basic conditions. For example, the base used in this step is a non-nucleophile such as, for example, a triethylamine or diisoproylethylamine. This coupling step produces a phenylthiocarbamyl peptide or protein. The thiocarbonyl function of the phenylthiocarbamyl peptide or protein is a moderately strong nucleophile, and under acidic conditions it will cleave the carbonyl carbon of the adjacent peptide bond. This cleavage step results in the production of an anilothiazolinone of the terminal amino acid and leaves the original peptide or protein shortened by one amino acid residue. The anilothiazolinone of the terminal amino acid has different solubility properties from the peptide or protein. As such, it can be extracted and subjected to further analysis. The shortened peptide or protein again has a bare amino terminus, and, as a consequence, can be subjected to additional cycles of coupling, cleavage, and extraction.

The extracted anilothiazolinone of the terminal amino acid, however, is not stable. Under acidic aqueous conditions, anilothiazolinones rearrange rapidly to form more stable phenylthiohydantoins, which are amenable to analysis. A stable phenylthiohydantoin is then analyzed by, for example, UV absorption detection reverse phase high performance liquid chromatography, to determine the identity of the terminal amino acid.

Following determining the N-terminal sequence of a peptide, this sequence is compared to a database of amino acid sequences to thereby determine whether or not the derived sequence is identical to or substantially identical to a known sequence. Such a database is available, for example, at NCBI.

Alternatively, a peptide is identified using mixed-peptide sequencing, as described in Damer et al, *J. Biol. Chem.* 273, 24396-24405, 1998.

Preferably, a peptide is identified using mass spectrometry. For example a peptide isolated in a screening method described herein is ionised using a method, such as, for example, electrospray ionisation (ESI; Fenn et al, *Science*, 246, 64-71, 1989 or Wilm et al, *Nature*, 379, 466-469, 1996), matrix assisted laser desorption/ionisation (MALDI; Karas and Hillenkamp, *Anal. Chem.*, 60, 2299-2301, 1988) or atmospheric pressure chemical ionization. Following ionization, the mass of the molecular ions produced is analysed using, for example, a quadrupole mass analyser (Burlingame et al, *Anal. Chem.* 70, 674R-716R), ion trap mass analysis (Cooks et al, *Chem. Eng. News*, 69, 26, 1991), time of flight (TOF) analysis (Yates, *J. Mass Spectrom.* 33, 1-19, 1998), fourier transform ion cyclotron mass spectrometry (U.S. Pat. No. 3,937,955).

Following determining the sequence of the peptide identified in the screen or a fragment thereof, the determined sequence is compared to a database of sequences to determine whether or not the determined sequence is identical to or substantially identical to a known sequence. Such a database is available, for example at NCBI or ExPASY or Swiss-Prot. Furthermore, as a mass spectrometer also determines the mass of a peptide, polypeptide or protein, this information is also useful in identifying an immunogenic protein, such as, by comparison to a protein mass library, such as, for example, that provided by the UK Human Genome Mapping Project Resource Centre.

As used herein the term "ExPASY" shall be taken to mean the Expert Protein Analysis System at the Swiss Institute of Bioinformatics at Basel University 4056, Basel, Switzerland.

As used herein the term "Swiss-Prot" shall be taken to mean the protein sequence database of the Swiss Institute of Bioinformatics at Basel University 4056, Basel, Switzerland.

Biomolecular interaction analysis-mass spectrometry (BIA-MS) is also useful for detecting and/or characterise and/or identify a peptide from a peptide library of the invention having a desired bioactivity (Nelson et al. *Electrophoresis* 21: 1155-1163, 2000).

In the case of a peptide produced using recombinant techniques, the identity of the peptide may be determined, for example, by determining the nucleotide sequence of the nucleic acid encoding said peptide using standard methods in the art and performing an in silico translation to thereby identify the peptide.

Affinity Maturation of Identified Peptides

In one embodiment, a peptide identified in a screen is mutated to thereby improve the bioactivity of the peptide, e.g., the affinity with which the peptide binds to a target molecule and/or the specificity with which a peptide binds to a target molecule. Methods for mutating a peptide will be apparent to the skilled artisan and/or are described herein.

In another embodiment, the peptide is cyclized to enhance affinity and/or stability.

Diagnostic and Therapeutic Applications

As will be apparent to the skilled artisan, the libraries of the present invention are suitable as reagents for the therapeutic or prophylactic treatment of a subject. For example, a peptide capable of mimicking a structure of an infectious organism or an allergen is useful as a vaccine to prevent or treat an infection or an allergic reaction.

Alternatively, a peptide capable of binding to a target protein or for preventing a target interaction is useful for the treatment of a disease or disorder.

Accordingly, in one embodiment, the present invention provides a composition, preferably, a pharmaceutical composition comprising a peptide identified in a screen described herein according to any embodiment.

Formulation of a pharmaceutical compound will vary according to the route of administration selected (e.g., solution, emulsion, capsule). An appropriate composition comprising the identified modulator to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, Remington's Pharmaceutical Sciences, 17th Edition, Mack Publishing Co., Pa., 1985). For inhalation, the agent can be solubilized and loaded into a suitable dispenser for administration (e.g., an atomizer, nebulizer or pressurized aerosol dispenser).

Furthermore, where the agent is a protein or peptide, the agent can be administered via in vivo expression of the recombinant protein. In vivo expression can be accomplished via somatic cell expression according to suitable methods (see, e.g. U.S. Pat. No. 5,399,346). In this embodiment, nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

As will be apparent to a skilled artisan, a compound that is active in vivo is particular preferred. A compound that is active in a human subject is even more preferred. Accordingly, when manufacturing a compound that is useful for the treatment of a disease it is preferable to ensure that any components added to the peptide does not inhibit or modify the activity of said peptide.

The peptide libraries of the present invention are also useful for identifying and/or producing a peptide useful for the diagnosis and/or prognosis of a disease or disorder. Accordingly, such a peptide may be provided in a form suitable for diagnosing a disease or disorder. For example, the peptide is immobilized on a solid substrate. Alternatively, the peptide is labelled with a detectable marker, e.g., a fluorescent marker. Alternatively, a kit is provided for the diagnosis of a disease or disorder.

For example, a peptide capable of binding to a target is immobilised on a solid substrate. A second peptide capable of binding to a distinct site on the target is labelled with a detectable marker. Such peptides are then useful for the detection of the target in a biological sample using a sandwich-type assay.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09567373B2). An electronic copy of the "Sequence Listing" will also be available from the USPTO upon request and payment of the fee set forth in 37 CFR 1.19(b)(3).

We claim:

1. A peptide library having low structure redundancy, wherein the peptide library comprises a plurality of different chemically-synthesized peptides or recombinantly-expressed peptides that each consist of a single segment of a protein corresponding to a hydrophobic folding unit that forms a secondary structure independently, and wherein no more than five peptides of the plurality are predicted to form the same secondary structure, wherein the plurality of different chemically-synthesized peptides or recombinantly-expressed peptides comprises at least a subset of the amino acid sequences set forth in SEQ ID NOs: 1-30000, wherein each of the plurality of different chemically-synthesized peptides or recombinantly-expressed peptides is covalently attached to a solid support.

2. The peptide library according to claim 1, wherein the plurality of different chemically-synthesized peptides or recombinantly-expressed peptides comprises all of the amino acid sequences set forth in SEQ ID NOs: 1-30000.

3. A method of isolating a peptide that consists of a single hydrophobic folding unit that forms a secondary structure independently comprising screening the peptide library having low structure redundancy according to claim 1 to thereby isolate a peptide from it.

* * * * *

UNITED STATES PATENT AND TRADEMARK OFFICE
CERTIFICATE OF CORRECTION

PATENT NO. : 9,567,373 B2  Page 1 of 1
APPLICATION NO. : 14/038660
DATED : February 14, 2017
INVENTOR(S) : Paul Michael Watt et al.

It is certified that error appears in the above-identified patent and that said Letters Patent is hereby corrected as shown below:

In the Specification

Column 34, Line 12, "oraanism(s)" should read --organism(s)--

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*